US010463492B2

(12) United States Patent
Tylis et al.

(10) Patent No.: US 10,463,492 B2
(45) Date of Patent: Nov. 5, 2019

(54) SYSTEMS AND DEVICES FOR SETTING AN ANCHOR

(71) Applicant: Edwards Lifesciences Corporation, Irvine, CA (US)

(72) Inventors: Arie Tylis, Kiryat Mitzkin (IL); Nikolay Gurovich, Hadera (IL); Eran Goldberg, Nesher (IL); Boaz Manash, Givat Ada (IL); Dan Rottenberg, Haifa (IL); Hagar Adika, Tel Aviv (IL); Tal Regev, Tel Mond (IL); Dikla Kersh, Karkur (IL); Danny M Garmahi, Hadera (IL); Hernan Altman, Kiryat Tivon (IL); Amir Blumenfeld, Tel Aviv (IL)

(73) Assignee: Edwards Lifesciences Corporation, Irvine, CA (US)

( * ) Notice: Subject to any disclaimer, the term of this patent is extended or adjusted under 35 U.S.C. 154(b) by 112 days.

(21) Appl. No.: 15/353,657

(22) Filed: Nov. 16, 2016

(65) Prior Publication Data
US 2017/0135817 A1 May 18, 2017

Related U.S. Application Data

(60) Provisional application No. 62/256,527, filed on Nov. 17, 2015, provisional application No. 62/256,524, filed on Nov. 17, 2015.

(51) Int. Cl.
*A61F 2/24* (2006.01)
*A61B 17/04* (2006.01)
(Continued)

(52) U.S. Cl.
CPC ............ *A61F 2/2445* (2013.01); *A61B 8/085* (2013.01); *A61B 8/0883* (2013.01); *A61B 8/12* (2013.01);
(Continued)

(58) Field of Classification Search
CPC .. A61F 2/2478; A61F 2/2487; A61B 17/0057; A61B 17/0467; A61B 2017/00592; A61B 2017/048
See application file for complete search history.

(56) References Cited

U.S. PATENT DOCUMENTS 1,527,291 A  2/1925 Zorraquin
2,623,521 A  12/1952 Shaw
(Continued)

FOREIGN PATENT DOCUMENTS

WO      2005/102181 A1  11/2005
WO  WO/2012/099418      7/2012
WO      2014/134624 A1   9/2014

OTHER PUBLICATIONS

Herlambang, et al., Realtime Integral Videography Using Intra-Operative 3-D Ultrasound for Minimally Invasive Heart Surgery.
(Continued)

*Primary Examiner* — Carrie R Dorna
(74) *Attorney, Agent, or Firm* — Andrew S. Flior; Snell & Wilmer

(57) ABSTRACT

An anchoring system and related methods are provided for treatment of dilated hearts and of functional valve regurgitation, the system comprising one or more self-expandable or manually expandable anchors and associated devices for fixating a valve splint within the heart. For example, a spade-shaped assembly may be configured to be deployed in a right ventricle of the heart and to stabilize a puncturing instrument to puncture the septum. Various puncturing instruments may also be part of the anchoring system, including one or more of a flexible needle having a multiplicity of slits disposed along the length of the needle, a trocar catheter with a retractable head, and a catheter needle having a blunt introducer to protect nearby tissue within the
(Continued)

heart during advancing a guidewire. A cutter catheter and puncture location catheter may also be part of the system and be used during treatment.

22 Claims, 23 Drawing Sheets

(51) Int. Cl.
*A61B 8/12* (2006.01)
*A61B 8/00* (2006.01)
*A61B 8/08* (2006.01)
*A61B 17/00* (2006.01)

(52) U.S. Cl.
CPC ............ *A61B 8/42* (2013.01); *A61B 17/0401* (2013.01); *A61B 2017/00243* (2013.01); *A61B 2017/00783* (2013.01); *A61B 2017/0409* (2013.01); *A61B 2017/0419* (2013.01); *A61B 2017/0464* (2013.01); *A61F 2/2466* (2013.01); *A61F 2/2487* (2013.01)

(56) References Cited

U.S. PATENT DOCUMENTS

| | | | |
|---|---|---|---|
| 4,742,829 A | 5/1988 | Law et al. | |
| 5,098,388 A | 3/1992 | Kulkashi et al. | |
| 5,139,485 A | 8/1992 | Smith et al. | |
| 5,226,890 A | 7/1993 | Ianniruberto et al. | |
| 5,258,003 A | 11/1993 | Ciaglia et al. | |
| 5,292,310 A | 3/1994 | Yoon | |
| 5,478,329 A | 12/1995 | Ternamian | |
| 5,591,191 A | 1/1997 | Kieturakis | |
| 5,601,537 A | 2/1997 | Frassica | |
| 5,669,883 A | 9/1997 | Scarfone et al. | |
| 5,671,747 A | 9/1997 | Connor | |
| 5,676,682 A | 10/1997 | Yoon | |
| 5,755,697 A | 5/1998 | Jones et al. | |
| 5,810,776 A | 9/1998 | Bacich et al. | |
| 5,961,440 A | 10/1999 | Schweich, Jr. et al. | |
| 6,007,481 A | 12/1999 | Riek et al. | |
| 6,045,497 A * | 4/2000 | Schweich, Jr. .. | A61B 17/00234 128/898 |
| 6,050,936 A | 4/2000 | Schweich, Jr. et al. | |
| 6,156,006 A | 12/2000 | Brosens et al. | |
| 6,210,336 B1 | 4/2001 | Fredriksen | |
| 6,293,952 B1 | 9/2001 | Brosens et al. | |
| 6,616,684 B1 | 9/2003 | Vidlund et al. | |
| 6,969,354 B1 | 11/2005 | Marian | |
| 7,056,294 B2 | 6/2006 | Khairkhahan et al. | |
| 7,241,267 B2 | 7/2007 | Furia | |
| 7,766,812 B2 | 8/2010 | Schroeder et al. | |
| 8,163,013 B2 | 4/2012 | Machold et al. | |
| 8,425,402 B2 | 4/2013 | Annest et al. | |
| 8,444,566 B2 | 5/2013 | Agmon | |
| 8,500,628 B2 | 8/2013 | Frassica et al. | |
| 8,777,841 B2 | 7/2014 | Frassica et al. | |
| 9,011,531 B2 | 4/2015 | Rourke et al. | |
| 2004/0049211 A1 * | 3/2004 | Tremulis ............ | A61B 17/0401 606/153 |
| 2005/0075723 A1 | 4/2005 | Schroeder et al. | |
| 2005/0222488 A1 | 10/2005 | Chang et al. | |
| 2006/0052821 A1 * | 3/2006 | Abbott ............... | A61B 17/0057 606/213 |
| 2006/0122633 A1 * | 6/2006 | To .................... | A61B 17/00234 606/139 |
| 2006/0259074 A1 | 11/2006 | Kelleher et al. | |
| 2007/0066863 A1 | 3/2007 | Rafiee et al. | |
| 2007/0083168 A1 | 4/2007 | Whiting et al. | |
| 2007/0203391 A1 | 8/2007 | Bloom et al. | |
| 2007/0265658 A1 | 11/2007 | Nelson et al. | |
| 2008/0009888 A1 * | 1/2008 | Ewers ................ | A61B 17/0401 606/151 |
| 2008/0249467 A1 | 10/2008 | Burnett et al. | |
| 2008/0294251 A1 | 11/2008 | Annest et al. | |
| 2009/0088678 A1 | 4/2009 | Noda et al. | |
| 2009/0093726 A1 | 4/2009 | Takayama et al. | |
| 2009/0118612 A1 | 5/2009 | Grunwald et al. | |
| 2010/0010538 A1 * | 1/2010 | Juravic ............. | A61B 17/0401 606/228 |
| 2010/0016655 A1 | 1/2010 | Annest et al. | |
| 2010/0160788 A1 | 6/2010 | Davies et al. | |
| 2010/0274081 A1 | 10/2010 | Okoniewski | |
| 2011/0178537 A1 | 7/2011 | Whitman | |
| 2013/0030522 A1 | 1/2013 | Rowe et al. | |
| 2013/0165735 A1 | 6/2013 | Khairkhahan et al. | |
| 2013/0245450 A1 | 9/2013 | Prins et al. | |
| 2013/0296902 A1 | 11/2013 | Vonderwalde et al. | |
| 2013/0310752 A1 | 11/2013 | Kawaura | |
| 2014/0094647 A1 | 4/2014 | Schweich, Jr. et al. | |
| 2015/0018876 A1 | 1/2015 | Ewers et al. | |
| 2015/0045879 A1 | 2/2015 | Longoria et al. | |
| 2015/0105611 A1 | 4/2015 | Schweich, Jr. et al. | |

OTHER PUBLICATIONS

Flato et al., Ultrasound-Guided Venous Cannulation in a Critical Care Unit, Rev. bras. ter. intensiva vol. 21 No. 2 São Paulo Apr./Jun. 2009, pp. 1-11.

Int'l. Search Report for PCT/US2016/062581, Completed Mar. 3, 2017.

Int'l. Search Report for PCT/US2016/062556, Completed Feb. 27, 2017.

\* cited by examiner

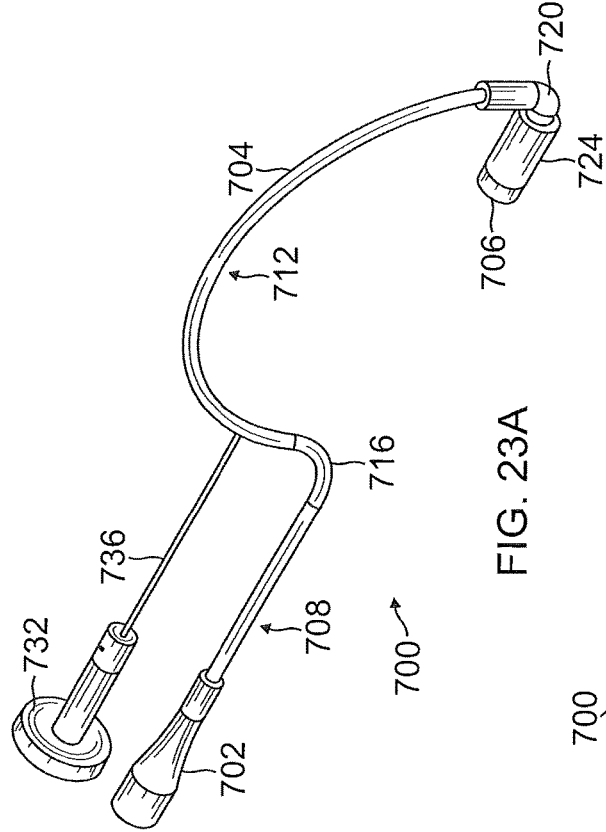
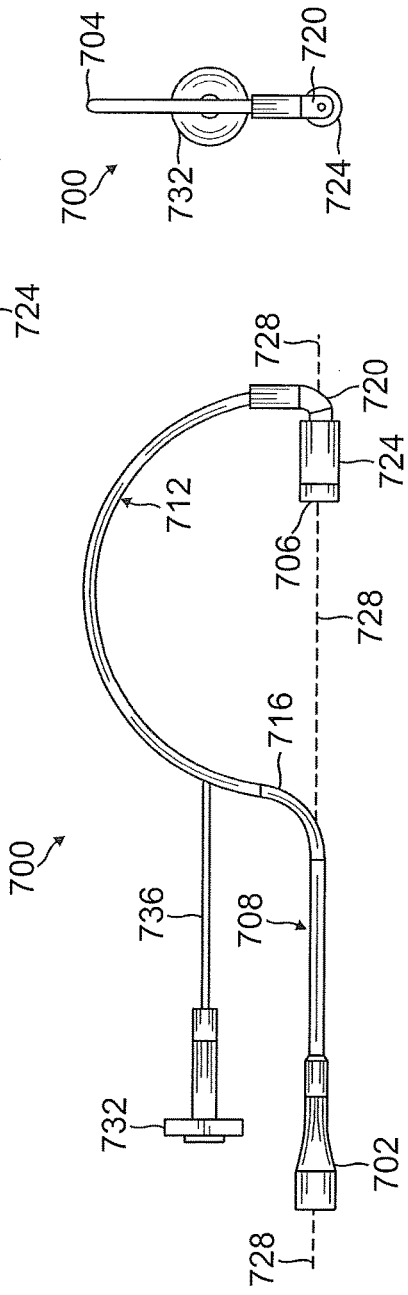
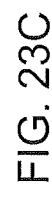
FIG. 23A
FIG. 23B
FIG. 23C

SYSTEMS AND DEVICES FOR SETTING AN ANCHOR

PRIORITY

This application claims the benefit of and priority to the U.S. Provisional application, entitled "Systems And Devices For Setting An Anchor," filed on Nov. 17, 2015 having application Ser. No. 62/256,527 and U.S. Provisional application, entitled "Ultrasound Probe for Cardiac Treatment," filed on Nov. 17, 2015 having application Ser. No. 62/256,524, which application is incorporated by reference herein in its entirety.

BACKGROUND

Heart failure can occur when the left ventricle of the heart becomes enlarged and dilated as a result of one or more of various etiologies. Initial causes of heart failure can include chronic hypertension, myocardial infarction, mitral valve incompetency, and other dilated cardiomyopathies. With each of these conditions, the heart is forced to overexert itself in order to provide a cardiac output demanded by the body during various demand states. The result can be an enlarged left ventricle.

A dilated or enlarged heart, and particularly a dilated or enlarged left ventricle, can significantly increase tension and stress in heart walls both during diastolic filling and systolic contraction, which contributes to further dilatation or enlargement of chambers of the heart. Prior treatments for heart failure include pharmacological treatments, assist devices such as pumps, and surgical treatments such as heart transplant, dynamic cardiomyoplasty, and Batista partial left ventriculectomy. These prior treatments are described briefly in U.S. Pat. No. 5,961,440, entitled "Heart Wall Tension Reduction Apparatus and Method," issued on Oct. 5, 1999, the entirety of which is incorporated by reference herein.

A more recent concept for treating heart failure applies one or more splints onto the heart, to reduce myocardial muscular stresses encountered during pumping. Examples of such approaches are disclosed in U.S. Pat. No. 7,766,812, entitled "Methods and devices for improving mitral valve function," issued on Aug. 3, 2010, the entirety of which is incorporated herein by reference. One example includes one or more transventricular splints placed across the left ventricle. Each splint may include a tension member extending across the ventricle with anchors disposed on opposite ends of the tension member and placed on the external surface of the heart.

Mitral valve incompetency or mitral valve regurgitation is a common comorbidity of congestive heart failure. As the dilation of the ventricle increases, valve function generally worsens, which results in a volume overload condition. The volume overload condition further increases ventricular wall stress, thereby advancing the dilation process, which further worsens valve dysfunction.

In heart failure, the size of the valve annulus (particularly the mitral valve annulus) increases while the area of the leaflets of the valve remains constant. This may lead to an area of less coaptation of the valve leaflets, and, as a result, eventually to valve leakage or regurgitation. Moreover, in normal hearts, the annular size contracts during systole, aiding in valve coaptation. In heart failure, there is poor ventricular function and elevated wall stress. These conditions tend to reduce annular contraction and distort annular size, often exacerbating mitral valve regurgitation. In addition, as the chamber dilates, the papillary muscles (to which the leaflets are connected via the chordae tendonae) may move radially outward and downward relative to the valve, and relative to their normal positions. During this movement of the papillary muscles, however, the various chordae lengths remain substantially constant, which limits the full closure ability of the leaflets by exerting tension prematurely on the leaflets. This condition is commonly referred to as "chordal tethering." The combination of annular changes and papillary changes results in a poorly functioning valve.

It can be desirable to provide a therapy which corrects the valve incompetency. A heart with even a small amount of regurgitation may benefit from not only the stress reducing functions of the ventricular splints as described above, but also from an elimination of the regurgitation, which will further off-load pumping requirements of the myocardium.

Surface area of an anchor and/or size of the anchor can correspond to the ability of an anchor to withstand forces due to tension from reshaping the heart and ongoing beating of the heart (although, other design features and material properties may also contribute to the ability of the anchor to withstand tension forces). To be most effective and safe, anchors would ideally be able to withstand high forces, including forces as high as 17 Newtons (N) or higher, while the splint maintains the heart in a desired shape. Further, the anchor should have a large enough surface area to spread out and reduce the pressure on the myocardium. If the pressure gets too high on an area (e.g., a small, focused pressure area) of the heart, this can lead to myocardium necrosis, which can itself lead to migration and sinking of the anchor into the tissue. Accordingly, large anchors, or anchors with a large surface area, may be required, and the larger size/area can make implantation of the anchor difficult and can require opening the heart, chest, and/or sternum, and/or may require other highly invasive procedures.

Currently available methods of mitral valve repair or replacement typically require opening the chest and/or heart, e.g., to gain direct access to the valve and its annulus or another portion of the heart. This type of access typically necessitates a use of cardiopulmonary bypass, which can introduce additional complications to the surgical procedure. Since the implantation of the splints themselves do not require the patient to be on cardiopulmonary bypass, it would be advantageous to devise a technique which could improve the mitral valve without any need for cardiopulmonary bypass. The ability to improve the mitral valve function without the need for cardiopulmonary bypass would be an advantage, both in conjunction with ventricular splinting, and also as a stand-alone therapy. Indeed, it would be desirable to have systems, apparatuses, and methods capable of a deploying an anchor with an ability to withstand high pressures (e.g., an anchor having a large surface area) using a less invasive, or minimally invasive procedure.

Devices and methods for medical treatment that may be used for improving heart valve function are described herein. These may include a self-expandable anchor system and related methods for assisting in treating an apposition of heart valve leaflets so as to improve poorly functioning heart valves, using less invasive treatments/procedures.

SUMMARY

Systems, assemblies, apparatuses, and related methods are provided for medical treatment, including for transcatheter medical treatments and/or for treatment of dilated hearts (e.g., dilated left ventricle) or functional mitral valve regurgitation within a human heart. Any treatment of a dilated left ventricle may simultaneously result in treatment (fixing or prevention) of functional mitral valve regurgitation. The systems, assemblies, apparatuses, and methods may include an anchoring system that comprises an anchor for securing a mitral valve splint ("MV Splint") in the heart. A spade-shaped assembly (while the term "spade-shaped" is used, this is meant to encompasses a variety of different shapes and sizes) may be configured to be deployed in a right ventricle of the heart and to stabilize a catheter during penetrating the septum. An outer curved needle may be configured to penetrate the septum. The outer curved needle may comprise a hollow tube having a multiplicity of slits (e.g., S-shaped slits) disposed along the length of the needle so as to accommodate sharp curving of the needle. The outer curved needle may be further configured to deploy an inner needle into the left ventricle. A trocar catheter may be configured for puncturing tissue within the heart without damaging other nearby tissue. An introducer system or introducer assembly for interventional cardiology procedures may comprise an atraumatic and/or blunt shape introducer to protect nearby tissue within the heart during advancing a guidewire through a moving tissue, such as a beating heart. A threaded introducer may be configured for advancing a guidewire and/or other instruments through a moving tissue, such as a beating heart, in a controlled manner that helps prevent damage to surrounding tissue.

In an exemplary embodiment, an anchoring system for medical treatment, including treatment of heart dilation and/or functional mitral valve regurgitation comprises an anchor that can be used for fixating a splint, e.g., a mitral valve splint within a human heart. The anchoring system may include one or more or all of the following: a spade-shaped assembly configured to be deployed in a right ventricle of the heart and to stabilize a catheter during penetrating the septum between the right ventricle and the left ventricle; a curved needle configured to penetrate the septum, the curved needle comprising a hollow tube having a multiplicity of slits (e.g., S-shaped slits) disposed along the length of the curved needle, the curved needle may be configured to pass through a catheter or a portion of the spade-shaped assembly and may also be configured to deploy an inner needle from the curved needle into the left ventricle; a trocar catheter configured for puncturing tissue; an introducer system for interventional cardiology procedures; and a threaded introducer configured for temporarily anchoring in a moving tissue and allowing advancement of a guidewire and/or other instruments therethrough.

In one exemplary embodiment, an anchor (e.g., of an anchoring system) comprises a ring having a circularly configured wire having atraumatic ends which meet at a break, the wire capable of being expanded into a straightened configuration suitable for loading the anchor into a lumen of a catheter, e.g., a delivery catheter. In one embodiment the ring may be formed of a shape memory material (e.g., nitinol or other shape memory alloy) and/or may have elastic properties. In one embodiment, the ring may be formed from stainless steel or another strong material. In one exemplary embodiment, the atraumatic ends of the wire forming the ring comprise spherical portions of the wire configured to prevent damage to nearby tissues during delivery and deployment of the anchor within the heart. The anchor may also comprise a cover in one or multiple pieces, the cover may be supported by the ring so as to assume a generally circular configuration. The cover may also be configured to contact an exterior surface of the heart and/or allow tissue ingrowth into the cover. A tension member (e.g., a cord, cable, wire, braided fibers, etc.) may be engaged with the cover such that pulling the tension member or cord tightens the cover into a deployed configuration (e.g., a circular, disc-shaped, pie-shaped, or cone-shaped configuration). In one exemplary embodiment, the cover is configured to change from the deployed configuration (e.g., circular, flattened, disc-shaped, pie-shaped, or cone-shaped configuration) to a collapsed or low profile configuration when the cord is loosened. In one exemplary embodiment, the cover may comprise a surface area suitable to eliminate or limit migration of the anchor into tissue of the heart and to withstand forces due to tension of the tension member or cord of 10-25 Newtons (N), 14-20 N, or at least 17 N.

In one exemplary embodiment, the anchor or a portion of the anchor (e.g., the ring and/or the cover) is configured to be stretched/opened/changed from an expanded or deployed configuration (e.g., a circular or ring-shaped configuration) to a low profile configuration (e.g., a straightened configuration) such that the anchor may be loaded into a lumen of a catheter for delivery through a puncture within the heart in the low profile configuration, and wherein the anchor changes from the low profile configuration (e.g., straightened configuration) to the deployed configuration (e.g., the circular or ring-shaped configuration) as it is pushed out of the lumen of the catheter. When in the deployed configuration (e.g., a circular/ring-shaped/pie-shaped/cone-shaped configuration), pulling the tension member or cord draws the cover taut toward the center of the circle/ring, thereby producing the an expanded configuration of the cover (e.g., a circular, flattened/disc-shaped/pie-shaped configuration of the cover) when not tensioned against the heart wall. The tension member or cord can pull the anchor against the exterior surface of the heart wall, myocardium, and/or pericardium such that the anchor lays flat against the surface with the tension member or cord passing through the puncture in the heart wall, myocardium, and/or pericardium; however, as the tension is increased the tension member or cord can pull the center of the anchor inwardly causing the anchor and its cover to take on a cone-like shape.

In one exemplary embodiment, the cover of an anchor may be comprised of a strip of suitable material having a first, straight edge folded over to form a hole or passage extending along the length of the strip and configured to receive the ring, and a second edge comprising a series folded tabs configured to receive the tension member or cord whereby pulling the tension member or cord draws the cover into the circular/disc-shaped/pie-shaped configuration. In one exemplary embodiment, the cover is comprised of any of various polymer materials, such as polyethylene terephthalate (PET), ultra-high-molecular-weight polyethylene (UHMWPE), or other similar material. In one exemplary embodiment, the cover further comprises one or more ribbons of the polymer material woven so as to provide an anchor suitable for contacting an exterior surface of the heart. The cover may comprise or consist of a polymer, PET, polytetrafluoroethylene (PTFE), expanded polytetrafluoroethylene (ePTFE), UHMWPE, a metal, and/or a non-metal (e.g., carbon fibers).

In one exemplary embodiment, an anchor (e.g., of an anchoring system) may comprise a coiled wire. The coiled wire may comprise a base portion and a top portion, the base portion may be configured to contact the exterior surface of the heart, the myocardium, and/or the pericardium, the top portion may be configured to fixedly receive the tension member or a cord drawn through the center of the coiled wire and the puncture in the heart, and the coiled wire may comprise several turns in which the diameter of the coil decreases in passing from the base portion to the top portion.

In one exemplary embodiment, the diameter of each adjacent turn of the several turns of the coiled wire may decrease with a difference less than the diameter of the wire so as to configure a cone-shaped anchor possessing a large area of contact with the surface of the heart. In one exemplary embodiment, the diameter of adjacent turns/coils of the several turns/coils decreases with a difference greater than the diameter of the wire so as to configure a telescope-shaped anchor which provides a large contact area that increases as a function of tension in the tension member or cord. In one exemplary embodiment, the coiled wire may be wound so as to form at least a lower level or base portion and an upper level or top portion, the lower level being configured to provide a relatively large area of contact with the exterior surface of the heart while preventing the upper level and the tension member or cord from being drawn under tension into the puncture in the wall of the heart. In one embodiment, multiple coils of the coiled wire may have the same or a similar diameter.

In one exemplary embodiment, a spade-shaped assembly (e.g., of an anchoring system) may comprise a catheter, a needle (e.g., a first needle), and a wire spade. The catheter may include a lumen, and the catheter may be flexible. The needle may include a sharp distal end, which may be configured for puncturing a septum between the right ventricle and a left ventricle of a heart (e.g., a beating heart). The needle may be disposable within the lumen of the catheter and moveable out of the lumen to puncture tissue, e.g., to puncture the septum. The needle may be curved and/or flexible. The needle may freely pass through the lumen, may be connected through controls at a proximal end (e.g., on a proximal handle or orientation handle), and/or may be connected to the catheter by way of a catheter head. The wire spade may be connected to the catheter, may be configured to be deployed in a right ventricle of the heart, and may be configured to contact walls of the right ventricle and thereby stabilize the needle when the needle is used to penetrate the tissue/septum, e.g., stabilize the needle when the needle penetrates the septum between the right ventricle and the left ventricle and enters into the left ventricle. The wires spade may have a variety of shapes and branches. The wire spade may be connected to the catheter by way of a catheter head. The spade-shaped assembly may also comprise an inner needle (e.g., a second needle) disposed within an inner lumen of the first needle, the inner needle may be configured to be advanced out of a lumen of the first needle, across the left ventricle, and configured to puncture a posterior wall of the left ventricle after the first needle has passed through the septum. The spade-shaped assembly may also comprise an orientation handle located at a proximal end of the catheter configured to provide control of an angle between a tip of the needle and the catheter and/or the wire spade. In one exemplary embodiment, the first needle and/or second, inner needle may comprise a hollow tube having a multiplicity of slits (e.g., S-shaped slits, C-shaped slits, V-shaped slits, zig zag slits, straight slits, diagonal slits, parallel slits, and/or other types of slits) disposed along the full length or a portion of the length of the needle. The slits (e.g., S-shaped slits) may be configured to allow the first needle and/or second, inner needle to undergo sharp turns when delivered inside the catheter and then resume a straightened orientation when extended out from the catheter. The slits (e.g., S-shaped slits) may be further configured to provide rigidity to the first needle and/or second, inner needle. In one exemplary embodiment, the slits (e.g., S-shaped slits) are configured to allow the orientation of the first needle and/or second, inner needle to be changed by rotating a proximal end of the first needle and/or second, inner needle extending from the catheter.

In one exemplary embodiment, a trocar catheter (e.g., of an anchoring system) may comprise a cannula being generally elongate and having an interior lumen. The trocar catheter may also include a trocar disposed within the interior lumen and extending to a trocar distal tip comprising one or more surfaces configured to puncture the tissue (e.g., puncture the tissue during rotation of the trocar). A central lumen may pass through the trocar catheter (e.g., through the cannula and/or the trocar) and may be in fluid communication with one or more lateral ports disposed on the trocar distal tip. The central lumen and the one or more lateral ports may be configured for contrast injection. The trocar catheter may include a proximal handle comprising a plunger mechanism and an actuator configured to facilitate advancing the trocar distal tip beyond a distal end of the cannula during puncturing of the tissue. The plunger mechanism may be further configured to withdraw the trocar distal tip into the distal end of the cannula during uses other than puncturing the tissue.

In one exemplary embodiment, an introducer system/assembly comprises a needle catheter having an inner lumen and a beveled edge configured for puncturing tissue and comprises an introducer having a guidewire lumen and an atraumatic and/or blunt shape of its distal end. The introducer may be disposed within the inner lumen of the needle catheter with its atraumatic/blunt shaped distal end extending distally beyond the beveled edge of the needle catheter. A spring may be disposed within the catheter configured to maintain the atraumatic/blunt shape extending distally beyond the beveled edge during uses other than puncturing tissue. A guidewire may be inserted into or otherwise disposed within the guidewire lumen of the introducer, the guidewire may be deliverable while the introducer distal end is extended to protect nearby tissues from damage from the beveled edge of the needle catheter. In one exemplary embodiment, the introducer and the needle catheter are configured such that the atraumatic/blunt shaped distal end of the introducer may be locked into the distally extended position so as to enable pushing against tissue without the beveled edge of the needle catheter puncturing the tissue.

In one exemplary embodiment, a threaded introducer (e.g., of an anchoring system) comprises an elongate member having a proximal head and a distal end. Both the proximal head and the distal end may have atraumatic surface features so as to prevent damage to tissues during delivery of the threaded introducer. A central lumen may extend through the length of the threaded introducer, e.g., from the proximal head to the distal end. The central lumen in the region within the proximal head may be configured to receive a catheter, and the central lumen in the region within the distal end may be configured for injection of contrast fluid (e.g., for imaging procedures). At least one lateral port may be disposed on the distal end and be in fluid communication with the central lumen. A multiplicity of threads may be disposed along the length of the threaded introducer and configured to engage with tissue as the threaded introducer is threaded into the tissue so as to facilitate controlled advancement within a moving tissue (e.g., moving heart tissue).

In one exemplary embodiment, a suture cutter catheter comprises: a moving plate; a blade; and an inflatable balloon, wherein the suture cutter catheter may be configured such that inflation of the balloon causes the moving plate to move toward the blade. The suture cutter catheter may also comprise a spring that biases the moving plate in a direction away from the blade. The suture cutter catheter may also comprise a plastic positioning tube having a lumen through which a suture may be received, the positioning tube attached to the moving plate such that the positioning tube is configured to maintain the suture in a desired position for cutting the suture. Other features described with respect to suture cutter catheters herein may also be included.

In one exemplary embodiment, a catheter/device (e.g., a C-shaped catheter/device or puncture location catheter/device) for identifying a puncture site (e.g., on a wall of a heart) during medical treatment is capable of causing a bend/bulge in a wall of a heart. The catheter/device may comprise: a proximal handle; a positioning tube coupled with the proximal handle, the positioning tube may include an elongate portion and a curved portion, and these may be integral and/or connected together in a variety of ways, e.g., a proximal bend may be positioned between them or connect them. The curved portion may have a radius of curvature configured for extending around a portion of an organ or heart (e.g., around the left side of a heart). An elbow may be disposed at a distal end of the curved portion. The catheter/device may include a guide aligned with a longitudinal axis of the elongate portion, and may include a finger moveable relative to the guide. The elbow may be configured/designed such that the guide and/or finger are oriented and aligned with a longitudinal axis of the elongate portion. The device/catheter may also include an applicator disposed near the proximal handle, the applicator being connected to the finger via a connector that passes within a first lumen of the curved portion, such that the applicator can be manipulated to move the finger relative to the guide.

In one exemplary embodiment, alignment of the finger with the longitudinal axis of the elongate portion may be configured to help indicate a location and orientation of the finger near the posterior wall of the human heart. In one exemplary embodiment, a spring is configured to bias the finger in a retracted configuration such that a pressing force applied to the applicator compresses the spring and transitions the finger to an extended configuration, and wherein upon removal of the pressing force the spring automatically transitions the finger back to the retracted configuration. The positioning tube may comprise one or multiple lumens. A second lumen, different from the first lumen, may be configured for deploying an anchor at the puncture site during medical treatment. The catheter/device may be a C-shaped device/catheter or puncture location device/catheter as described elsewhere herein and may include any of the described features and be used in any of the described methods or steps.

BRIEF DESCRIPTION OF THE DRAWINGS

The drawings refer to embodiments of the present disclosure in which:

FIG. 23A is a perspective view of an exemplary embodiment of a C-shaped puncture location catheter/device suitable for use during medical treatment;

FIG. 23B is a side plan view of the exemplary embodiment of the C-shaped puncture location catheter/device illustrated in FIG. 23A; and FIG. 23C is a front plan view of the exemplary embodiment of the C-shaped puncture location catheter/device illustrated in FIG. 23A.

Figure 1A:
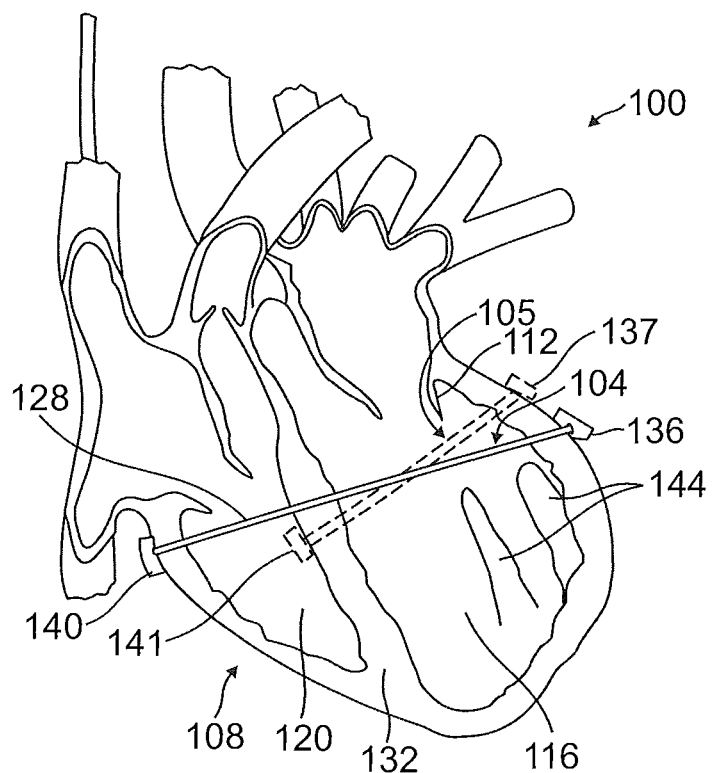
FIG. 1A is a vertical cross-sectional view of left and right ventricles of a human heart illustrating an orientation of an exemplary mitral valve splint; an optional (or alternative) mitral valve splint with one anchor against the septum of the heart is also shown in outline.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

Various aspects of the present disclosure generally relate to systems, assemblies, apparatuses, devices, and methods for medical treatment and/or treating heart conditions, including, by way of example, treating dilation/dilatation (including a dilated left ventricle), valve incompetencies (including mitral valve regurgitation), and other similar heart failure conditions. The systems, assemblies, apparatuses, devices, and methods are adapted for a transcatheter medical treatments that may not require full, open surgery, and can be minimally invasive. Each apparatus or device disclosed herein preferably operates passively in that, once placed in the heart, the device does not require an active stimulus, either mechanical, electrical, or otherwise, to function. Implanting one or more of the devices of the present disclosure operates to assist in an apposition of heart valve leaflets so as to improve valve function. In addition, the devices disclosed herein may either be placed in conjunction with other devices that, or may themselves function to, alter the shape or geometry of the heart, locally and/or globally, and thereby further increase the heart's efficiency. That is, the devices disclosed herein generally facilitate an increased pumping efficiency of the heart by way of an alteration in the heart's shape or geometry and concomitant reduction in stress on heart walls, and through an improvement in valve function.

The present disclosure offers numerous advantages over existing treatments for various heart conditions, including valve incompetencies. The devices disclosed herein are relatively easy to manufacture and use, and the surgical techniques and tools for implanting the devices of the present disclosure do not require the highly invasive procedures of current surgical techniques. For instance, the treatments described herein do not require removing portions of heart tissue, nor do they necessarily require opening the heart chamber or stopping the heart during operation. For these reasons, the treatments and techniques for implanting the devices of the present disclosure convey a reduced risk to the patient as compared with other techniques. The less invasive nature of the treatments and techniques and tools of the present disclosure may further allow for earlier intervention in patients with heart failure and/or valve incompetencies. While often discussed herein in terms of mitral valve treatments, the systems, devices, methods, etc. may be used to treat other heart valves, heart conditions, enlargement of other organs, etc.

In one embodiment, the present disclosure involves geometric reshaping of the heart and treating valve incompetencies. In certain aspects of the present disclosure, substantially an entire chamber geometry is altered so as to return the heart to a more normal state of stress. Models of this geometric reshaping, which includes a reduction in radius of curvature of the chamber walls, can be found in U.S. Pat. No. 5,961,440 incorporated above. Prior to reshaping the chamber geometry, the heart walls experience high stress due to a combination of both the relatively large increased diameter of the chamber and the thinning of the chamber wall. Filling pressures and systolic pressures are typically high as well, further increasing wall stress. Geometric reshaping according to the present disclosure reduces the stress in the walls of the heart chamber to increase the heart's pumping efficiency, as well as to stop further dilatation of the heart.

Although the present disclosure is discussed in connection with treating the mitral valve of the heart, the present disclosure may be applied to various chambers of the heart and for other valves of the heart for similar purposes. More broadly, the systems, apparatuses, methods, etc. disclosed herein may be used in other applications to change the geometries and/or stresses of other parts of the body (e.g., a stomach, bladder, or other part of the body). It also is contemplated that the present disclosure may be used to support an infarcted heart wall so as to prevent further dilatation, or to treat aneurysms in the heart. It is further contemplated that the present disclosure may be placed relative to the heart without altering the shape of the chamber, and only altering the shape of the valve itself.

In the following description, numerous specific details are set forth in order to provide a thorough understanding of the present disclosure. It will be apparent, however, to one of ordinary skill in the art that the invention disclosed herein may be practiced without these specific details. Thus, the specific details set forth are merely exemplary. The specific details may be varied from and still be contemplated to be within the spirit and scope of the present disclosure. In other instances, specific numeric references such as "first anchor" or "first needle" may be made. However, the specific numeric reference should not be interpreted as a literal sequential order but rather interpreted that the "first anchor" or "first needle" is different from a "second anchor" or "second needle." The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes systems, apparatuses, and related methods for medical treatment, e.g., for treatment of heart dilation and any associated functional mitral valve regurgitation within a human heart and/or for transcatheter treatment. In one embodiment, an anchoring system or system for setting an anchor and/or splint may comprise an anchor for fixating a mitral valve splint within the heart. In one exemplary embodiment, the anchor may comprise a cover supported by a ring so as to assume a generally circular or disc-shaped configuration or other configuration to contact an exterior surface of the heart, the myocardium, or the pericardium. The system may include an ultrasound probe for imaging parts of the system and parts of the body to be treated. The ultrasound probe may include a guide attached thereto for guiding various components/instruments of the system during treatment. The system may include a stabilizing assembly (e.g., a spade-shaped assembly) configured to be deployed in a right ventricle of the heart and to stabilize a catheter and/or assembly during penetrating the septum. The stabilizing assembly may include various components including one or more of a catheter, catheter head, stabilizing wire or structure (e.g., a spade-shaped wire), a curved needle, and an inner needle. A curved, bent, or bendable needle may be loaded in the catheter as part of the spade-shaped assembly and may be configured to penetrate a septum (e.g., the septum between the right ventricle and the left ventricle). Optionally, even if the stabilizing assembly is not used, a curved, bent, or bendable needle/catheter may still be used in essentially the same methods. The curved, bent, or bendable needle/catheter may comprise a hollow tube having a multiplicity of slits (e.g., S-shaped slits, C-shaped slits, V-shaped slits, zig zag slits, straight slits, parallel slits, diagonal slits, etc.) disposed along the length of the needle. The slits (e.g., S-shaped slits) allow the needle to undergo sharp turns within the heart. The curved, bent, or bendable needle may be configured to deploy an inner needle (or other device) from a lumen of the curved, bent, or bendable needle and into the left ventricle. The system may include a trocar catheter configured for puncturing body tissue (e.g., heart tissue) without damaging other nearby tissue.

The anchoring system or system for setting an anchor and/or splint may include an introducer system or introducer assembly for interventional cardiology procedures that may comprise an atraumatic/blunt shape introducer inside a needle catheter to protect nearby tissue within the heart during advancing a guidewire or other instrument through a lumen of the introducer. The system may include a threaded introducer, which may act as a temporary anchor and may be configured for advancing a guidewire and/or other instruments (e.g., the anchor or a delivery catheter including the anchor) through a moving tissue, such as a beating heart. In an exemplary embodiment, the threaded introducer comprises a multiplicity of threads disposed along the length of the threaded introducer and configured to rotatably engage with a tissue so as to facilitate advancing within the moving tissue as the threaded introducer is rotated—the treaded catheter may enable the user to control the depth of the tip of the threaded catheter in a moving organ (e.g., myocardium of a beating heart). The system may include a suture cutter catheter for cutting sutures in a remote, difficult to access location, e.g., inside the heart or on a wall of the heart. The system may also include an ultrasound probe (e.g., a trans-vaginal ultrasound probe or other ultrasound probe may be used) for imaging parts of the system and parts of the body to be treated. The ultrasound probe may include a guide attached thereto for guiding various components/ instruments of the system during treatment.

FIGS. 1A-2B illustrate an exemplary treatment area/ environment 100 wherein a mitral valve splint is placed within a human heart 108. In FIGS. 1A and 1B, an exemplary mitral valve splint 104 is placed within a human heart 108 so as to lessen myocardial muscular stresses and treat leaflet apposition of a mitral valve 112, as discussed herein. FIG. 1A is a vertical cross-sectional view of left ventricle 116 and right ventricle 120 of the heart 108 illustrating an exemplary orientation of the MV splint 104 within the heart 108. An alternative MV splint 105 is shown in outline. MV splint 105 may be similar to MV splint 104 or different, but MV splint 105 is positioned with an anchor 141 against the septum 132 of the heart instead of outside the heart like anchor 140. The exact placement and orientation of MV splint 104 and MV splint 105 and their components may vary; the placements and orientations shown in FIGS. 1A-2B are non-limiting examples. Optionally, more than one MV splint 104 could be used simultaneously at different locations of the heart for variations on the treatment.

Figure 1B:
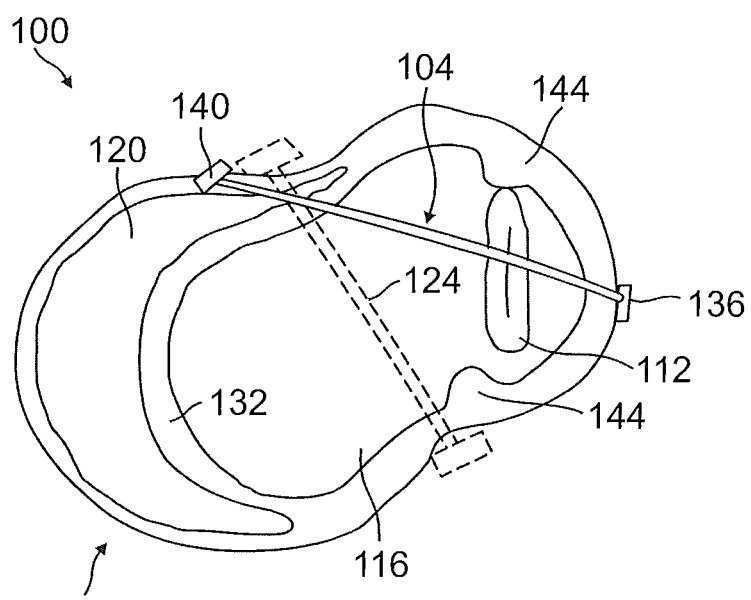
FIG. 1B is a transverse cross-sectional view of the left and right ventricles illustrating an orientation of an exemplary mitral valve splint used in combination with a transventricular splint for lessening myocardial muscular stresses and assisting in apposition of valve leaflets.

FIG. 1B shows a transverse cross-sectional view of the left and right ventricles 116, 120 illustrating an orientation of the MV splint 104 used in combination with a transventricular splint 124 (shown in outline, but may be used simultaneously with MV splint 104 or other splints described herein) for lessening myocardial muscular stresses and assisting in apposition of valve leaflets.

Figure 2A:
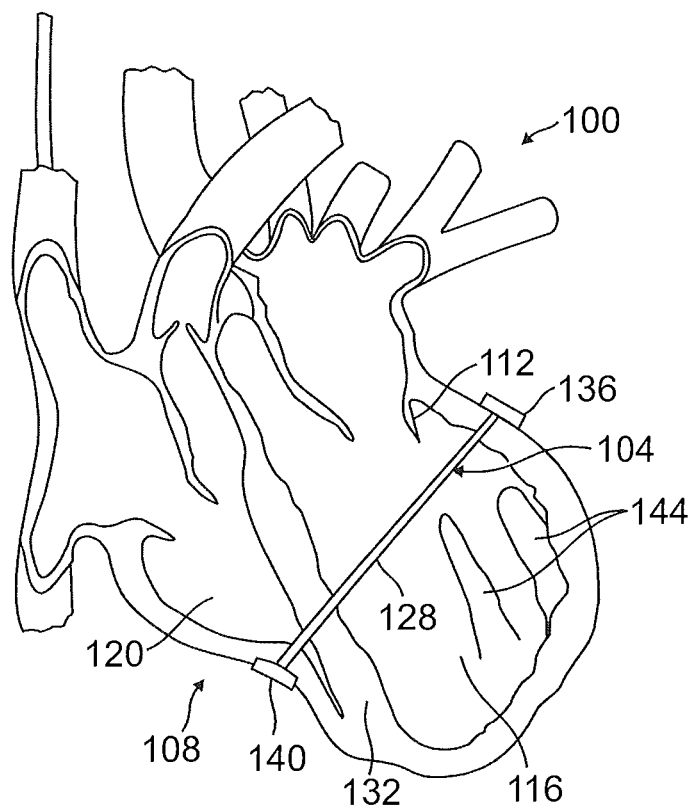
FIG. 2A is a vertical cross-sectional view of left and right ventricles of a human heart illustrating another possible orientation of an exemplary mitral valve splint.
Figure 2B:
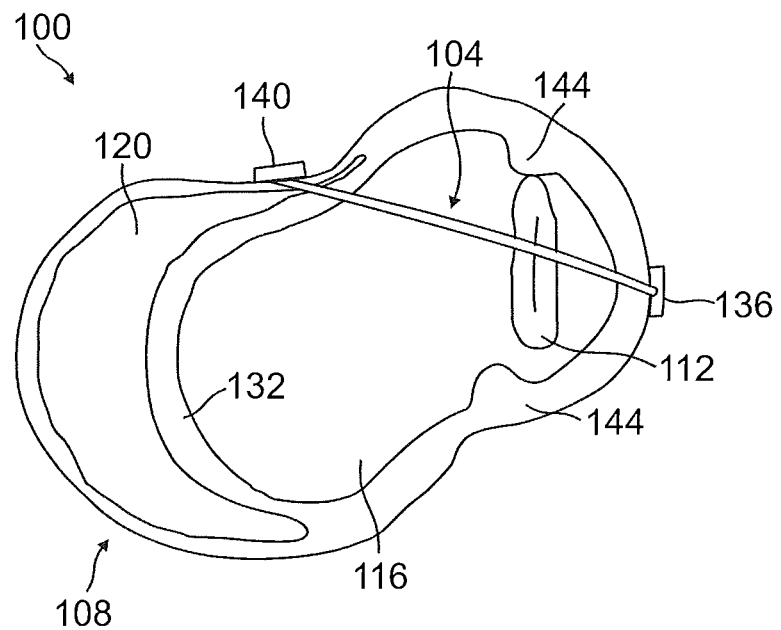
FIG. 2B is a transverse cross-sectional view of the left and right ventricles illustrating an orientation of an exemplary mitral valve splint, which may be the same as or similar to that shown in FIG. 2A.

FIGS. 2A-2B illustrate another possible orientation and placement of mitral valve splint 104 within a human heart 108 so as to lessen myocardial muscular stresses and treat leaflet apposition of a mitral valve 112, as discussed herein. FIG. 2A is a vertical cross-sectional view of left ventricle 116 and right ventricle 120 of the heart 108 illustrating an exemplary orientation of the MV splint 104 within the heart 108. FIG. 2B shows a transverse cross-sectional view of the left and right ventricles 116, 120 illustrating an orientation of the MV splint 104. Because the wall of the right ventricle is generally thinner than the wall of the left ventricle and because the blood pressure in the right ventricle is generally lower than in the left ventricle, when force is applied to the right ventricle heart wall (e.g., when the MV splint 104 is tensioned pulling anchors 136 and 140 toward each other), the wall or a portion of the wall of the right ventricle may be compressed inwardly or deformed, e.g., as shown in FIGS. 2A and 2B, and may even be pushed into contact with septum 132. A lower placement of anchor 140 along the right ventricle wall as shown in FIG. 2A may reduce issues associated with collapsing the right ventricle wall inwardly (e.g., this can leave the upper half of the right ventricle functioning normally or better than if the upper portion of the right ventricle was more collapsed).

A superior anchor 136 is disposed at a first end of the tension member 128 and positioned adjacent to the left ventricle 116. An inferior anchor 140 is disposed at a second end of the tension member 128 and may be positioned adjacent to the right ventricle 120 (e.g., external to the heart outside the right ventricle as shown in FIGS. 1-2) or may be positioned inside the right ventricle against a wall of the septum 132. Tension member 128 of the MV splint 104 extends from anchor 140 across the right ventricle 120, through the septum 132, and across the left ventricle 116 of the heart to anchor 136. A primary function of the MV splint 104 is to impart a shape change to an annulus of the mitral valve 112, as well as advantageously reposition papillary muscles 144. As such, the tension member 128 may extend through the heart 108 superior to the papillary muscles 144 and may be oriented primarily across the mitral valve 112 and on or below the mitral valve annulus while avoiding key vascular structures. Further details regarding specific treatments for lessening myocardial muscular stresses and leaflet apposition of the mitral valve, as well as devices and methods for delivering mitral valve splints, are disclosed in U.S. Pat. No. 7,766,812, incorporated herein above.

Figure 3A:
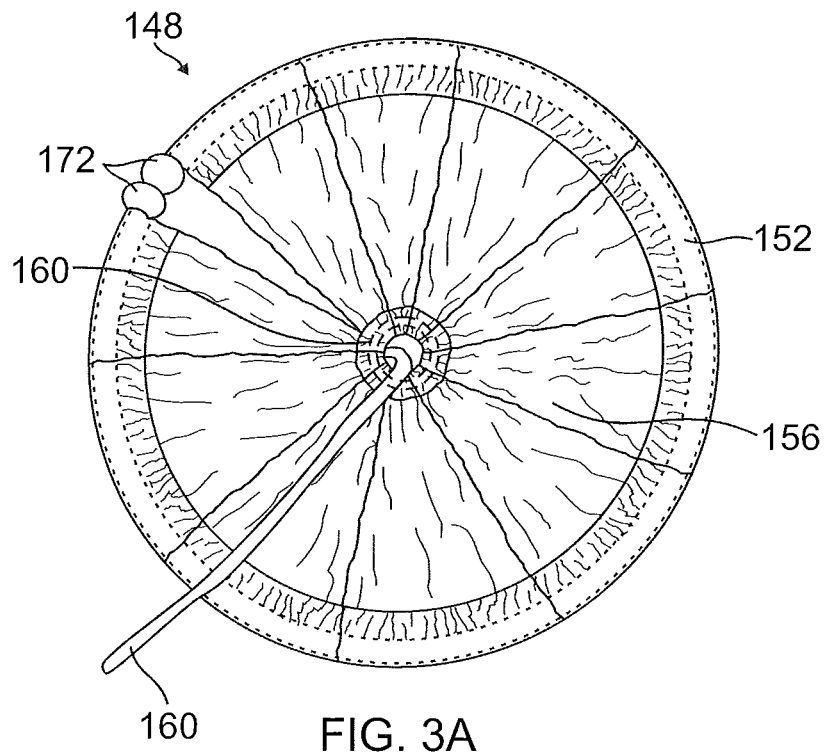
FIG. 3A illustrates an exemplary embodiment of a self-expandable anchor suitable for anchoring a mitral valve splint, the anchor having a ring in a circular configuration and a cover in a disc-shaped configuration.
Figure 3B:
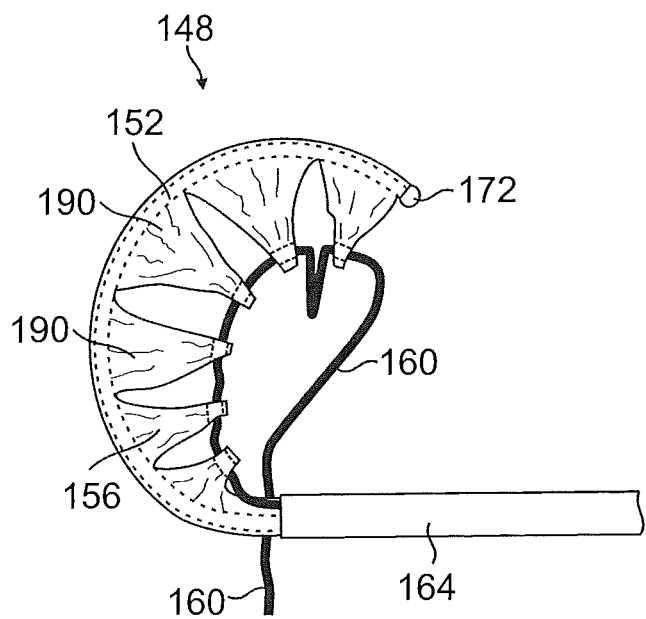
FIG. 3B illustrates the self-expandable anchor of FIG. 3A transitioning between a straightened, low-profile configuration inside a catheter and a deployed configuration.

FIGS. 3A-3B illustrate an exemplary embodiment of a self-expandable anchor 148 suitable for fixating the MV splint 104 within the heart 108, e.g., as described above. The self-expandable anchor 148 may comprise a ring 152 which may peripherally support a cover 156. Upon cinching a centrally disposed tension member or cord 160, the cover 156 can assume a circular, flattened, disc-shaped, or pie-shaped configuration as shown in FIG. 3A, e.g., when the interior ends of the tabs 188 are pulled toward the center, or can assume a cone shaped configuration if the ends of the tabs 188 are pulled in a direction perpendicular to a plane aligned with the ring 152, e.g., when the tension member pulls the anchor toward another anchor.

It is contemplated that the self-expandable anchor 148 may be utilized for either or both of the superior and inferior anchors 136, 140. Optionally, different types of anchors may be used for the superior and inferior anchors (e.g., any of the anchors described in this disclosure or other types of anchors). A cover may or may not be used on one or both of the superior and inferior anchor. As will be appreciated, the deployed or expanded configuration (e.g., circular/disc-shaped/pie-shaped/cone-shaped configuration) of the self-expandable anchor 148 shown in FIGS. 3A-3B is well suited for anchoring the tension member 128 in position within the heart 108, as well as withstanding the forces encountered during changing the shape of the heart 108, as described above. In one embodiment, the deployed or expanded configuration (e.g., circular, disc-shaped, pie-shaped, or cone-shaped configuration) of the anchor 148 (or other anchors described elsewhere herein) may provide a surface area of substantially 4 $cm^2$, which effectively eliminates migration of the anchor into the tissue of the heart 108. Optionally, the surface area may be between 2 $cm^2$ and 6 $cm^2$ or between 3 $cm^2$ and 5 $cm^2$, though other sizes are also possible. Further, the anchor 148 may preferably be configured to withstand forces due to tension within the tension member 128 of up to substantially 17 Newtons (N). A larger surface area helps the anchor withstand higher forces. For example, the embodiment shown in FIGS. 3A-3B can withstand forces of 17 Newtons with a surface area of 4 $cm^2$. As will be appreciated, the relatively large surface area of the cover 156 coupled with the centrally disposed tension member 160 provide an inherently stable configuration of the self-expandable anchor 148, thereby eliminating mechanical failures and migration into the tissue as encountered with other anchors. Further, the large surface area of the cover 156 and the centrally disposed tension member 160 cooperatively operate as a closure device which seals the punctures in the walls of the heart 108. In some embodiments, the cover 156 may be coupled with an additional sealing component to further prevent bleeding through the puncture site. The cover may be formed of a material that allows tissue ingrowth into the material after implantation. Further, the cover may be formed to assume a generally cone-shaped configuration when placed under tension so as to inhibit migration of the anchor during beating of the heart (a cone shape is believed to be more stable, in terms of migration, than a flat shape).

As can be seen in FIGS. 3A-3B, the anchor 148 may transition between a deployed or expanded configuration (e.g., circular/disc-shaped/pie-shaped/cone-shaped configuration) and a collapsed or low-profile configuration (e.g., a straightened configuration) whereby the anchor may be loaded into a delivery catheter. As can be seen in FIG. 3B, the tension member 160 may be loosened to allow the cover 156 to change from the deployed or expanded configuration (e.g., flattened/disc-shaped/pie-shaped/cone-shaped configuration) to a collapsed or low-profile configuration whereby the cover may be folded or compressed against the ring 152. Upon extending or changing the ring 152 from a circular or ring-shaped configuration to a straightened configuration (and optionally folding the cover against the ring), the self-expandable anchor 148 may be loaded into a lumen of a catheter 164 for delivery, (e.g., into the heart 108). During delivery of the superior anchor 136 (e.g., anchor 148), the delivery catheter 164 may be pushed through the walls of the heart 108 and navigated to a suitable location outside of the left ventricle 116. Some of the steps disclosed in U.S. Pat. No. 7,766,812, incorporated above, might also be used. Upon pushing the self-expandable anchor 148 out of the lumen of the delivery catheter 164, the ring 152 automatically changes from the straightened or low-profile configuration to a deployed or expanded configuration (e.g., a circular configuration), as shown in FIG. 3B, in which the anchor 148 is transitioning between a low-profile configuration in the catheter 164 and a delivery, deployed, or expanded configuration.

After initial deployment of the anchor 148 from the catheter 164, the tension member or cord 160 may be pulled, which then draws the central portion of the cover 156 taut toward the center of the ring 152, thereby producing the deployed or expanded configuration (e.g., a circular, flattened configuration, a somewhat convex or cone like configuration, or the disc-shaped/pie-shaped configuration of the cover shown in FIG. 3A). Tightening the tension member 160 pulls the self-expandable anchor 148 against the exterior surface of the heart wall, the myocardium, or the pericardium, such that the cover 156 assumes a convex or cone shape pressing against the surface and extending inward with the tension member 160 passing through the puncture in the heart wall. As the tension member may pull perpendicularly, generally perpendicularly (e.g., within 5 degrees of perpendicular), or at an angle away from a plane with which the ring of the deployed anchor is aligned (e.g., a circle of the ring is in the plane). A similar procedure may be utilized for deploying the self-expandable anchor 148 as the inferior anchor 140; however, the side of the heart having the inferior anchor is more easily accessible and a wider variety of anchors and procedures for deploying and securing the inferior anchor 140 may be used, e.g., the inferior anchor 140 may not need to assume as low a profile because it will not cross through the heart. In some embodiments, the tension member 160 passing between the superior and inferior anchors 136, 140 may comprise the tension member 128 shown in FIG. 1. Upon sufficiently tightening the tension member 160, one or more of the anchors 136, 140 may be drawn into convex cone shapes that point inward or toward each other so as to suitably reshape the heart 108. The tension members described herein may be cords, wires, cables, etc. and may be rigid, semi-rigid, or flexible and may be elastic or non-elastic. An elastic tension member may allow some give (e.g., expansion and contraction) during movement or beating of the heart, whereas a non-elastic tension member may maintain the same or substantially the same relative distance between the superior and inferior anchors. The tension members may optionally be braided or include a braided portion. The tension members may be formed of a high strength/high performance polymers, e.g., UHMWPE, etc.

Figure 4A:
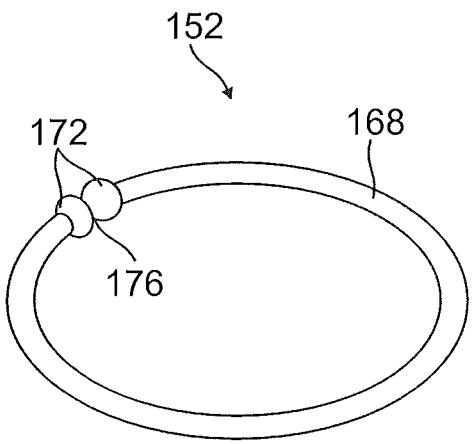
FIG. 4A is a perspective view illustrating an exemplary embodiment of a ring which may be incorporated into a self-expandable anchor.
Figure 4B:
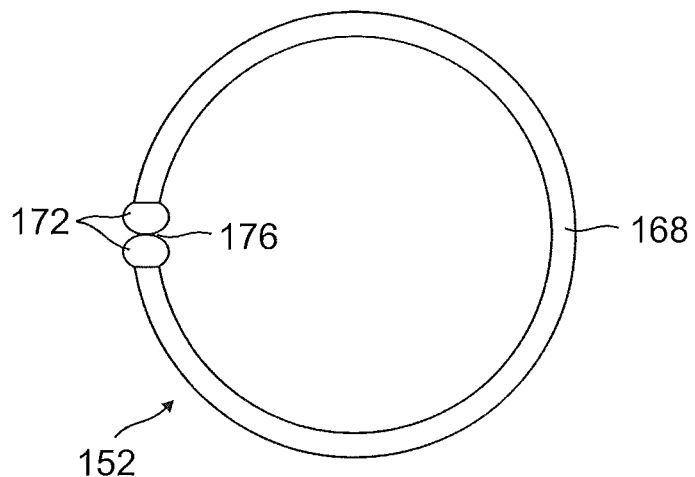
FIG. 4B is a top view illustrating the exemplary embodiment of the ring illustrated in FIG. 4A.
Figure 4C:
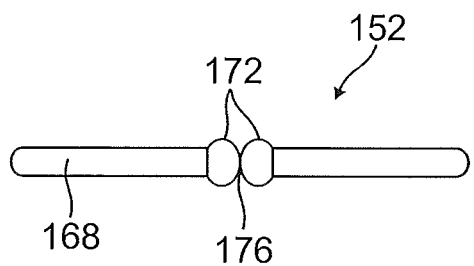
FIG. 4C is a side view illustrating the exemplary embodiment of the ring illustrated in FIG. 4A.

FIGS. 4A-4C illustrate an exemplary embodiment of the ring 152, which may be incorporated into the self-expandable anchor 148, in accordance with the present disclosure. The ring 152 comprises a circularly configured wire 168 having atraumatic ends 172 which meet at a break 176. As will be appreciated, the break 176 facilitates expanding the ring 152 into the low-profile configuration or straightened configuration suitable for loading the ring 152 into the lumen of the delivery catheter 164, as discussed above. The wire 168 may comprise or consist of a shape memory material (e.g., nitinol or another shape memory alloy) suitable for returning the ring 152 from the low-profile configuration (e.g., straightened configuration) to the circular configuration shown in FIG. 4A. It is contemplated, however, that various other suitably shape memory or elastic materials may be used for the wire 168 without limitation, and without deviating beyond the spirit and scope of the present disclosure. In one embodiment, the ring 152 may be formed of stainless steel. Ring 152 may be of different sizes, diameters, and shapes. Similarly, the wire 168 may be of different sizes, diameters, and shapes, including in the cross-sectional size/shape of the wire 168. Optionally, the ring may be circular, oval, ovoid, flower shaped, star shaped, square, rectangular, pentagonal, hexagonal, decagonal, spiral, helical, and/or other shapes. Also, while ring 152 is shown having a circular cross-sectional shape, other cross sectional shapes are possible, e.g., oval, ovoid, triangular, square, rectangular, pentagonal, hexagonal, decagonal, etc.

The atraumatic ends 172 prevent the ends of the ring 168 from otherwise damaging the delivery catheter, the tissues of the heart 108, or other nearby body tissues during delivery and deployment of the self-expanding anchor 148. Further, the atraumatic ends 172 facilitate loading the self-expanding anchor 148 into the interior lumen of the catheter 164. In one embodiment illustrated in FIGS. 4A-4C, the atraumatic ends 172 comprise spherical portions or balls at the ends of the wire 168. In one embodiment, the atraumatic ends 172 may be comprised of any of various other suitably shaped portions as may be deemed appropriate; for example, other shapes/configurations for the atraumatic ends 172 is also possible, e.g., cube-shaped, ovoid shaped, oval shaped, etc. In one embodiment, the atraumatic ends 172 comprise portions of the ends of the wire 168 that are formed into spherical, generally spherical, ellipsoid, and/or ovoid portions. In one embodiment, the atraumatic ends 172 may be comprised of separate components that are fastened onto the ends of the wire 168. As will be appreciated, any of various techniques may be used to fasten the atraumatic ends 172 onto the ends of the wire 168 without limitation.

Figure 4D:
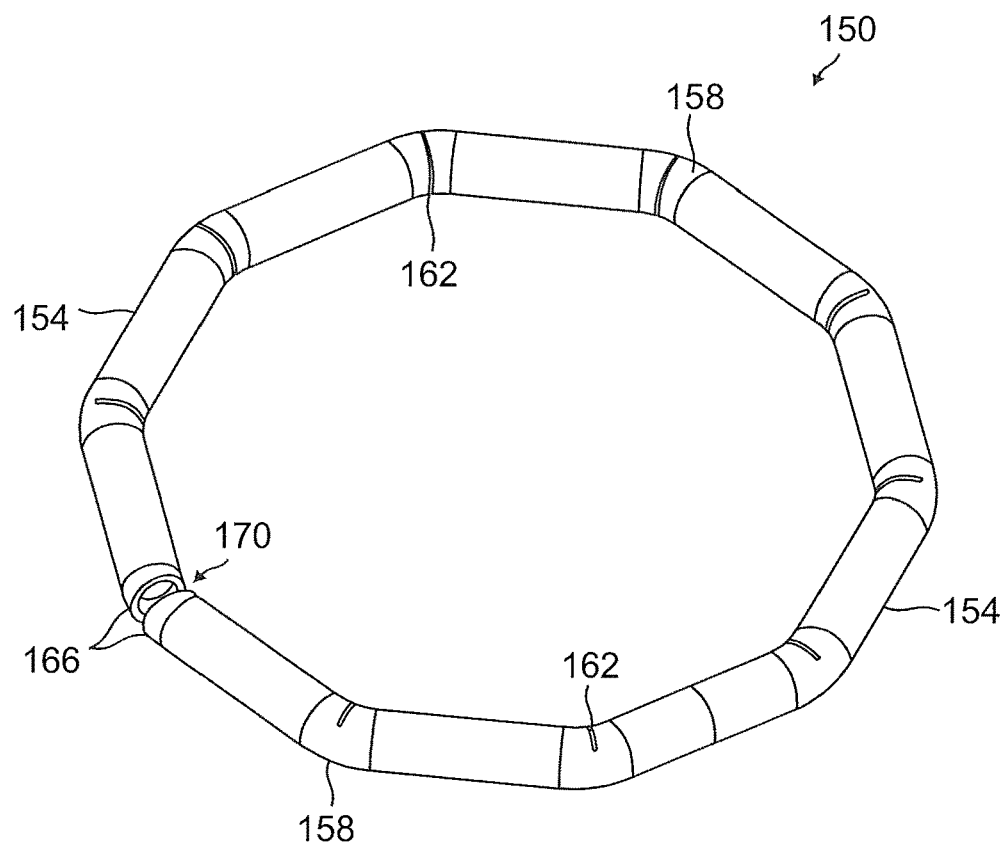
FIG. 4D is an isometric view illustrating an exemplary embodiment of a notched tube in a circular configuration that may be used as part of an expandable anchor.
Figure 4E:
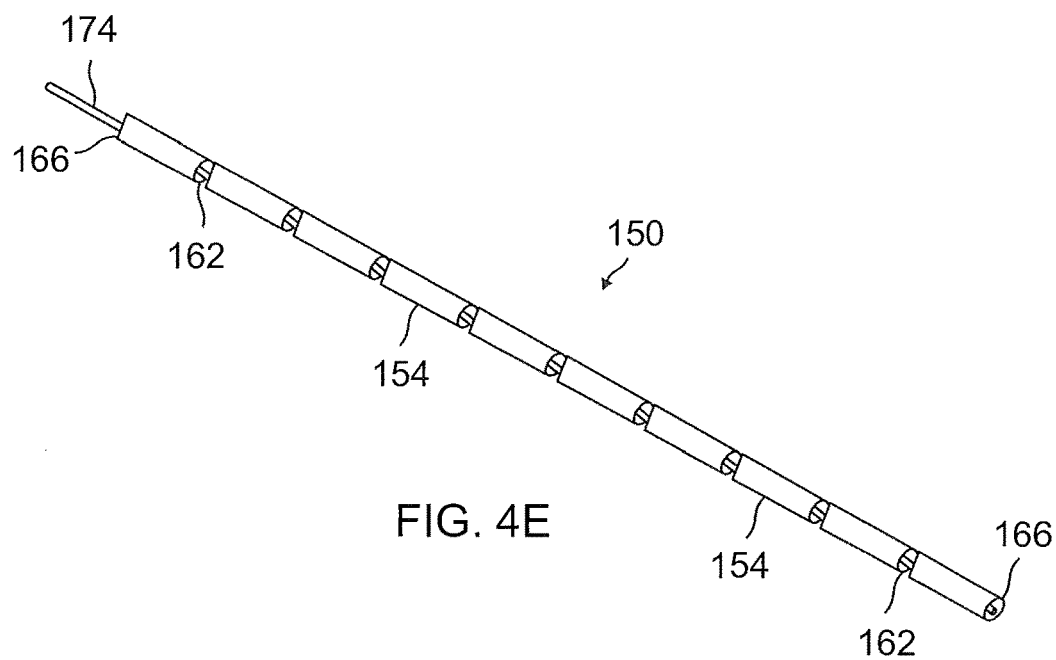
FIG. 4E is a perspective view illustrating the notched tube of FIG. 4D in a straightened, low profile configuration suitable for positioning inside a catheter.

FIGS. 4D-4E illustrate an exemplary embodiment of a notched tube 150 that may be incorporated into a manually expandable anchor (i.e., not self-expandable) that may be configured to operate similarly to the above-discussed anchor 148. In a straight, low-profile configuration, shown in FIG. 4E, the notched tube 150 may comprise a multiplicity of notches 162, or cut-out portions, disposed along the length of the tube, such that the notched tube 150 comprises a series of straight and unbroken sections 154. Each of the notches 162 may be wedge-shaped or comprise a wedge-shaped portion extending partially across the diameter of the tube so as to enable bending adjacent straight sections 154 toward one another. The multiplicity of notches 162 may enable the notched tube 150 to be pulled or transitioned from a low profile configuration (e.g., straightened or flattened configuration) as shown in FIG. 4E to an expanded or deployed configuration (e.g., a circular, ring-like, or decagonal, etc. configuration as shown in FIG. 4D).

A wire, member, or cable 174 disposed within a lumen of the notched tube 150 may enable changing the tube from a low-profile configuration (e.g., straight or flattened configuration) as shown, for example, in FIG. 4E to an expanded configuration (e.g., a circular, ring-like, decagonal, etc. configuration) as shown, for example, in FIG. 4D. In the deployed or expanded configuration (e.g., a circular, ring-like, decagonal, etc. configuration), the notches 162 may be substantially closed (e.g., with adjacent faces of wedge shaped notches brought close together or in contact) and each pair of adjacent straight sections 154 may be disposed at an angle with respect to one another and share an intervening bend 158. It is contemplated that the overall diameter of the notched tube 150 in the circular configuration may depend upon the number and length of straight sections 154, the number of notches 162 disposed along the tube, and the depth to which the notches 162 extend across the diameter of the tube. It should be understood that the number and length of straight sections 154, and the number and depth of the notches 162 may be varied without limitation.

The notched tube 150 may comprise atraumatic ends 166. The atraumatic ends 166 may be configured to prevent the ends of the notched tube 150 from damaging a delivery catheter, the tissues of the heart 108, or other nearby body tissues during delivery and deployment of the notched tube 150 to an anchor site, as described herein. The atraumatic ends 166 further facilitate loading the notched tube 150 into the interior lumen of a catheter, such as, for example, the catheter 164. In one embodiment, the atraumatic ends 166 may be comprised of smooth, rounded edges of the notched tube 150. In one embodiment, the atraumatic ends 166 may be comprised of any of various suitably shaped portions as may be deemed appropriate; for example, other shapes/configurations for the atraumatic ends 166 may be comprised of spherical portions, balls, cube-shaped, ovoid shaped, oval shaped, etc. In one embodiment, the atraumatic ends 166 may comprise portions of the ends of the notched tube 150 that are formed into spherical, generally spherical, ellipsoid, and/or ovoid portions. In one embodiment, the atraumatic ends 166 may be comprised of separate components that are fastened onto the ends of the notched tube 150. Any of various techniques may be used to fasten the atraumatic ends 166 onto the ends of the notched tube 150 without limitation. In the deployed or expanded configuration (e.g., as shown in FIG. 4D), the atraumatic ends 166 may meet at a break 170.

Figure 5A:
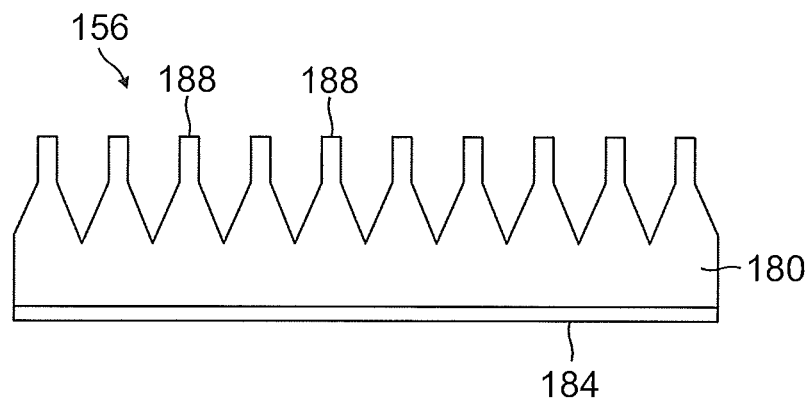
FIG. 5A is a top view illustrating an exemplary embodiment of a cover in an open, unfolded configuration which may be incorporated into a self-expandable anchor.
Figure 5B:
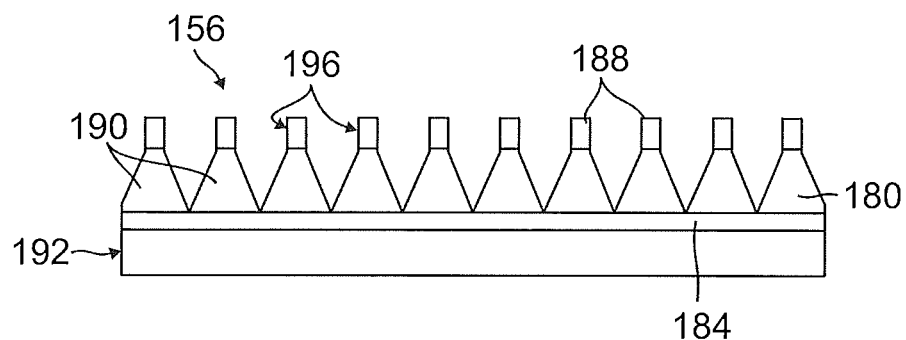
FIG. 5B is a top view illustrating the exemplary embodiment of the cover illustrated in FIG. 5A in a folded configuration.
Figure 5C:
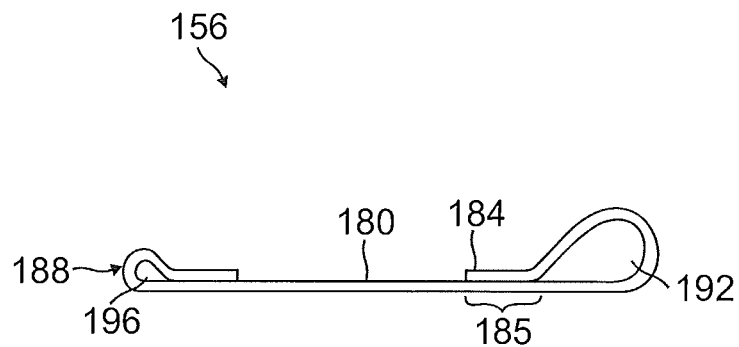
FIG. 5C is a side view illustrating the exemplary embodiment of the cover of FIG. 5A in the folded configuration.

FIGS. 5A-5C illustrate an exemplary embodiment of the cover 156 which may be incorporated into the self-expandable anchor 148, according to the present disclosure. FIG. 5A illustrates the cover 156 in an open, unfolded configuration wherein the cover 156 is comprised of a strip 180 of suitable material having a first, straight edge 184 and a second edge comprising a series of tabs 188. An intermediate portion of strip 180 may include triangular or wedge shaped portions 190 that work together to fill the center of the anchor, e.g., in pie-shaped slices. The triangular or wedge-shaped portions 190 can help prevent excessive material in the center of the anchor and, thus, help prevent excessive folding or bunching of the material when in the anchor's fully deployed configuration. This may also help the anchor and cover assume a more flattened configuration. Other shapes and designs for the cover are also possible. For example, the cover may have a larger, unbroken surface area (e.g., cover 156 may not have as many tabs, triangular or wedge shaped portions, or spaces as shown in FIGS. 3A & 5B). Cover 156 may be constructed of a thick material or a thin material, and may fill all or a portion of the center of the anchor. The material comprising the strip 180 may be formed of one or more of any of various polymer materials, such as polyethylene terephthalate (PET), ultra-high-molecular-weight polyethylene (UHMWPE), and/or other similar material. In one embodiment, the strip 180 may comprise one or more of any of a wide variety of suitable metallic materials. In one embodiment, the strip 180 may comprise a non-metallic material, such as by way of non-limiting example, carbon fibers and the like. Various combinations of the above materials may also be used.

As illustrated in FIGS. 5B-5C, portions of the strip 180 may be folded and secured such that loops are formed through which the ring or tension member may be threaded to form the anchor. For example, the straight edge 184 may be folded onto (e.g., to overlap) a mid-region of the strip 180 to form an overlapping region 185 in which the edge 184 is attached/adhered/sewn to a portion of the mid-region and to form a passage 192 extending along the length of the straight edge. Similarly, each tab 188 may be folded over to form a loop 196. As best illustrated in FIG. 5C, the passage 192 comprises a diameter suitable to receive the ring 152, and the loops 196 comprise a diameter suitable for receiving the tension member 160. Optionally, a similar cover, similar strips, or portions/segments of a cover could be formed from double lumen cloth (e.g., that may come with a small lumen/passage on one end and a larger lumen/passage on the other end), or from tube-shaped cloth. If tube shaped cloth is used, it could be flattened with sutures but leave lumens/passages on the ends and could result in the same or a similar shape. Double lumen cloth or tube shaped cloth could be much stronger than a cloth end that is folded and adhered/attached, because the adhesion or attachment could be weakened or be more likely to open.

The self-expandable anchor 148 may be formed by mounting the cover 156 onto the ring 152 by way of threading the ring 152 through the passage 192, and by threading or weaving the tension member 160 through all of the loops 196. The tension member may optionally be tied to itself in a slip knot or similar adjustable knot that allows the tension member to cinch the loops 196 toward the center of the ring. Optionally, after passing through the loops 196, each end of the tension member may extend to a proximal end of the delivery catheter and pulling at one or both ends may cinch the loops 196 toward the center of the ring. As will be appreciated, upon loosening the tension member 160 within the loops 196, the strip 180 facilitates expanding or transitioning the ring 152 from a deployed or expanded configuration (e.g., a circular or ring-shaped configuration) into a low profile configuration (e.g., straightened configuration), as discussed above, and thus enables the self-expandable anchor 148 to be suitably loaded into the lumen of the catheter 164.

Figure 6A:
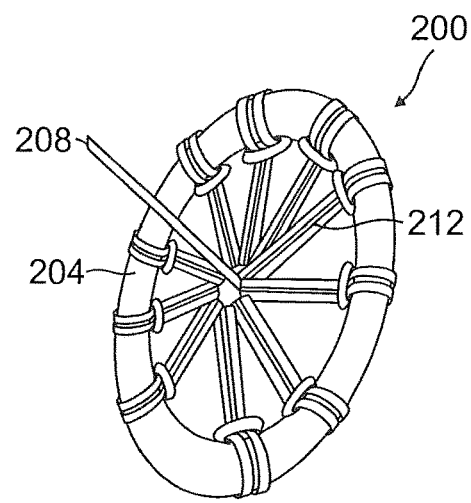
FIG. 6A illustrates an exemplary embodiment of an anchor comprising a ring attached to a tension member by way of a multiplicity of spokes.

It should be recognized, however, that the anchor 148 need not be limited to the ring 152 and cover 156, but rather various other configurations of anchors are contemplated within the scope and spirit of the present disclosure. For example, FIGS. 6A-11B illustrate various exemplary embodiments of anchors according to the present disclosure. In particular, FIG. 6A illustrates an exemplary embodiment of an anchor 200 comprising a ring 204 attached to a tension member 208 by way of a multiplicity of spokes 212. The ring 204 may include features the same as or similar to ring 152 (including having a break and atraumatic ends, and being transitionable to a low profile or a straightened configuration) described above and/or may include different design features or characteristics (e.g., forming an unbroken ring). If the ring 204 includes a break, it may be delivered in the same or a similar way to ring 152 as described above and elsewhere herein. If formed as an unbroken ring, the ring 204 may be capable of having two sides collapsed together to form a narrow or low profile of the anchor that may be inserted in a delivery catheter, and may be deployed out of a delivery catheter.

Ring 204 is depicted in FIG. 6A as having a larger cross-sectional size than ring 152, but other sizes are also possible, including sizes with a cross-sectional diameter less than ring 152. Also, while ring 204 is shown having a circular cross-sectional shape, other cross sectional shapes are possible, e.g., oval, ovoid, triangular, square, rectangular, pentagonal, hexagonal, etc. In one embodiment, ring 204 may be configured as a cylinder or cylindrical ring. During use, pulling the tension member 208 may place the cylinder or cylindrical ring in contact with the exterior surface of the heart 108, the myocardium, or pericardium while the tension member 208 passes through the center of the cylinder or cylindrical ring and the puncture in the heart wall, as described above.

While spokes 212 are depicted in place of a cover in FIG. 6A, a cover may also be used (e.g., to cover the ring and spokes or to cover a portion of the ring and spokes), or a cover may be used instead of the spokes 212. The cover may be the same as or similar to the cover 156 described above and/or may be constructed of a similar material to cover 156. Optionally, the cover may have a larger, unbroken surface area (e.g., the cover may not have any many tabs, triangular or wedge shaped portions, or spaces between tabs as cover 156). In one embodiment, the cover may be an unbroken material that covers the entire ring and/or any spokes, or the cover may be unbroken except for a hole in its center to allow tension member 208 to pass therethrough. The cover may be constructed of a thick material or a thin material, and may fill all or a portion of the center of the anchor. The cover may be disc-shaped, pie-shaped, or another shape, and may be broken or unbroken. The cover may connect ring 204 to tension member 208.

The tension member 208 may include features the same as or similar to tension member 160 described above and/or may include different design features or characteristics. The spokes 212 may comprise short segments of cord, wire, ribbon, or other material that are tied to the ring 204 and the tension member 208. The material of the spokes may be the same as that used for the cover 156 or tensioning member 160, and may be PET, UHMWPE, PTFE, ePTFE, or other suitable polymers or materials. More or fewer spokes may be used than are shown in FIG. 6A. In one embodiment, 3, 4, 5, 6, 7, 8, 9, 10, 11, or 12 spokes may be used. Anchor 200 may additionally (or, optionally, as an alternative to the spokes) include ribbons of a material woven and/or attached to the ring 204 and/or the spokes 212. The ribbons of material may provide a greater contact surface area and may provide additional strength and ability for the anchor to withstand high tension forces, e.g., when implanted. The ribbons of material may be similar to ribbons 308 shown in FIG. 6C. The ribbons of material may be formed of PET, UHMWPE, PTFE, ePTFE, or other suitable polymers or materials. Operation of the anchor 200 may be similar to the operation of the self-expandable anchor 148, but tightening the tension member 208 cinches the spokes 212 toward the center of the ring and draws the anchor 200 against the exterior surface of the heart 108.

Optionally, an inner ring or hub may be used near the center of the ring 204, and spokes 212 may extend and attach between the ring 204 and the inner ring or hub. During deployment of the anchor, pulling the tension member may cause the inner ring or hub, the spokes 212, and the ring 204 to lay against the exterior+– surface of the heart 108, as described herein. The inner ring or hub may be constructed of a material the same as or similar to those used for the ring 152 or the tension member 160 or may be constructed of a different material (e.g., may be a metal or steel ring). The spokes may wrap around or through the ring or may be otherwise attached/connected.

Figure 6B:
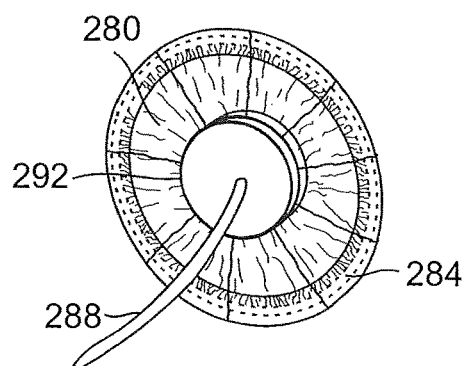
FIG. 6B illustrates an exemplary embodiment of an anchor comprising a circular cover mounted onto a ring.

FIG. 6B illustrates an exemplary embodiment of an anchor 276, according to the present disclosure. The anchor 276 comprises a cover 280 disposed over a ring 284. A tension member 288 may be connected to the cover 280 and/or the ring 284. The ring 284 may include features the same as or similar to one or more of the other rings (e.g., rings 152, 204) described herein. The cover 280 may include features the same as or similar to one or more of the other covers described herein (e.g., cover 156). The tension member 288 may include features the same as or similar to one or more of the other tension members described herein (e.g., tension members 160, 208). The anchor 276 may include a central anchor or hub 292. The circular cover 280 may be attached to tension member 288 by way of central anchor or hub 292. The anchor 276 may function similarly to the self-expandable anchor 148 or anchor 200. Pulling the tension member or cord 288 may place the circular cover 280 and the ring 284 into contact with an exterior surface of the heart 108, the myocardium, or pericardium. Among other things, the central anchor or hub 292 may provide additional support and may help seal the puncture in the exterior surface or wall of the heart.

Figure 6C:
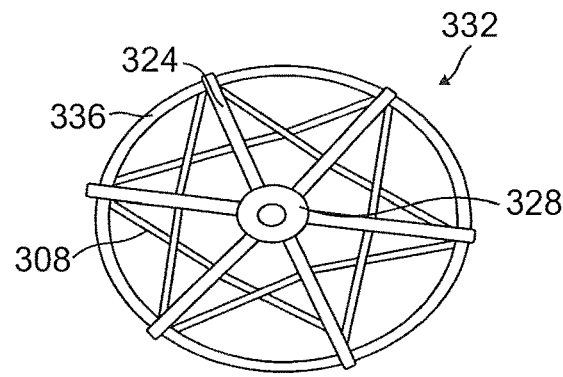
FIG. 6C illustrates an exemplary embodiment of an anchor comprising a circular ring attached to a tension member by way of several spokes, an inner ring, and one or more polymer ribbons.

FIG. 6C illustrates an exemplary embodiment of an anchor 332. Anchor 332 may include ribbons 308 (e.g., PET ribbons), spokes 324, and/or ring 336. The ring 336 is shown as circular in FIG. 6C, but may be formed in other shapes, e.g., ring 336 may be formed as a flower-shaped ring, a star-shaped ring, oval ring, a square ring, a pentagonal ring, a hexagonal ring, etc.) The ring 336 may function in the same or similar way to the anchors and rings discussed above, e.g., the ring 336 may change to a low profile configuration in the same/similar way or a different way from the anchors and rings discussed above. For example, the ring 336 may optionally include a break and/or atraumatic ends similar to those described above with respect to ring 152 and may be configured to allow the ring 336 to be transitioned between a low-profile configuration and a deployed configuration similar to ring 152. Optionally, the ring may function in other ways, e.g., the ring 336 may transition to a lower profile by the sides being compressed together, bent, or folded. Optionally anchor 332 may include an inner ring or hub 328, which may be the same as or similar to the inner ring or hub discussed above. Optionally, a tension member may thread through the ribbons 308 or a portion of the ribbons and cinch them toward the center when tightened, e.g., in a similar way to that discussed above with respect to the embodiment shown in FIGS. 3A and 3B.

The ring 336 may be connected to a tension member directly or may be connected indirectly by connecting to a cover, spokes, ribbons, or an inner ring or hub that connects to the ring 336. The anchor 332 may include a cover and/or spokes that are the same as or similar to the covers 156 or 280 or spokes 212 described above. Optionally, the anchor 332 may include one or more than one ribbon 308 (e.g., a PET ribbon) wound and/or woven to parts of the anchor 296 in various patterns, e.g., in a star-shaped, flower-shaped, triangular, square, pentagonal, or hexagonal pattern. One or more than one ribbon 308 may be woven together and/or woven to the ring 336 so as to form an anchor surface suitable for contacting an exterior surface of the heart 108, the myocardium, or pericardium. More surface area may be created by the ribbons 308 than that shown in FIG. 6C. When in contact with the exterior surface, the tension member 304 may pass through the puncture(s) in the exterior surface and heart wall. The ribbons of material may also strengthen the anchor 332 and improve its ability to withstand high tension forces, e.g., when implanted.

Figure 7A:
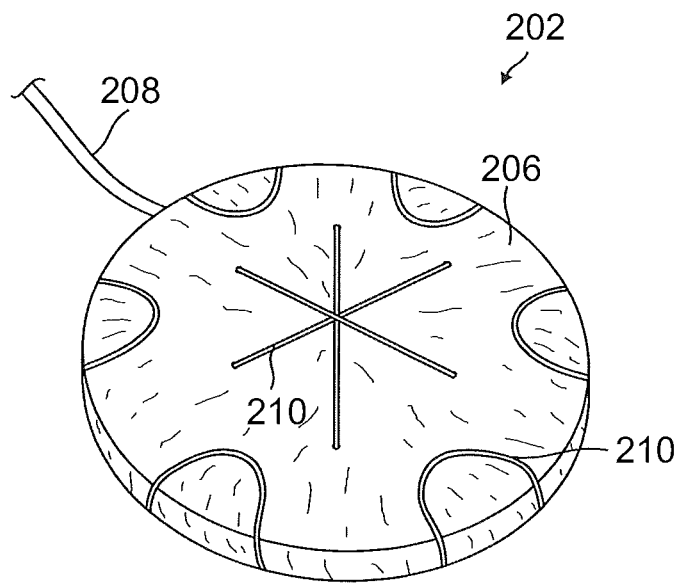
FIG. 7A is a perspective view illustrating an exemplary embodiment of an anchor comprising an expandable balloon attached to a tension member.
Figure 7D:
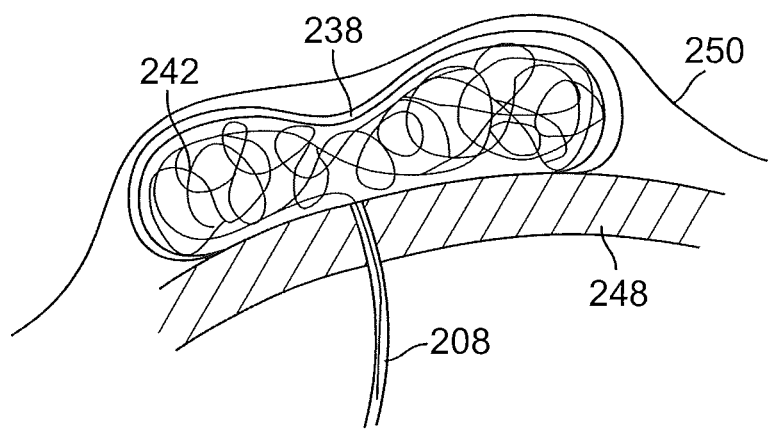
FIG. 7D is a cross-sectional view illustrating an exemplary embodiment of an anchor comprising an expandable balloon with a filled interior.

FIG. 7A illustrates an exemplary embodiment of an anchor 202 comprising an expandable balloon 206 (while a "balloon" is describe, this encompasses use of a cover, e.g., a pouch cover) that is attached to a tension member 208. The expandable balloon 206 (may be made from any of various medically-approved textiles, such as, by way of non-limiting example, PET, UHMWPE, PEEK, cloth, PTFE, and the like. It is contemplated that the expandable balloon 206 may be comprised of any material that exhibits one or more desirable material properties, such as a suitable tensile strength, facilitates tissue response and/or cell growth, enables an easy and durable connection with the tension member 208, facilitates a relatively low crimping profile, etc. The expandable balloon 206 may further comprise one or more sutured structures/patterns 210. The sutured structures/patterns 210 may be in a variety of sizes and shapes, e.g., they may include curved or straight lines forming one or more of a variety of patterns on the top, bottom, sides, or more than one of these of the balloon. In one embodiment, the sutured structures/patterns 210 may comprise a flat structure wherein straight, curved, partially curved, etc. non-planar suture lines are used to form a pattern on top, sides, and/or bottom of the expandable balloon 206. FIG. 7A shows some exemplary suture structures/patterns 210. In one embodiment, a curved, or partially curved, non-planar suture line may advantageously increase the tensile strength and decrease the crimping profile of the expandable balloon 206. In one embodiment, one or more planar suture lines may be used to form a 2D or 3D structure on top of the expandable balloon 206, without limitation.

In some embodiments, the expandable balloon 206 may be configured to be filled with a filler material 242 so as to occupy an interior volume of the balloon, or a portion of the interior volume of the balloon, such as, by way of non-limiting example, a circumflex area of the expandable balloon 206. The filler material 242 may be comprised of any material found to be suitable for occupying the interior volume of the balloon, such as, but not limited to, liquid, a liquid that fixates over time (e.g., an epoxy), flexible coils, one or more rings (e.g., self-expandable or manually expandable), mini-spheres or micro-spheres comprised of metal or plastic, other fillers that may be delivered to a balloon via a relatively narrow tube, and a combination of one or more of these. The material may be of a liquid, gaseous, metal, polymer, cloth, or other material. For example, in one embodiment, illustrated in FIG. 7D, an anchor 238 may be filled with a filler material 242 in the form of a wire filler or coil (e.g., this may be similar to the concept of a coil that is used to fill and treat an aneurism) and may be disposed between the myocardium 248 of the heart 108 and the pericardium 250. In one embodiment, partial filling may be achieved by using a Nitinol wire to form a spiral shape at the balloon circumflex area. In one embodiment, the filler material may be comprised of metal or plastic spheres having a diameter of substantially 1.5 millimeters (mm) (though a variety of diameters are possible, e.g., 0.1-3 millimeters, 0.5-2 millimeters). It is contemplated that mini-spheres or micro-spheres advantageously provide an optimal spatial arrangement within the interior volume of the expandable balloon 206.

Various delivery and filling devices and techniques may be used to deliver the anchor 202 and to deliver one or more of a variety of filler materials to the balloon or filling space of the balloon. In one embodiment, the anchor 202 and/or balloon 206 may be delivered using a delivery catheter. The anchor 202 and/or balloon 206 may be contained within a lumen of the delivery catheter until it arrives at a location for deployment (e.g., a posterior wall of a left ventricle) and may be expanded out of the lumen to an expanded or deployed configuration using a filler material, preliminary inflation fluid or material, and/or a pushing device. In one embodiment, the balloon may assume a low profile around an outer wall of an end of a delivery catheter during delivery and be expanded away from the outer wall upon arriving at the deployment location. In one embodiment, a stylet, pushing device, ring, etc. may be used to extend the balloon forward into a stretched, elongated configuration (e.g., similar to balloon 258 as shown in FIG. 8A) that has a reduced diameter for delivery, e.g., a stylet could be pushed through a lumen of a delivery catheter and extended until it pushes a distal end of the balloon forward and stretches it to a lower diameter profile.

Figure 7B:
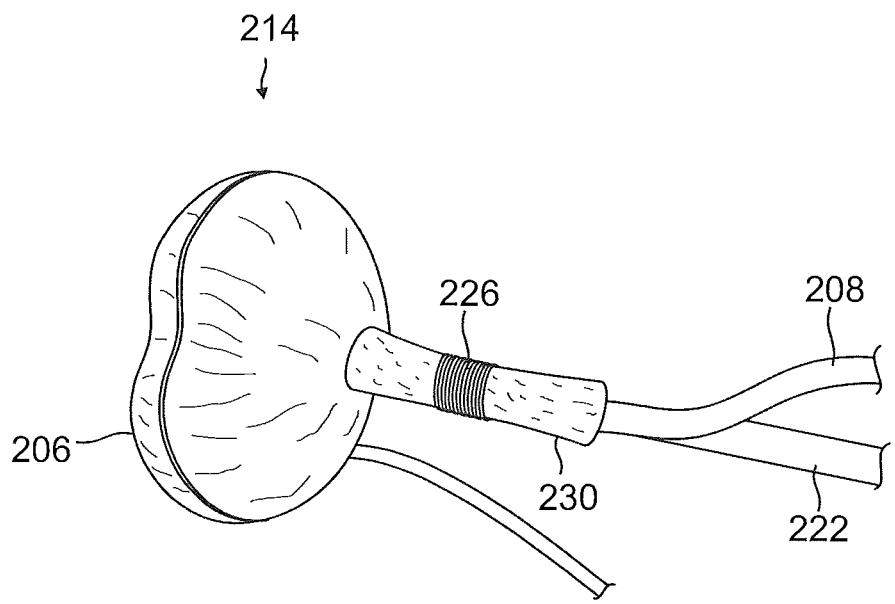
FIG. 7B is a perspective view illustrating an exemplary embodiment of an anchor comprising an expandable balloon coupled with a filling tube and a spring locker.
Figure 7C:
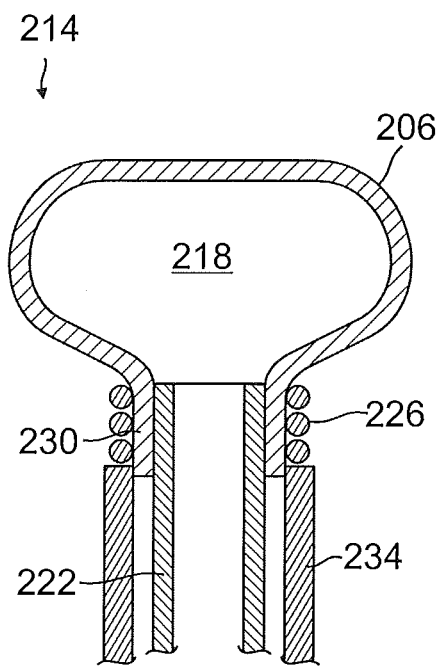
FIG. 7C is a cross-sectional view of an anchor comprising an expandable balloon that may be similar to the anchor of FIG. 7B that shows fluid communication between a filling tube and an interior of the expandable balloon.

FIGS. 7B-7C illustrate an anchor 214 comprising an expandable balloon 206 disposed in filling configurations wherein an interior 218 of the expandable balloon may be filled with a filler material (e.g., a liquid, flexible coil, spheres, or other material). As can be seen in FIG. 7C, the expandable balloon 206 may be placed into fluid communication with a filling catheter or tube 222, and the balloon may be attached to the filling catheter/tube 222. This attachment or connection may be by way of a spring 226, clamp, stent, or other fastening device or mechanism. The expandable balloon 206 preferably is attached to the filling catheter/tube 222 such that the balloon is suitably sealed to the filling catheter/tube during the filling process and may be controllably removed from the filling catheter 222 after the filling process. In one embodiment, the spring 226 may be comprised of a nitinol spring or other device that is shape-set to an inner diameter that is smaller than the outer diameter of the filling catheter 222. The spring 226 may be twisted around a sleeve portion 230 of the expandable balloon 206. After the filling process is finished, an external pusher 234 may be advanced to push the spring 226 and the sleeve portion 230 away from the filling catheter 222. In absence of the filling catheter 222, the spring 226 or other attachment device may return to a smaller (e.g., a shape-set) dimension or inner diameter and press the sleeve portion 230 closed to seal the interior 218 of the expandable balloon 206. The filling catheter/tube 222 may act as a delivery catheter as well (see discussion of delivery catheters herein) to deliver the anchor and/or balloon to the desired location.

In general, the filler material may be delivered to the filling catheter/tube 222 by way of various deliver devices or mechanisms. In one embodiment, magazines of filler material may be easily attached to and detached from a main delivery system. In some embodiments, two or more filling catheters/tubes (e.g., two filling catheters/tubes comprising a curved tip) may be used for filling (e.g., symmetrically filling) of the interior 218. In one embodiment, wherein the filler material comprises a wire or coil (e.g., a nitinol wire), a shaped filling catheter comprising two curved tips may be used to insert the nitinol wire into the interior 218 at a 90 degree (or 60-120 degree) turn with respect to the shaft or longitudinal axis or the shaped filling catheter. In one embodiment, the shaped filling catheter/tube may comprise two curves, or may comprise two single curved filling tubes located at a 180-degree angle relative to one another.

Figure 8A:
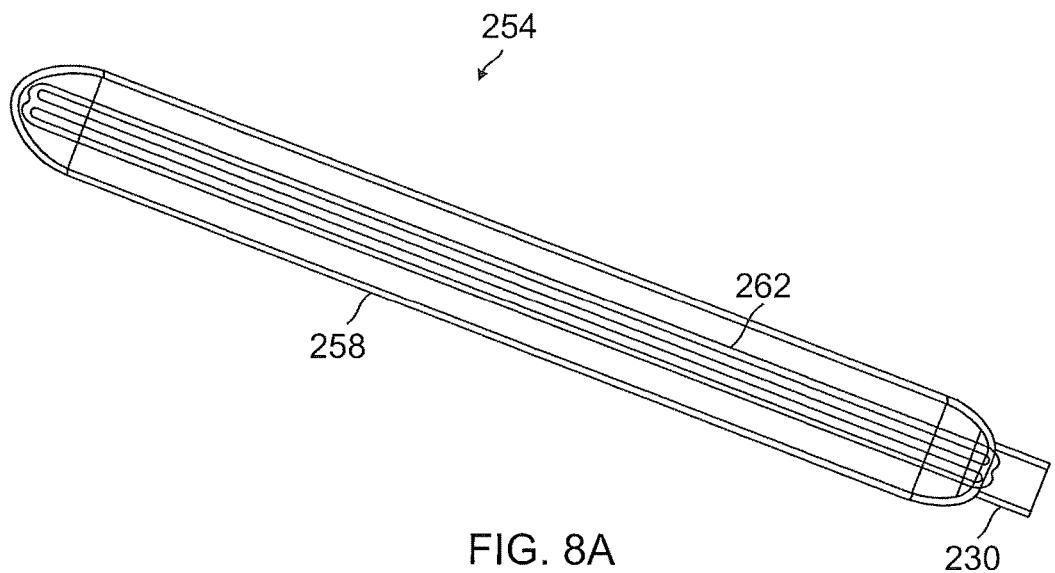
FIG. 8A is a side cross-sectional view of an exemplary embodiment of a self-expandable anchor comprising a balloon and an internal wire ring that are in a low profile configuration suitable for being deployed inside a catheter.
Figure 8B:
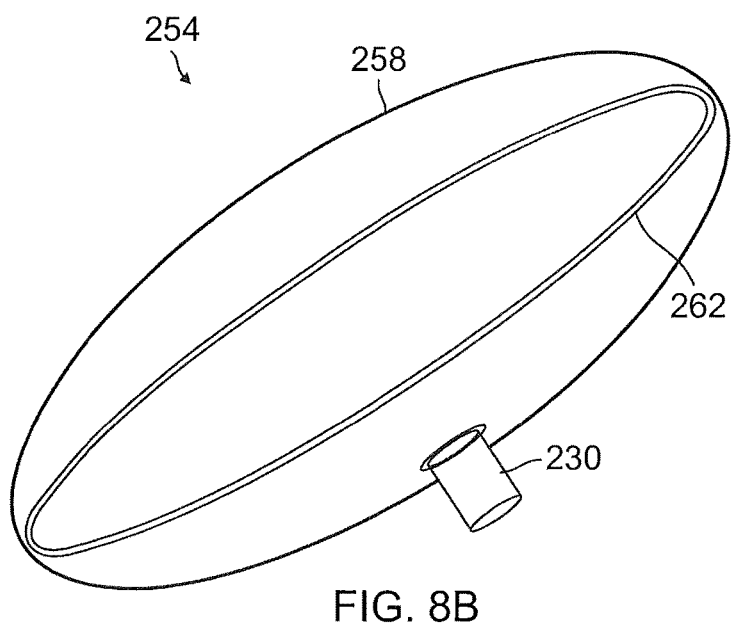
FIG. 8B is perspective view of an expanded configuration of the self-expandable anchor illustrated in FIG. 8A.

FIGS. 8A-8B illustrate an exemplary embodiment of an expandable anchor 254 (which may be self-expandable, partially self-expandable, or manually expandable) comprising an expandable balloon 258 (while a "balloon" is described this encompasses a cover, e.g., a pouch of cloth or other material, or similar concepts can be used with one of the covers described elsewhere herein), and an internal ring 262 (e.g., a wire ring) that may be crimped into a low profile configuration suitable for being delivered and/or deployed from inside a catheter. The ring 262 may be comprised of a shape memory material, such as a shape memory alloy, nitinol, or another similar material that, when deployed, changes the expandable balloon 258 (and/or a cover) to an expanded configuration of the expandable anchor 254 (e.g., as illustrated in FIG. 8B). In one embodiment, the ring 262 may be attached to the expandable balloon 258 (and/or a cover) by way of an internal groove, one or more sutures, loops, and/or other means, such that the ring is folded into an elongate shape or a saddle-shape during crimping into the low profile configuration of FIG. 8A. In one embodiment, if a cover similar to cover 156 (e.g., as used in FIG. 3A) is used, a ring may be crimped for delivery and expand in a similar way to ring 262 to expand the cover 156. It is contemplated that a balance between a small wire diameter to allow elastic deformation at low crimping profiles and a sufficient opening force to expand the balloon 258 should be maintained. As such, in one embodiment, the ring 262 may be comprised of multiple loops of a single wire. In one embodiment, the ring 262 may be comprised of multiple separate rings that are connected by sutures such that the rings form a uniform structure after expanding. In some embodiments, the wire(s) comprising the ring 262 may be comprised of circular or rectangular wire. In some embodiments, an expandable frame may be disposed inside the expandable balloon 258. The expandable frame may be sutured to the expandable balloon 258 or may be deployable after the balloon so as to reduce crimping profile. The expandable frame may be comprised of nitinol braiding, laser cut tube, or other suitable components.

In some embodiments, the expandable balloon 206 or expandable balloon 258 may be temporarily expanded to restore its shape after being deployed in the crimped, low-profile configuration shown in FIG. 8A. In one embodiment, temporary expanding of the expandable balloon 206 or 258 may be achieved by inflating a smaller balloon inside the expandable balloon 206 or 258 to aid in returning the expandable balloon to the expanded configuration shown in FIG. 8B. In some embodiments, wherein the expandable balloon 258 comprises a sealed structure or a coating (e.g., that is fluid tight), the expandable balloon 258 may be filled with saline or other suitable fluid to restore the shape of the expandable balloon after being deployed. In some embodiments, a nitinol structure may be inserted into the expandable balloon 258 by way of a catheter so as to restore the expandable balloon to the expanded configuration after deployment.

Figure 9A:
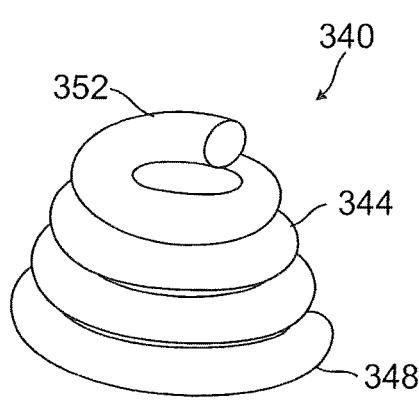
FIG. 9A is a perspective view illustrating an exemplary embodiment of an anchor.

FIG. 9A illustrates an exemplary embodiment of anchor 340 which is particularly well suited for use as the superior anchor 116 in accordance with the present disclosure, but may optionally be used as the inferior anchor 140. FIG. 9A depicts anchor 340 as a cone-shaped anchor, but it could also be other shapes, e.g., a cylindrical shape, helical shape, etc.

Figure 9B:
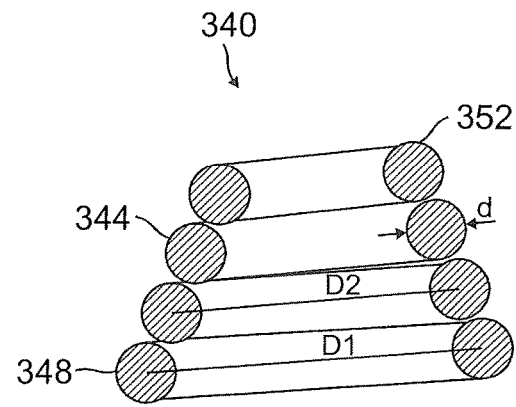
FIG. 9B is a cross-sectional view taken along a midline of the anchor illustrated in FIG. 9A.

FIG. 9B is a cross-sectional view taken along a midline of the coiled anchor 340. The coiled anchor 340 generally comprises several turns of a coiled wire 344. In one embodiment, the diameter of the coil decreases as it transitions from a base portion 348 to a top portion 352. As best illustrated in FIG. 9B, the anchor 340 is cone-shaped so long as a difference in diameter of adjacent turns of the coil is less than the diameter of the wire comprising the coiled wire 344, or D1−D2>d with reference to FIG. 9B. Once deployed into the heart 108, the tension member or cord 160 may be affixed to the top portion 352 and pass through the center of the coils with the base portion 348 pulled into contact with the exterior surface of the heart. The coiled anchor generally provides a relatively stiff anchor possessing a large area of contact with the surface of the heart 108. The coiled wire 344 preferably is comprised of a shape memory material, such as nitinol, a shape memory alloy, or other similar material. The coiled wire 344 may be covered with a cover (e.g., a fabric or tissue suitable for deployment in the heart 108 and/or for tissue ingrowth). The cover may be formed of the same or similar materials to the covers discussed above. It is contemplated that the coiled anchor 340 may be produced with a degree of pre-tension so as to provide an advantageous level of anchoring in severe deployment conditions. It is further contemplated that in some embodiments, the anchor 340 may be practiced without a decrease in coil diameter, such that the anchor is cylindrically-shaped, e.g., D1=D2 and so forth.

Figure 10A:
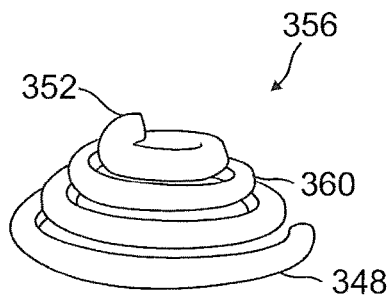
FIG. 10A is a perspective view illustrating an exemplary embodiment of another anchor.
Figure 10B:
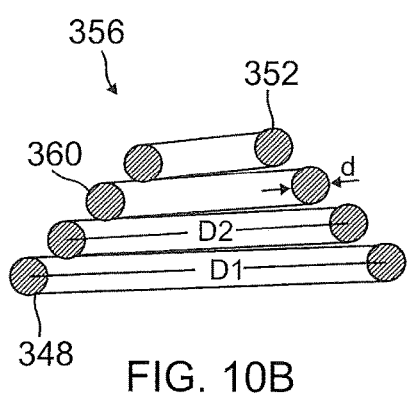
FIG. 10B is a cross-sectional view taken along a midline of the anchor of FIG. 10A.

FIG. 10A illustrates an exemplary embodiment of a telescope-shaped, coiled anchor 356, according to the present disclosure. FIG. 10B is a cross-sectional view taken along a midline of the telescope-shaped anchor 356. The telescope-shaped anchor 356 is substantially similar to the cone-shaped, coiled anchor 340 and may include the same or similar features; however, the telescope-shaped anchor 356 comprises a wire coil 360 wherein the difference in diameter of adjacent turns of the coil is greater than the diameter of the wire, or D1−D2>d as shown in FIG. 10B. Thus, the telescope-shaped anchor 356 provides a large area of contact with the surface of the heart 108; and in the case of extreme tension of the tension member or cord, the area of contact increases, which advantageously decreases contact tractions and provides for stronger anchoring.

Figure 11A:
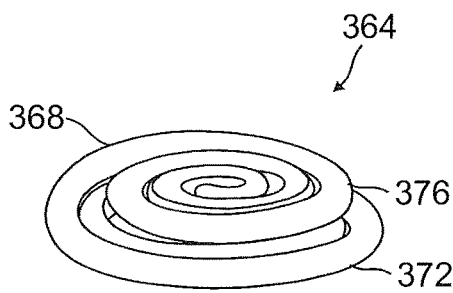
FIG. 11A is a perspective view illustrating an exemplary embodiment of another anchor.
Figure 11B:
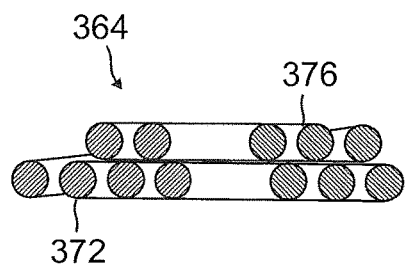
FIG. 11B is a cross-sectional view taken along a midline of the anchor illustrated in FIG. 11A.

FIG. 11A illustrates an exemplary embodiment of a floor-like, coiled anchor 364, which can be used, for example, as the superior anchor 116. FIG. 11B is a cross-sectional view taken along a midline of the anchor 364. The anchor 364 is similar to the coiled anchors illustrated in FIGS. 9A-10B and may include the same or similar features; however, the anchor 364 shown in FIGS. 11A-11B comprises a wire coil 368 which is wound so as to form a lower level 372 and an upper level 376. The lower level or base portion 372 provides a relatively large area of contact with the exterior surface of the heart 108 while also preventing the upper level or top portion 376 and the tension member or cord 160 from being drawn under tension into the puncture in the wall of the heart 108. Although the illustrated embodiment of the floor-shaped anchor 364 comprises a two-level structure, it is contemplated that in some embodiments, the floor-shaped anchor may comprise more than two-levels, as deemed appropriate.

It is contemplated that each of the coiled anchors shown in FIGS. 9A-11B and/or discussed above may be used as a superior and/or inferior anchor. It is further contemplated that these anchors may be used in similar methods and/or delivered and deployed in a similar manner to the anchor shown in FIGS. 3A-3B or other anchors described herein.

For example, the coiled anchors may be formed of a shape memory material or alloy (e.g., nitinol) and may be transitioned to a low profile (e.g., a straightened or substantially straightened configuration) to be loaded into a delivery catheter. The coiled anchors may be delivered to a desired location inside a delivery catheter, then deployed out of the delivery catheter. When deployed, the coiled anchors may transition automatically from the straightened or low profile configuration back to their deployed configuration, e.g., the coiled configurations shown in FIGS. 9A-11B. Thus, these may also be considered self-expanding anchors. Optionally, the anchors could be manually expandable, or only partially self-expandable as well. Optionally, any of the anchors described herein could be deployed surgically or with minimally invasive surgery to a side of the heart without first passing through the heart.

Moreover, the anchors shown in FIGS. 9A-11B need not be limited to wire coils having circular wire patterns, but rather any of the wire coils shown in FIGS. 9A-11B may comprise a non-circular wire pattern, such as, by way of non-limiting example, rectangular, square, triangular, pentagonal, hexagonal, oval, ovoid, ellipsoid, as well as any other suitable shape, e.g., each turn of a coil may have one of these shapes and each turn of the coil may be the same or different shapes. Similarly, the coiled wires comprising the anchors shown in FIGS. 9A-11B need not be limited to wires having circular cross-sectional shapes. For example, in some embodiments the cross-sectional shape of the wires may be oval, ovoid, ellipsoid, flower shaped, star shaped, triangular, square, rectangular, pentagonal, hexagonal, as well as any other suitable shapes without limitation.

Figure 12A:
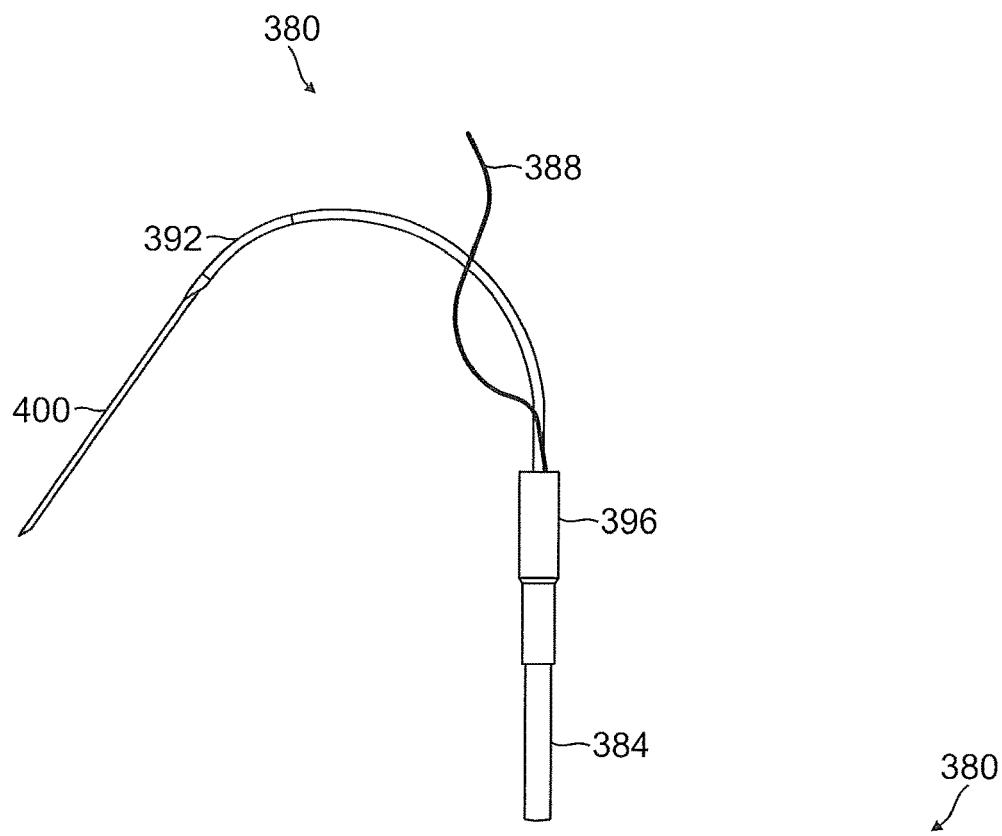
FIG. 12A is a side view illustrating an exemplary embodiment of a spade-shaped assembly for use with a transcatheter system.

FIGS. 12A-15C illustrate an exemplary embodiment of an assembly 380 for use with an anchoring system, according to the present disclosure. The assembly 380 is depicted as a spade-shaped stabilizing assembly, but other shapes are possible and, in one embodiment, the wire spade portion could be omitted. The assembly 380 can be used as a septum-puncture assembly to puncture a septum between portions (e.g., ventricles) of the heart, and may be used as a stabilizing assembly to stabilize a portion of the assembly or a puncturing instrument for puncturing the septum. The assembly 380 generally is configured to be deployed in the right ventricle 120 of the heart 108 at a distal end of a catheter 384. As illustrated in FIGS. 12A-12B, the assembly 380 may comprise a wire spade 388, an outer needle 392, an inner needle 400, a catheter head 396, and/or a catheter 384. The catheter 384 may be considered part of the spade-shaped stabilizing assembly 380 or may be considered a separate component to which a wire spade or spade-shaped assembly may attached. The catheter 384 could, optionally, be a directional catheter that can transition between a straight configuration and a bent or angled configuration (e.g., at a 90 degree or other angle). Wire spade 388 and needle 392 may be connected to the catheter 384 by way of a catheter head 396. The wire spade 388 may be configured to be received into the right ventricle 120 and provide stability to the spade-shaped assembly 380 while the needle 392 penetrates the septum 132 between the right ventricle and the left ventricle and enters the left ventricle.

The needle 392 may be curved as shown in FIGS. 12A-14B, or the needle 392 may be a different shape (e.g., form a right angle) and/or may be bendable/transitionable (e.g., movable between a straight configuration and a bent or angled configuration). Optionally, needle 392 may include, within a lumen of the needle 392, an inner needle 400. The inner needle 400 may also be curved and/or flexible and may be configured to be advanced from the lumen of the curved needle 392 across the left ventricle 116 and puncture the posterior wall of the left ventricle after the curved needle 392 has passed through the septum 132. One, more than one, or all of the wire spade 388, the curved needle 392, and the inner needle 400 may be comprised of a shape memory material, such as nitinol, a shape memory alloy, or other similar material, and may be configured so as to assume the shapes shown in FIGS. 12A-12B. Optionally, these may be configured to assume other shapes as well; for example, the wire spade 388 may be configured to have a more circular, triangular, rectangular, square, or other shape. Further, the wire spade 388 (e.g., as used in FIGS. 12A-12B or elsewhere herein) may be comprised of multiple branches or more than one shaped wire; for example, the wire spade 388 may be comprised of a first wire 382 and a second wire 386 (or more wires) that are coupled with the catheter head 396, e.g., as shown in FIG. 12C. The first and second wires (or one, two, three, four, etc. separate wires) may form a wire spade with multiple branches (e.g., four branches as shown in FIG. 12C). The first and second wires 382, 386 or multiple branches of one or more wires may cooperate to stabilize the assembly 380 within the right ventricle 120 while the needle penetrates the septum 132, as described with respect to FIGS. 12A-12B. It is contemplated that the first and second wires 382, 386 may be particularly well suited to stabilize the assembly 380 in right ventricles 120, even large right ventricles. The embodiments of the wire spade 388 illustrated in FIGS. 12A-12C may be collapsible to a lower profile shape or configuration for less invasive or traumatic insertion into the right ventricle, then expand to an expanded shape that stabilizes the assembly 380 in the right ventricle, e.g., during penetration of the septum with the needle 392.

Figure 12B:
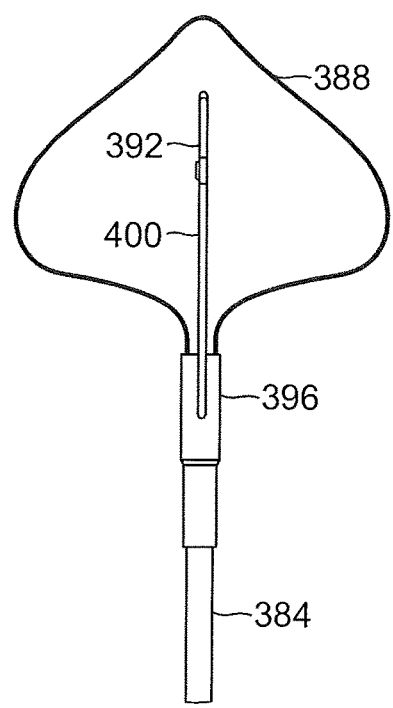
FIG. 12B is a top view of the exemplary embodiment of the spade-shaped assembly illustrated in FIG. 12A.
Figure 12C:
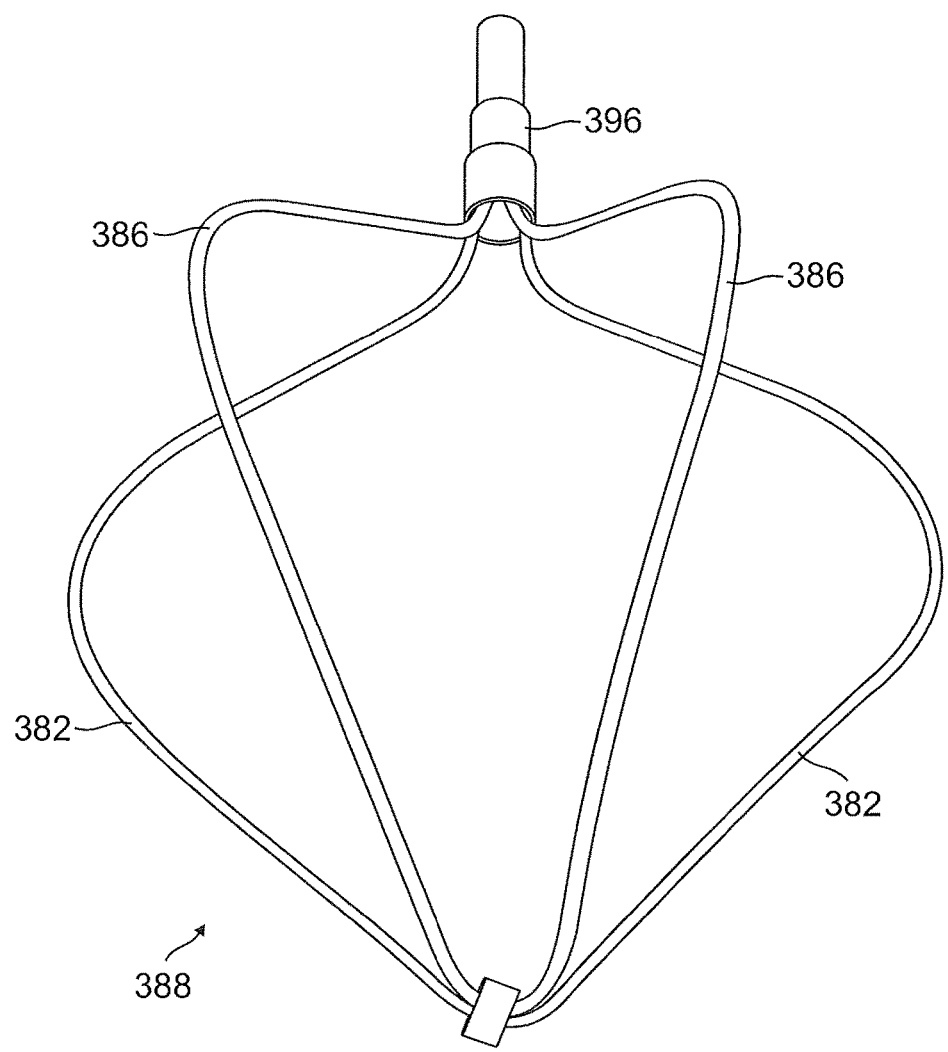
FIG. 12C illustrates another exemplary embodiment of a spade-shaped assembly configured for use with a transcatheter system.
Figure 13:
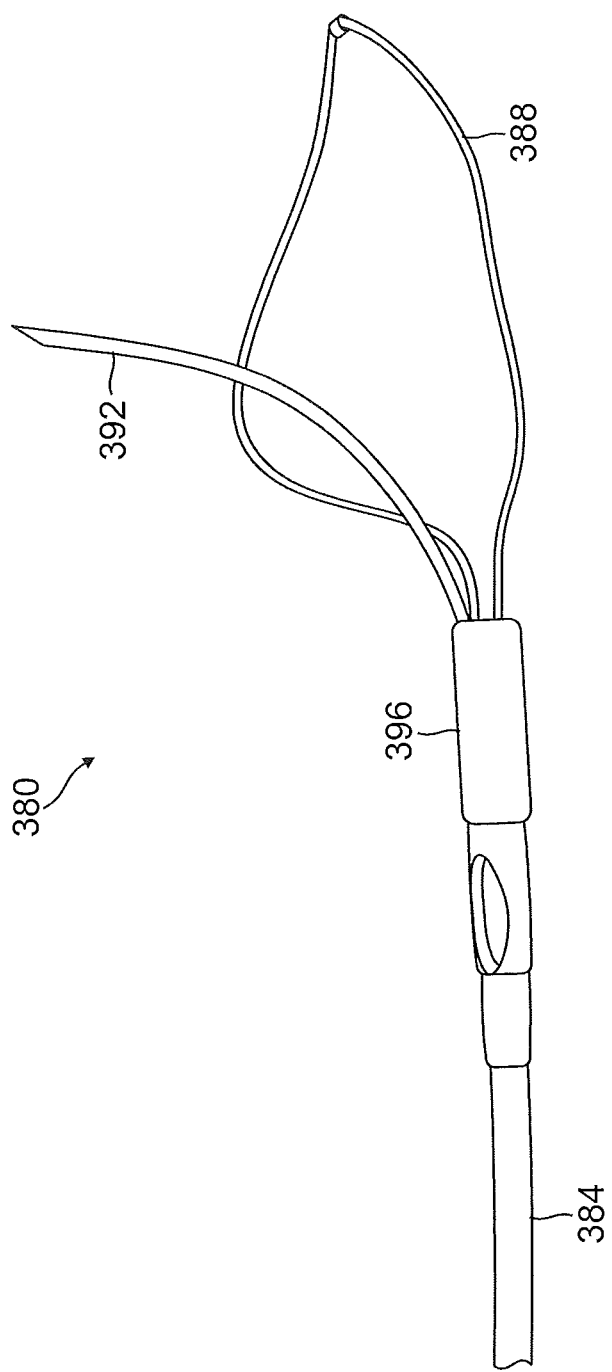
FIG. 13 illustrates an exemplary embodiment of a spade-shaped assembly comprising a curved needle a distal end of which is angled at substantially 90 degrees relative to a catheter.
Figure 14A:
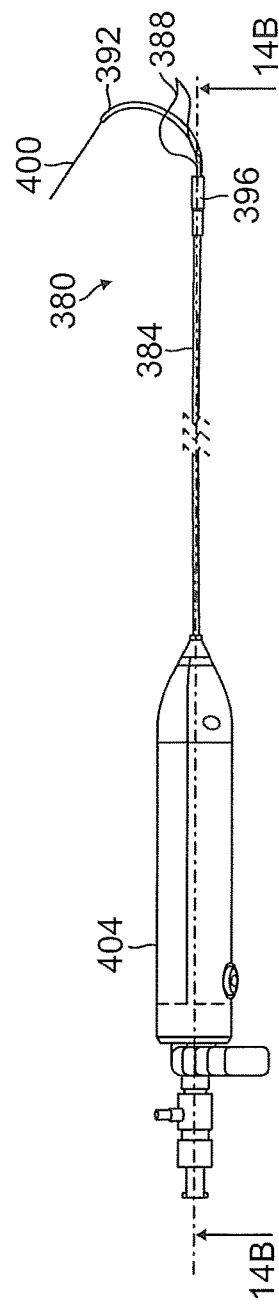
FIG. 14A is a side plan view illustrated an exemplary embodiment of a spade-shaped assembly including an orientation handle.
Figure 14B:
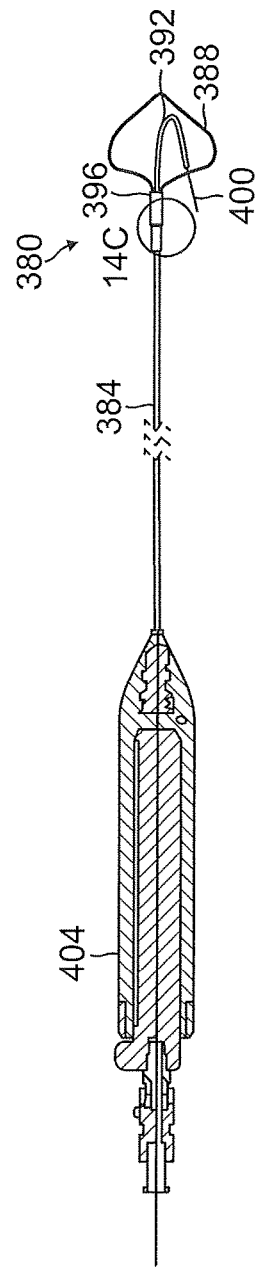
FIG. 14B shows a cross-sectional view of the orientation handle taken along a midline of the exemplary embodiment of the spade-shaped assembly of FIG. 14A.

The embodiments of the wire spade 388 illustrated in FIGS. 12A-12C may comprise a shape and size suitable for contacting one or more interior surfaces of a heart (e.g., a right ventricle 120, or other chamber) while supporting the needle 392 such that it can penetrate the septum at substantially a 90-degree angle (or another angle, e.g., between 45 and 145 degrees or between 70 and 120 degrees) relative to the wire spade or the catheter. The angle of the tip of the needle 392 relative to the catheter 384 or wire spade 388 may increase or decrease with an increasing distal extension of the needle beyond the catheter head 396, e.g., if curved, the further curved needle 392 extends from the catheter 384, the angle the tip of the curved needle 392 points may change relative to the catheter 384 or wire spade 388. The angle of the tip of the curved needle 392 illustrated in FIG. 12A is substantially 145 degrees. As shown in FIG. 13, the radial angle of the curved needle 392 is substantially 90 degrees. A variety of other angles are also possible including, without limitation, in the range from 45 to 145 degrees, from 70 to 120 degrees, or from 80 to 100 degrees. Generally, the angle between the tip of the curved needle 392 and the wire spade 388 and the angle between the tip of the curved needle 392 and the catheter 384 may be controlled by a surgeon by way of an orientation handle 404. As shown in FIGS. 14A-14B, the orientation handle 404 may be located at a proximal end of the catheter 384 and comprises a handle and controls whereby the surgeon may operate the spade-shaped assembly 380 or components of the spade-shaped assembly, e.g., to extend, retract, rotate, and/or change the orientation of the curved needle 392 and/or the inner needle 400.

Figure 14C:
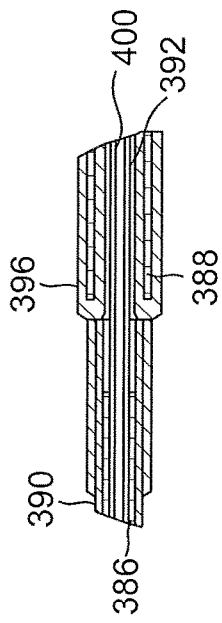
FIG. 14C is a close-up cross-sectional view of an area of the catheter head of the shape-shaped assembly bounded by the circle shown in FIG. 14B.

FIG. 14C shows a close-up cross-sectional view of an area of the stabilizing assembly 380 bounded by the circle shown in FIG. 14B, and shows one exemplary embodiment of how components of the stabilizing assembly 380 may be coupled, combined, and/or attached. Wire spade 388 is attached on one end with its ends inserted into the catheter head 396. The opposite end shows an example of how the catheter 384 may be attached to the catheter head. A connecting tube 386 may be used to connect to the catheter 384 and a wrapping tube 390 may be positioned over the connecting tube 386 and a portion of the catheter 384 to help hold these together. While a variety of materials may be used, in one embodiment the connecting tube 386 is formed of nitinol and the wrapping tube 390 is a braided tube. Wrapping tube 390 may also be a shrink wrap tube. Other ways of connecting the catheter 384 to the catheter head 396 may also be used. Optionally, no connecting tube 386 may be used and the catheter 384 may extend into the catheter head 396, e.g., in place of connecting tube 386. Optionally, no wrapping tube 390 may be used and catheter 384 may be directly adhered, bonded, or otherwise connected to the inner wall of catheter head 396.

Figure 15A:
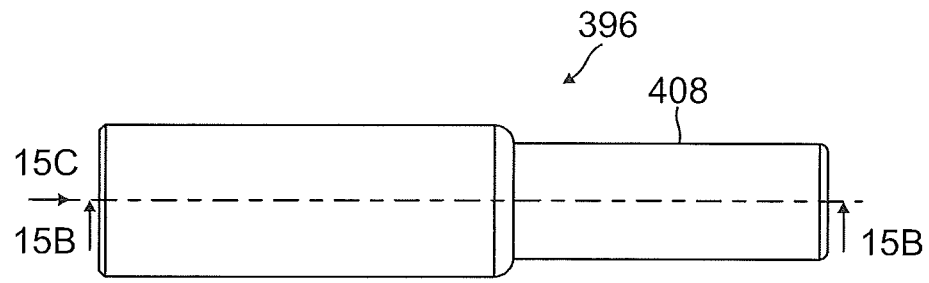
FIG. 15A is a side plan view illustrating an exemplary embodiment of a catheter head.
Figure 15B:
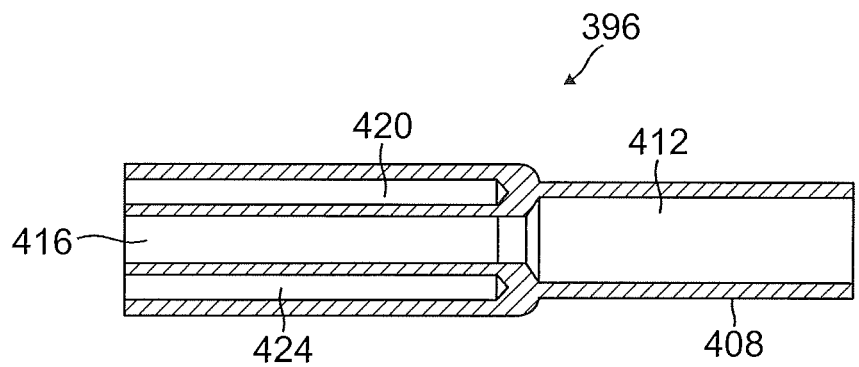
FIG. 15B is a cross-sectional view of the exemplary embodiment of the catheter head illustrated in FIG. 15A.
Figure 15C:
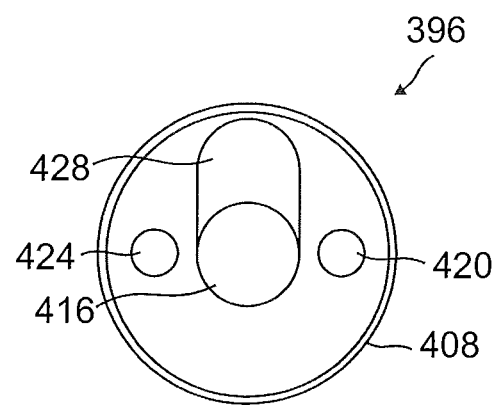
FIG. 15C is a plan view of a distal end of the exemplary embodiment of the catheter head of FIG. 15A.

FIGS. 15A-15C illustrate detailed views of a catheter head 396 that may be used as part of the spade-shaped assembly 380. As best shown in FIG. 15A, the catheter head 396 may comprise a generally elongate, cylindrical body 408 suitable for coupling to the catheter 384 and to the wire spade 388 on opposite ends. As shown in FIG. 15B, a proximal lumen 412 is centrally disposed within the catheter head 396 and configured to receive a distal end of the catheter 384, as shown in FIGS. 12A-13. A distal lumen 416 is in fluid communication with the proximal lumen 412 and is configured to allow passage of the curved needle 392 extending distally from the catheter 384. Two wire receiving lumens 420, 424 are distally disposed within the catheter head 396 on opposite sides of the distal lumen 416. It will be appreciated that the two wire receiving lumens 420, 424 are configured to receive the ends of the wire spade 388 such that the wire spade has a desirable orientation for stabilizing the spade-shaped assembly, e.g., as shown in FIGS. 12A-13. The wires spade 388 may be secured within the lumens 420, 424 in any suitable manner, e.g., by adhesion, bonding, welding, mechanical connection, etc. As best shown in FIG. 15C, at least a portion of the distal lumen 416 may comprise a raised or angled wall 428. As will be appreciated, the raised or angled wall 428 may serve to direct and/or allow the curved needle 392 to move in a desired direction relative to the wire spade 388 and/or the catheter 384.

Figure 16:
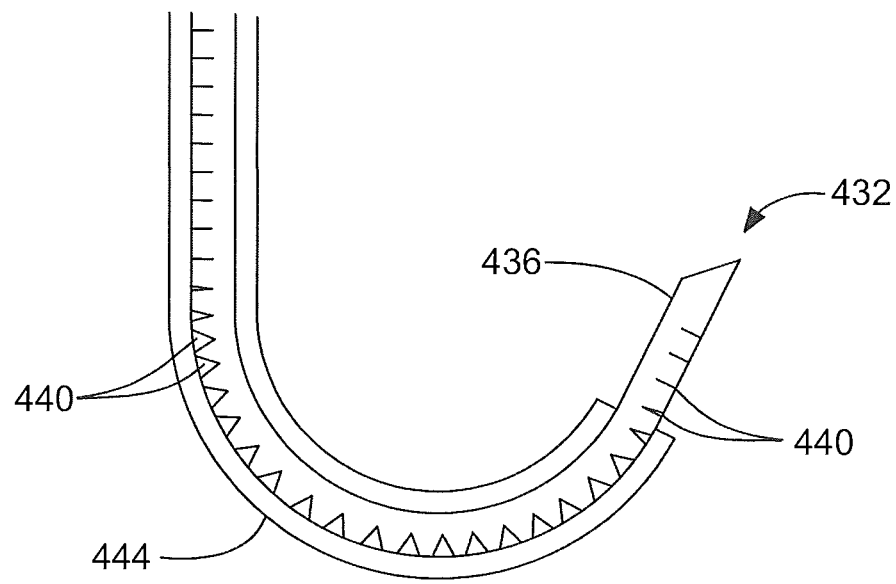
FIG. 16 illustrates an exemplary embodiment of a flexible needle within a curved catheter.
Figure 17:
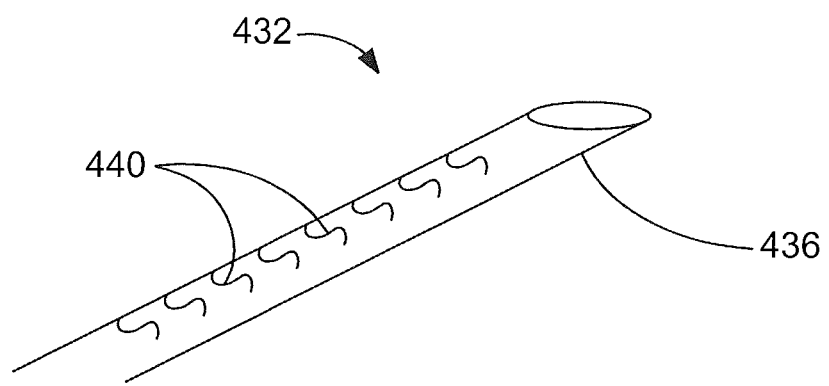
FIG. 17 is a close-up view of a distal portion of an exemplary embodiment of a flexible needle similar to the needle illustrated in FIG. 16.

FIGS. 16-17 illustrate exemplary embodiments of a flexible needle 432, which may be utilized in a capacity the same as or substantially similar to that of the needle 392 and/or the inner needle 400, described in connection with FIGS. 12A-15C. The flexible needle 432 may be included in the anchoring systems or systems for setting an anchor described herein. The flexible needle 432 may generally comprise a hollow, shape memory tube 436 having a multiplicity of slits 440 disposed along the full length of the needle or along a portion of the needle (e.g., a distal portion of the needle). The shape memory tube 436 may be constructed of nitinol, a shape memory alloy, or another suitable material. The slits 440 may be of a variety of shapes/configurations, e.g., S-shaped slits, C-shaped slits, V-shaped slits, zig zag slits, straight slits, curved slits, parallel slits, diagonal slits, etc. FIG. 17 is a close-up view of an exemplary flexible needle 432 showing slits 440 as S-shaped slits along a distal portion of the needle. The slits may be along different portions of the tube, e.g., FIG. 16 shows the slits 440 on the same side as the point of the beveled or sharpened tip of the needle, whereas FIG. 17 shows the slits 440 on the side of the needle opposite the point of the beveled or sharpened tip of the needle. In one embodiment, slits 440 may appear alternating on opposite sides of the needle or appear at varying locations around the needle (e.g., spaced apart in a helical shape around the needle) so the needle can more readily flex in more than one direction. The slits 440 allow the flexible needle 432 to undergo sharp turns when delivered inside a catheter 444 as shown in FIG. 16 (or optionally, when delivered inside a curved needle 392), but allow the flexible needle 432 to resume a straightened configuration when extracted or pushed from the catheter 444 (or curved needle 392), as shown in FIG. 17. The flexible needle 432 may be capable of turns from 1 degree to greater than 90 degrees having a relatively small radius. Further, the slits 440 (e.g., S-shaped slits) may provide a degree of rigidity to the flexible needle 432 in the straightened configuration, including by allowing a surgeon to change the orientation of the tip of the needle 432 by rotating a proximal end of the needle extending from the catheter 384. S-shaped slits may be less likely to break when rotated from a proximal end of the needle than straight slits. The flexible needle 432 is well suited to navigate through tortuous paths, and may enable the surgeon to puncture tissue in a direction different from a previous penetration direction. The catheter 444 may be a directional catheter that can be transitioned from a straight configuration to a curved, bent, and/or angled configuration. The catheter 444 may be flexible, rigid, or semi-rigid.

In some embodiments the flexible needle 432 may be used to deliver devices by way of the hollow tube 436, such as guidewires or small diameter catheters or needles. In some embodiments, the hollow tube 436 may be used to measure pressure where the distal tip of the needle is located. In some embodiments the flexible needle 432 may be utilized as a guidewire during interventions lacking direct visibility. For example, the flexible needle 432 may be used during percutaneous cardiology or radiology interventions, using ultrasonic, angiogram, and/or fluoroscopy imaging modalities, such as during transcatheter left ventricle remodeling procedures for treating left ventricle dilation and any associated functional mitral regurgitation, e.g., as described herein. During transcatheter left ventricle remodeling, for example, the flexible needle 432 may be delivered through the catheter 444 or catheter 384 to the right ventricle 120 of the heart 108 and then oriented toward the septum 132 with a desired orientation. Upon penetrating the septum 132 and entering the left ventricle 116, the flexible needle 432 may resume the straightened configuration illustrated in FIG. 17. In the straightened configuration, the flexible needle 432 may be oriented toward a desired puncture site on the posterior wall of the left ventricle 116. In those instances wherein an additional orientation is required, however, the surgeon may manipulate or rotate the proximal end of the flexible needle 432 so as to orient the flexible needle toward the desired puncture site. Optionally, flexible needle 432 may be delivered through an assembly similar to spade-shaped assembly 380 in the way described above with respect to spade-shaped assembly 380, e.g., flexible needle 432 may be delivered as the curved needle 392 or the inner needle 400 while the spade-shaped assembly 380 is stabilized in the right ventricle.

Figure 18A:
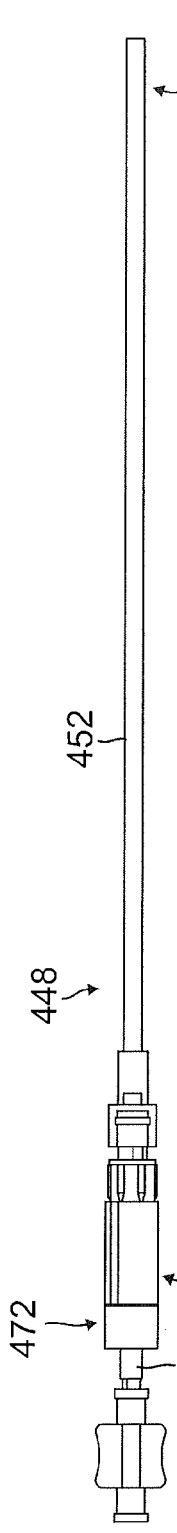
FIG. 18A is a side plan view of an exemplary embodiment of a trocar catheter.
Figure 18B:
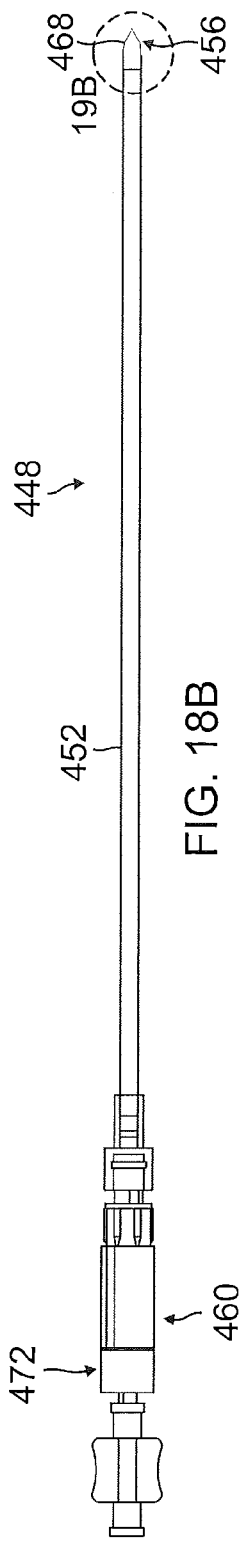
FIG. 18B is a side plan view of the trocar catheter of FIG. 18A with a trocar distal tip deployed.
Figure 18C:
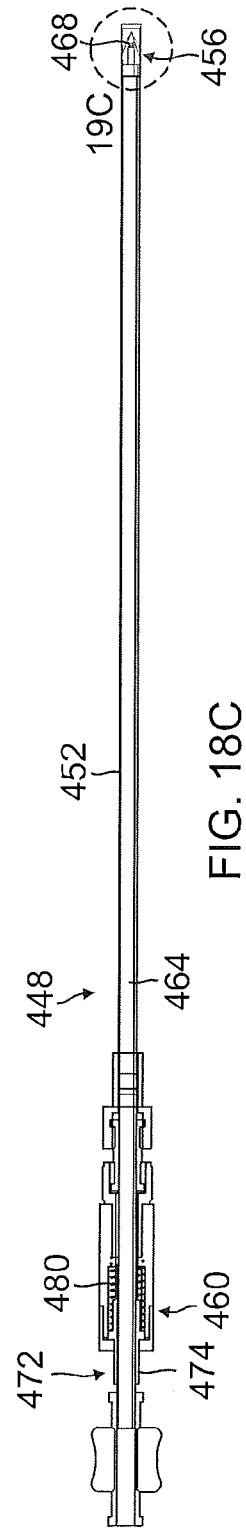
FIG. 18C is a cross-sectional view taken along a midline of the trocar catheter of FIG. 18A illustrating the trocar distal tip retracted into an interior lumen.

FIGS. 18A-18C illustrate an exemplary embodiment of a trocar catheter 448 configured for puncturing tissue. The trocar catheter 448 may be part of an anchoring system or system for setting an anchor as described herein. The trocar catheter 448 may generally comprise an elongate cannula 452 having a distal end 456 and a proximal handle 460. As will be appreciated, the cannula 452 may comprise a hollow interior lumen 450 which may contain a trocar 464. The trocar 464 may comprise a trocar shaft and a trocar distal tip 468. The trocar shaft may be rigid, semi-rigid, or flexible (e.g., to make navigation to the desired location easier) and may have a lumen therethrough. The trocar 464 or trocar shaft may extend from the proximal handle 460 to a trocar distal tip 468. The proximal handle 460 facilitates a surgeon advancing the trocar distal tip 468 beyond the distal end 456, as shown in FIG. 18B, during puncturing of tissue. The handle may include controls (e.g., a lever, button, switch, sliding mechanism, plunger, etc.) for causing the distal tip 468 of the trocar to extend from the distal end of the cannula 452 for puncturing tissue and/or for causing the distal tip 468 to retract into the lumen of the cannula 452 to prevent damage to tissue from the trocar. FIG. 19B is a close-up view of the trocar distal tip 468 extending beyond the distal end 456, as shown in FIG. 18B, in accordance with the present disclosure.

Figure 18D:
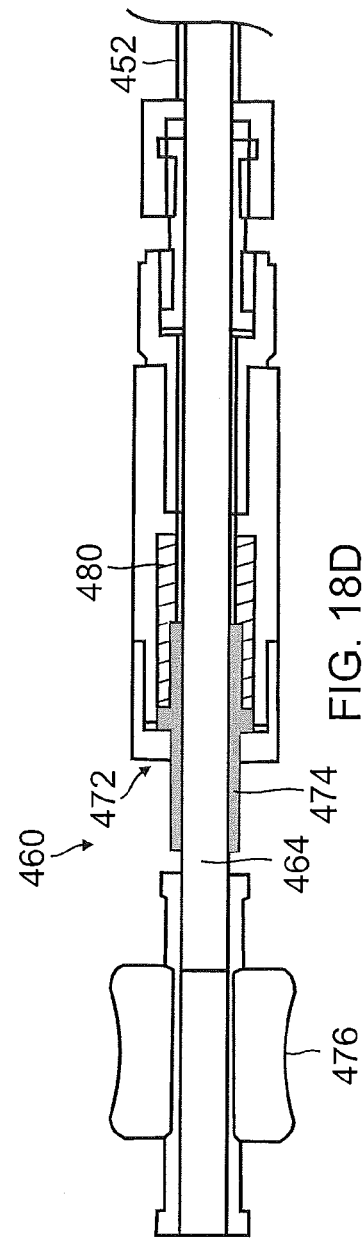
FIG. 18D is a cross-sectional view taken along a midline of a proximal handle of the trocar catheter of FIG. 18A and illustrates a plunger mechanism.

FIG. 18D is a cross-sectional view, taken along a midline of the proximal handle 460, that illustrates controls, e.g., including a plunger mechanism 472, that enable the surgeon to deploy the trocar distal tip 468 during puncturing of tissue and then withdraw or retract the trocar distal tip into the distal end 456, as shown in FIG. 18C. FIG. 19C corresponds to the region in the dotted circle shown in FIG. 18C and is a close-up view of the trocar distal tip 468 positioned within the interior lumen 450, proximal of the distal end 456. As will be appreciated, withdrawing the trocar distal tip 468 into the lumen 450 in the distal end 456 of the cannula 452 prevents unwanted damage to surrounding tissues during delivery of the trocar catheter 448.

As illustrated in FIGS. 18A-18D, the trocar catheter may comprise an actuator 476 configured to deploy the trocar distal tip 468, as shown in FIG. 18B. The actuator 476 may be part of or work with the plunger mechanism 472. The plunger mechanism 472 may comprise a spring 480 that biases the trocar distal tip into the retracted position, i.e., the position in which the distal tip 468 is retracted into the lumen 450 in the distal end 456. If a spring 480 is used, the distal tip 468 may automatically retract into the lumen 450 or into the distal end 456 when the surgeon releases the actuator 476. The actuator 476 may connect (directly or indirectly) to a proximal end of the trocar 464 and may be pushed toward the distal end 456 of the cannula 452 to cause the distal tip 468 of the trocar to extend out from the lumen 450. In FIG. 18D, the distal end of the actuator 476 is shown as aligned with another component or plunger 474 having a ridge or lip on an outer surface thereof that contacts the proximal end of the spring 480. The component or plunger 474 having the ridge or lip may also include a lumen through which a shaft of the trocar 464 may pass. In one embodiment, the distal end of the actuator 476 may push against the component having the ridge or lip and may thereby compress the spring 480 to allow the distal tip 468 of the trocar 464 to move distally and extend out from the lumen 450 and distal end 456 of the cannula. When the actuator 476 is released, spring 480 may then cause the component having the ridge or lip to move proximally and thereby push the actuator proximally to cause the distal tip 468 to move proximally into the lumen 450 and distal end 456. Other controls for moving the trocar between the extended and retracted positions are also possible. A lock may be used to hold the trocar in either the extended or retracted position.

Figure 19A:
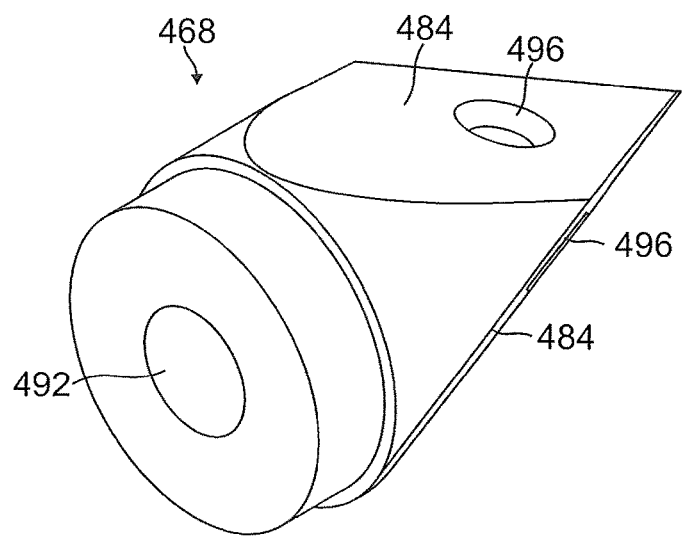
FIG. 19A is a perspective view illustrating an exemplary embodiment of a trocar distal tip.
Figure 19B:
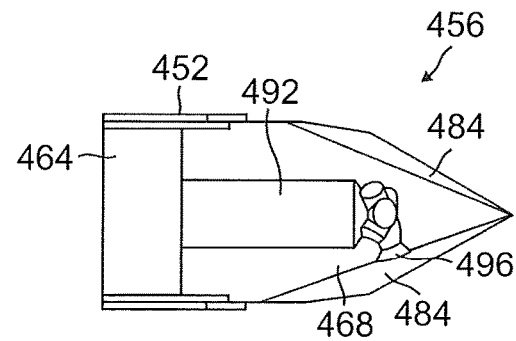
FIG. 19B is a close-up cross-sectional view of the trocar distal tip in a deployed configuration, e.g., as in FIG. 18B.
Figure 19C:
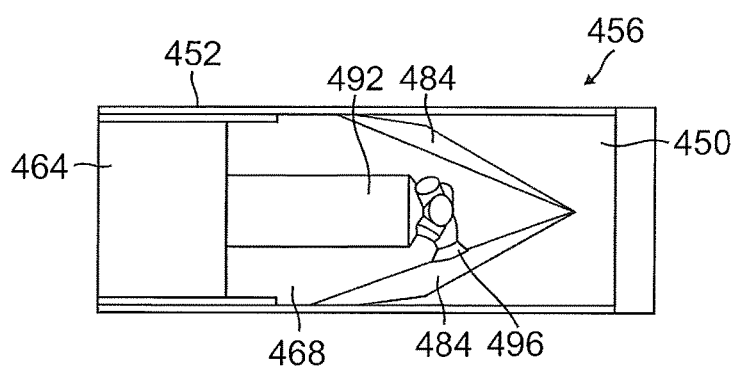
FIG. 19C is a close-up cross-sectional view of the trocar distal tip in a retracted configuration, e.g., as in FIG. 18C.

FIG. 19A is a perspective view of the trocar distal tip 468 in accordance with the present disclosure. The trocar distal tip 468 may comprise one or more surfaces 484 to form a sharpened or a puncture tip, e.g., the distal tip 468 may have one, two, three, four, five, six, or more surfaces 484. The surfaces 484 may be formed/manufactured by grinding or milling the surfaces 484, e.g., the surfaces 484 may each correspond to a grinding plane and be planar surfaces. In FIGS. 19A-19C, the distal tip 468 is shown as having been ground or milled to form three grinding plane surfaces 484 that meet to form a sharp tip. The actuator 476 may be rotatable so as to enable the surgeon to turn the surfaces 484 of the trocar distal tip 468 during tissue puncturing. Further, the trocar distal tip 468 may comprise a lumen 492 in fluid communication with one or more ports 496 disposed on one or more or all of the surfaces 484. The lumen 492 and ports 496 may be configured for contrast injection therethrough before, during, and/or after tissue puncturing.

Figure 20A:
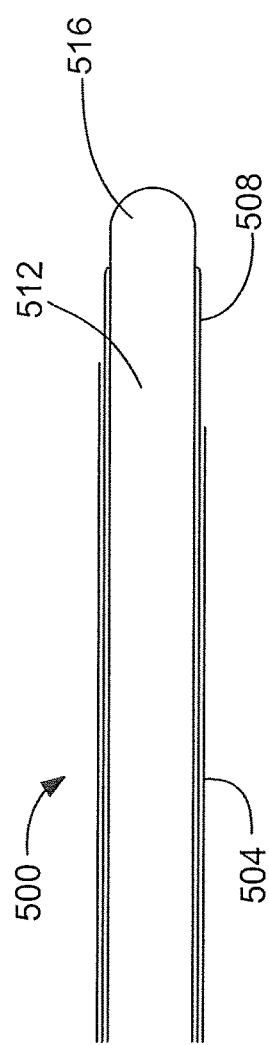
FIG. 20A illustrates an exemplary embodiment of an introducer system suitable for interventional cardiology procedures.
Figure 20B:
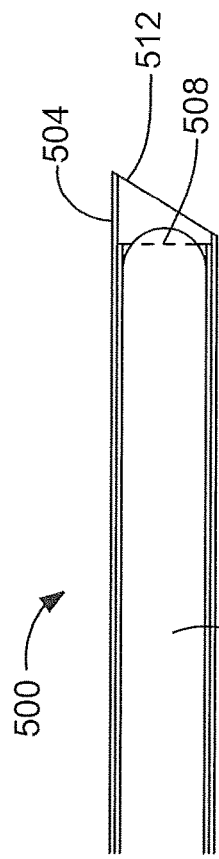
FIG. 20B illustrates the exemplary embodiment of the introducer system of FIG. 20A in a configuration for puncturing tissue.
Figure 20C:
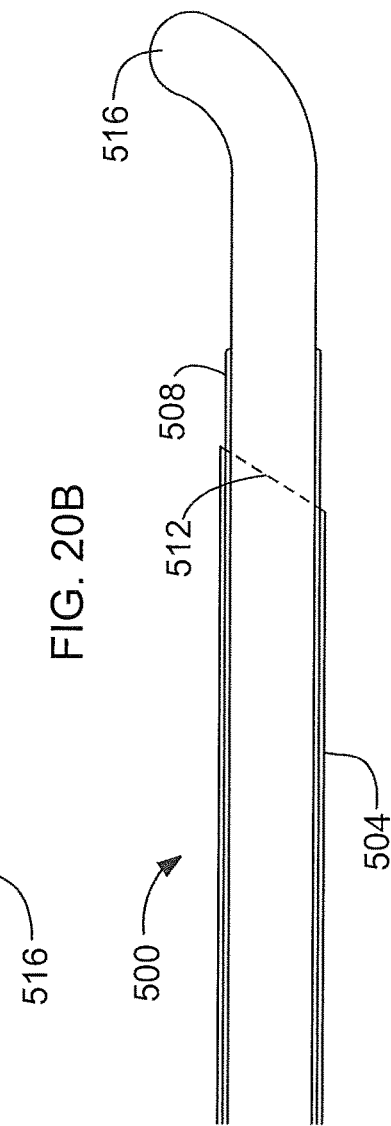
FIG. 20C illustrates the exemplary embodiment of the introducer system of FIG. 20A with a guidewire being deployed through an inner lumen of the introducer system.

FIGS. 20A-20C illustrate an exemplary embodiment of an introducer system/assembly 500 suitable for interventional cardiology procedures. The introducer system/assembly 500 may be included as part of the anchoring systems or systems for setting an anchor described herein. The introducer system/assembly 500 may comprise a needle or needle catheter 504 and an introducer 508 disposed within an inner lumen of the needle catheter 504. The needle catheter 504 may comprise a beveled edge 512 or other sharpened edge/tip suitable for puncturing tissue. As shown in FIG. 20A, the introducer 508 may be disposed within the needle catheter 504 such that a portion of the introducer 508 extends distally beyond the beveled edge 512. The distal portion of the introducer 508 may comprise an atraumatic and/or blunt shape (e.g., rounded, partially rounded, flat, etc.) so as to operate as an atraumatic distal end of the introducer system 500 during delivery of the needle catheter 504 to the site of a puncture, as well as removal therefrom.

A spring or other biasing mechanism (not shown) may be included as part of the introducer system/assembly 500. The spring or other biasing mechanism maintains/biases the introducer 508 such that a distal portion of the introducer extends distally beyond the beveled edge 512, e.g., as shown in FIG. 20A. Upon applying pressure to the introducer 508, such as due to pushing the needle catheter 504 distally against a tissue, the introducer may be pushed/slid proximally into the needle catheter 504, thereby exposing the beveled edge 512 or other sharpened edge/tip as shown in FIG. 20B. Once exposed, the beveled edge 512 is suitable for puncturing tissue, such as muscle tissue, so as to provide access to a cavity or structure. e.g., in the heart. The introducer 508 returns to the distally extended position shown in FIG. 20A upon entering into the cavity, thereby preventing the beveled edge 512 from damaging sensitive structures within the cavity or nearby tissues. It is contemplated that in some embodiments, springs exhibiting different degrees of spring force may be incorporated into the introducer system/assembly 500, and thus the springs may be selected according to a known level of force required to penetrate a particular tissue (e.g., to prevent tissue puncture in some tissues, but allow tissue puncture in other harder tissue). Further, in some embodiments, the introducer system/assembly 500 may include a lock or locking feature that allows the introducer 508 be locked into the distally extended position so as to enable pushing against tissue without the beveled edge 512 puncturing the tissue, e.g., by preventing the introducer 508 from moving proximally in the needle catheter.

The introducer system/assembly 500 may also include a guidewire 516. The introducer 508 may comprise an inner lumen which accommodates a guidewire 516. As shown in FIG. 20C, the inner lumen in the introducer 508 facilitates advancing the guidewire 516 without requiring the introducer 508 to be withdrawn from the needle catheter 504. Thus, the inner lumen enables the guidewire 516 to be advanced while the introducer 508 protects adjacent tissues from damage from the beveled edge 512. Further, the inner lumen enables the needle catheter 504 and the introducer 508 to be retracted together from the tissue or cavity while the guidewire 516 is left remaining in the deployed position. As will be appreciated, delivery of the guidewire 516 through the inner lumen of the introducer 508 substantially eliminates injury to nearby structures and tissue that might otherwise occur due to the presence of the beveled edge 512 in absence of the introducer. Further, having a lumen through the introducer 508 saves time and the extra step of having to retract the introducer 508 or a similar component from the needle catheter prior to advancement of a guidewire or other instruments therethrough.

Figure 21A:
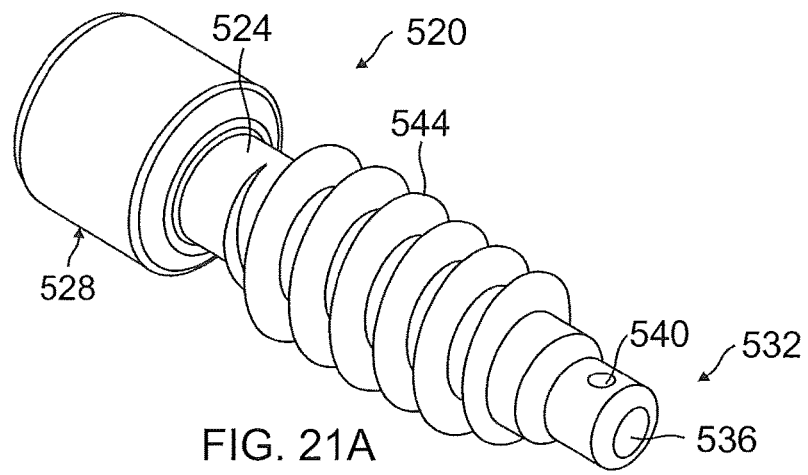
FIG. 21A is a perspective view illustrating an exemplary embodiment of a threaded introducer suitable for use during treatment of a dilated heart and/or functional mitral valve regurgitation.
Figure 21B:
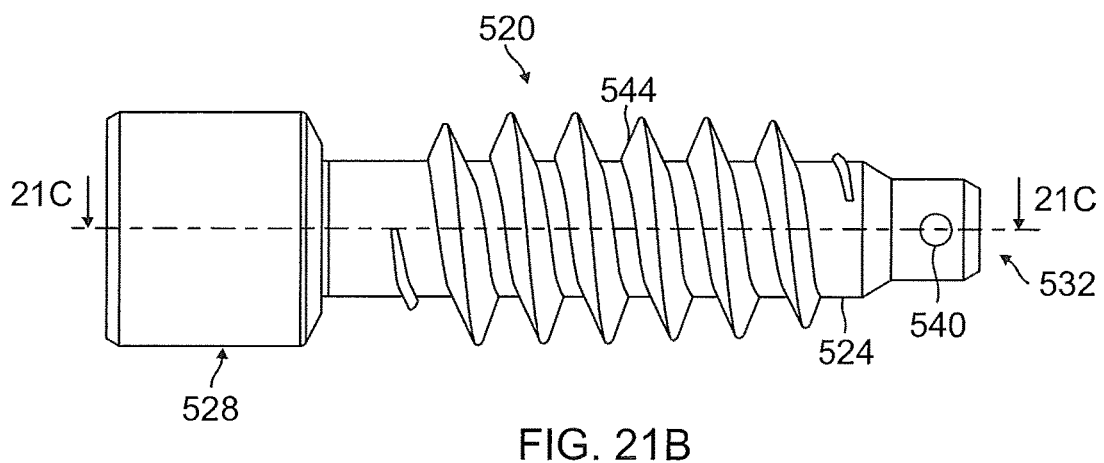
FIG. 21B is a side plan view of the exemplary embodiment of the threaded introducer illustrated in FIG. 21A.
Figure 21C:
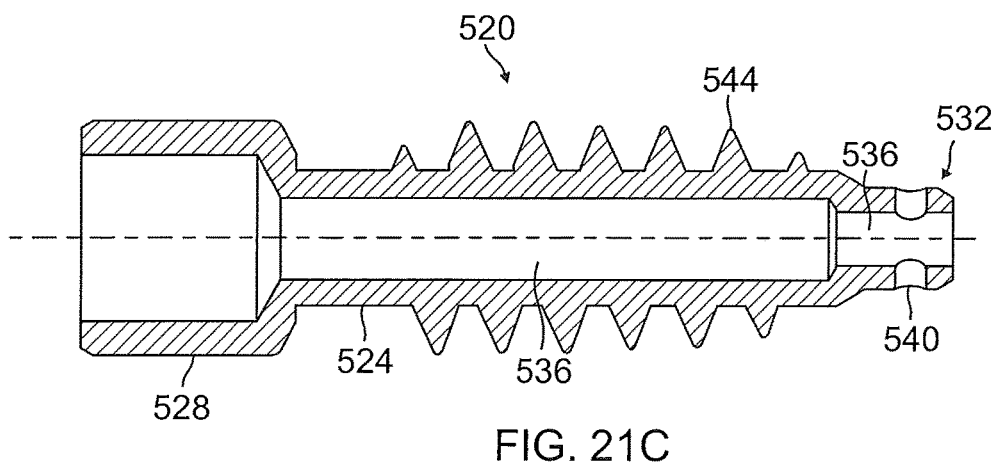
FIG. 21C is a cross-sectional view taken along a midline of the threaded introducer illustrated in FIG. 21A.

FIGS. 21A-21C illustrate an exemplary embodiment of a threaded introducer 520 suitable for use during medical treatment. The threaded introducer 520 may be particularly effective when used in moving tissue, e.g., in a beating heart. The threaded introducer 520 may be included as part of an anchoring system or system for setting an anchor. The threaded introducer 520 may be used in treating heart dilation (e.g., left ventricle dilation) and functional mitral valve regurgitation (FMR) as described herein. The threaded introducer 520 comprises a generally elongate shaft 524 having a proximal head 528 and a distal end 532. The proximal head 528 and/or the distal end 532 may include smooth, atraumatic surfaces so as to prevent damage to tissues and structures during delivery of the threaded introducer 520. A central lumen 536 may extend the full length of the threaded introducer 520 from the proximal head 528 to the distal end 532. As can be seen in FIG. 21C, the proximal head 528 and the portion of the central lumen 536 therein may be configured to fixedly receive a distal end of a catheter or other instrument. The threaded introducer 520 and the central lumen 536 may be configured for contrast injection therethrough to facilitate observation of the position of the threaded introducer 520, surrounding, tissues, and/or other instruments during treatment of a patient. The threaded introducer 520 may be configured for power injection of contrast fluid as well, e.g., the threaded introducer and/or its lumen may be reinforced or structured to withstand high pressures typical of power injection. Further, the distal end 532 comprises a distal tip opening and one or more than one lateral port 540 in fluid communication with the central lumen 536. As will be appreciated, the lateral port 540 operates to further enhance contrast injection along the sides of the threaded introducer 520. Contrast injection by way of the lateral port 540 and the central lumen 536 may provide improved imaging of surround tissue and/or accurate location and depth information during advancing the threaded introducer 520 within the heart 108.

The elongate shaft 524 may comprise one or more threads 544 disposed along the length of the threaded introducer 520. The threads 544 facilitate rotatably engaging the threaded introducer 520 within a tissue, such as by way of non-limiting example, the myocardium of the heart 108. During operation of the threaded introducer 520, rotating the catheter shaft, whether flexible or rigid, causes the threaded introducer 520 to turn whereby the threads 544 become engaged with the myocardium. As the threaded introducer 520 continues turning, the threads 544 draw the threaded introducer deeper into the myocardium, effectively "screwing" the threaded introducer 520 into the myocardium. It will be appreciated, that the threads 544 advantageously eliminate a need for a pushing force that is typically required to puncture the myocardium by way of a needle or trocar. Further, the threaded introducer 520 is particularly advantageous for delivering a catheter into a moving tissue, such as by way of non-limiting example, a beating heart 108. As will be recognized, depth control and location identification often are nearly impossible to observe and control when pushing a needle, catheter, trocar, or other puncturing instrument into a beating heart. The threads 544, however, prevent the tissue from moving relative to the threaded introducer 520 until the surgeon further rotates the catheter shaft. Thus, the threaded introducer 520 provides very accurate depth control during delivery into the beating heart, as well as providing an essentially self-advancing catheter. This also help prevent damage to external or surrounding tissues that might otherwise be damaged as the tissue moves and the physician attempts to puncture the moving tissue.

As stated above, the threaded introducer 520 is particularly well-suited for use during treatment of FMR, wherein it is desirable to cross the septum 132 and the myocardium with a medium size catheter, such as a 10 French-sized catheter. For example, after passing through the septum 132, the threaded introducer 520 may be advanced across the left ventricle 116 to the posterior wall. A needle may be advanced through the central lumen 536 so as to create a surface puncture in the posterior wall to receive the distal end 532. Once the distal end 532 enters the puncture, carefully rotating the catheter shaft screws the threaded introducer 520 into the posterior wall without crossing all the way through the myocardium. Contrast injection may be performed by way of the central lumen 536 and the lateral port so as to help image the area and judge the depth and location of the threaded introducer 520 and/or to view the surrounding tissue and/or other instruments used. In one embodiment, an ultrasound/echo probe may also or alternatively be used. Upon further rotating the catheter shaft, the surgeon may slowly advance the threaded introducer 520 and the catheter through the myocardium into the pericardial cavity without piercing the pericardium. It should be recognized that the smooth surfaces of the threaded introducer 520 and the threads 544 may provide a controlled crossing of the myocardium without damaging the pericardium, the coronary arteries, or other surrounding tissue.

As will be appreciated, some treatments may require passing the catheter beyond the pericardial cavity, and thus call for puncturing the pericardium. Once in the pericardial cavity, the threaded introducer 520 may be advanced to a desired puncture site on the pericardium. A needle may be delivered through the central lumen 536 so as to carefully create a puncture in the pericardium to receive the distal end 536. The catheter shaft may be rotated to engage the threads 544 with the pericardium and then advance the threaded introducer 520 and the catheter shaft through the pericardium. The smooth surfaces of the distal end 532 and the proximal head 528 ensure that the threaded introducer 520 advances beyond the pericardium without damaging the lungs or other nearby organs and tissues of the patient.

Figure 22A:
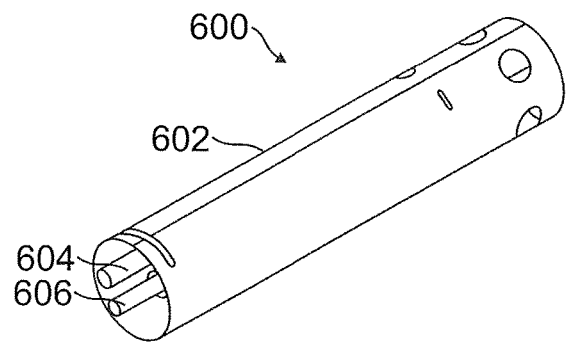
FIG. 22A is a perspective view illustrating illustrate an exemplary embodiment of a suture cutter catheter suitable for use during medical treatment.
Figure 22B:
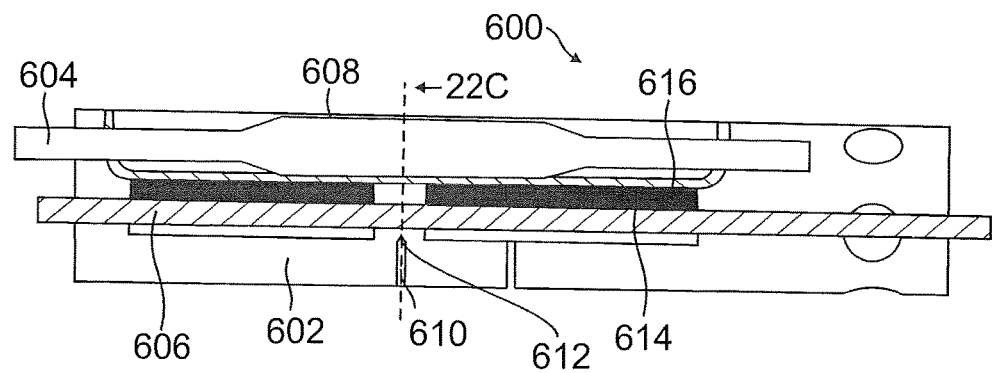
FIG. 22B is an internal side view of the exemplary embodiment of the suture cutter catheter illustrated in FIG. 22A.
Figure 22C:
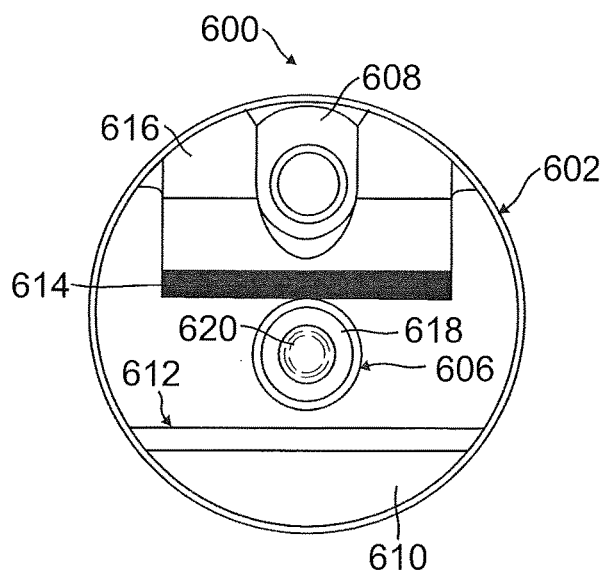
FIG. 22C is a cross-sectional view of a portion of the suture cutter catheter illustrated in FIG. 22A.

FIGS. 22A-22C illustrate an exemplary embodiment of a cutting catheter or cutter catheter 600 (e.g., a suture cutter catheter) suitable for use during medical treatment. The cutter catheter 600 may be included as part of an anchoring system or system for setting an anchor as described herein. The cutter catheter 600 may be used in various treatments, including treating dilation and functional mitral valve regurgitation (FMR) as described herein. For example, the cutter catheter 600 may be a suture cutter catheter used to cut sutures that are implanted to seal and/or repair punctures, holes, cuts, or other tissue damage from the medical treatment (e.g., from the FMR treatment). The cutter catheter 600 may comprise one or more of the following: an outer tube 602, an inflation tube 604, a positioning tube 606, a balloon 608, a cut blade 610, a moving plate 614, a spring 616, and/or other components. The outer tube 602 may be formed of a rigid or semi-rigid material and may contain one or more of the other components of the cutter catheter 600. In one embodiment, the outer tube 602 may contain the entire cutting mechanism of the cutter catheter 600. FIG. 22B shows an interior view of the suture cutter catheter 600 and reveals exemplary components of a cutting mechanism contained in the outer tube 602. FIG. 22C shows a cross sectional view of the cutter catheter 600 taken along the dotted line labeled 22C in FIG. 22B.

The cutter catheter 600 may be assembled inside of a long, flexible catheter shaft. In one embodiment, the outer tube 602 is a long, flexible catheter shaft or a portion of a long, flexible catheter shaft. In one embodiment the outer tube 602 is arranged inside a portion of a separate long, flexible catheter shaft, e.g., in a distal end of the long, flexible catheter shaft. The outer tube 602 may be fixedly attached inside a long, flexible catheter shaft, or may be delivered in a long, flexible delivery catheter to the cutting location. Advantages of the cutter catheter 600 include, without limitation, (1) "unlimited" length, i.e., any length may be used (e.g., the cutter catheter 600 can effectively cut a suture at the end of a very long catheter or tube a long distance into a body), (2) "unlimited" flexibility, i.e., the catheter may have any range of flexibility (e.g., the cutter catheter 600 or a portion thereof can itself be very flexible or the cutter catheter 600 can be delivered/advanced inside a separate, but very flexible catheter, such that the cutter catheter 600 may be navigated through a tortuous path in the body and used a long distance into the body of a patient, and (3) application of a high, controlled force (e.g., the mechanism allows for a high, controlled cutting force even at a remote location a long distance in the body or a long distance from the proximal end of the catheter).

The suture cutter catheter 600 may include a balloon 608 that may be inflatable by a fluid, e.g., by air, water, saline solution, etc. The balloon may be located between a first side of the inner wall of the outer tube 602 and a moving plate 614. Inflation tube 604 may include a lumen in fluid communication with the balloon 608. The inflation tube 604 may be configured for connection to an elongate tube or catheter connected to a fluid source and/or for connection directly to a fluid source. Fluid may flow from the fluid source to the inflation tube 604 and into the balloon 608 to inflate the balloon 608. In one embodiment, the fluid source is high pressure syringe, e.g., as used to inflate coronary balloons. When inflated, the balloon 608 may expand and thereby cause the moving plate 614 to move toward the cut blade 610, which may be located on a second side of the inner wall of the tube, e.g., opposite the balloon 608. The moving plate 614 may be a rigid or semi-rigid plate capable of firmly pressing a suture 620 or other material against the cut blade 610 to cut the suture 620 or other material. The blade 610 may be a sharp blade having a sharp edge 612 configured for easily and cleanly cutting a suture 620 or other material. The moving plate 614 may move toward the blade 610 until the moving plate 614 directly contacts the sharp edge 612 of the cut blade 610, thereby cutting/severing any suture or other material between the moving plate 614 and the blade 610. The moving or pressing force that moves the moving plate 614 toward the blade 610 may be generated by inflating the balloon 608, e.g., by hydraulic action.

The suture cutter catheter 600 may also include a biasing component, mechanism, or spring 616 that biases the moving plate 614 away from the blade 610. The biasing component, mechanism, or spring 616 may connect between the moving plate 614 and the first side of the inner wall of the outer tube 602 opposite the blade 610, e.g., the spring 616 may connect directly to the moving plate 614 and to the first side of the inner wall of the outer tube 602. When the balloon 608 is inflated the moving plate 614 moves away from the first side of the inner wall toward the cut blade 610 thereby expanding/tensioning the biasing component, mechanism, or spring 616. The biasing component, mechanism, or spring 616 biases the moving plate 614 to move toward the first side of the inner wall away from the cut blade 610, so that after the pressing force is no longer supplied by the balloon 608 (e.g., when the balloon deflates or imparts less pressure), the moving plate 614 automatically moves away from the blade 610 or toward the first side of the inner wall of the outer tube 602.

The suture cutter catheter 600 may also include a positioning tube 606. Positioning tube 606 may be a polymer or plastic tube. Optionally, the positioning tube 606 may be constructed of a material that may be readily cut by the blade 610, and/or the positioning tube 606 may include a break or separation in the tube 606 in the region where the cut blade 610 contacts the moving plate 614 to ensure the positioning tube 606 does not interfere with cutting the suture 620 or other material. The positioning tube 606 may include a lumen 618 in which a suture 620 or other material to be cut may be received. The positioning tube 606 may be adhered, bonded, glued, or otherwise affixed to the moving plate 614 to ensure that a suture 620 or other material in the lumen 618 of the positioning tube may be properly positioned/located for cutting, e.g., to ensure a suture 620 or other material is in the proper location between the blade 610 and the moving plate 614 during cutting. The suture 620 or other material may be threaded through the positioning tube 606 before cutting to properly position the suture 620 or other material. For example, a free end of a suture may be threaded through a distal end of the positioning tube 606 and through the lumen 618. The positioning tube 606 may then be advanced along the suture to a point where the cut is desired. When properly positioned as desired, the balloon 608 may be inflated thereby pressing the moving plate 614 to the cut blade 610 until the suture 620 or other material is cut/severed by the cut blade 610. The suture cutter catheter 600 can make it easier to effectively cut thick, strong, or otherwise difficult to cut sutures, lines, members, etc. For example, the suture cutter catheter 600 is effective at cutting sutures, lines, members, etc. made from very strong fibers, like Dyneema fibers or strong Ultra High Molecular Weight Polyethylene (UHMWPE) fibers. The suture cutter catheter 600 could also be used to cut any excess unused portion of a tension member.

FIGS. 23A-23C illustrate an exemplary embodiment of a device 700 suitable for use during medical treatment and the methods described herein and which may be part of one or more of the systems described herein. The device/catheter 700 may be formed as a C-shaped device or catheter. The device/catheter 700 may be a puncture location device or puncture location catheter, and may be a multipurpose device that helps identify a puncture location, facilitates deployment of one or more anchors, and/or performs other functions. The device/catheter 700 may be included as a part of an anchoring system, as described herein. The device/catheter 700 may be used in a variety of treatments, including treating dilation and functional mitral valve regurgitation (FMR), as described herein. For example, the device/catheter 700 may be used as puncture location device/catheter to identify a desired puncture location and/or guide puncturing devices to create a puncture in the desired puncture location, e.g., a desired puncture location on a wall of an organ. For example, device/catheter 700 may be used to identify a puncture location and guide a puncturing device to location on a wall of a left ventricle of a heart and/or a posterior wall of the heart 108 that avoids or minimizes damage to the papillary muscles 144 or other vessels, tissue, etc., during medical treatment.

The device/catheter 700 may include a proximal handle 702, a positioning tube 704, and/or other features. Proximal handle 702 may facilitate gripping and moving the device/catheter 700. Proximal handle 702 may facilitate navigating the device/catheter 700 through an incision site and to a desired location. This may include navigating the device/catheter 700 around a portion of the heart or another organ, to a desired location/position. For example, proximal handle 702 may be used to direct/navigate the distal end of the device/catheter 700 around the region of a heart including the left ventricle 116 so as to position a distal end/region of the device/catheter 700 at a desired location along a wall of the heart (e.g., at a desired puncture location for puncture through the heart wall or a wall of the left ventricle). The device/catheter 700 may be used to help locate/identify a location outside a posterior side of the human heart 108 (e.g., a location along the posterior wall of the left ventricle at which puncturing would avoid or limit damage to blood vessels, papillary muscles, etc.). Pressing a portion of the device/catheter 700 (e.g., a guide portion 724 and/or a finger 706) into and/or moving the portion along a wall (e.g., posterior wall) of the human heart 108 (or another organ or portion of the body) may cause a bend or bulge in the wall of the heart (or other organ or portion of the body) that is detectable/viewable by way of an epicardial echo probe or ultrasound probe or another imaging device. The device/catheter 700 may thereby enable a surgeon to identify a location on an organ, heart, or portion of the body that is suitable for being punctured during medical treatment (e.g., during FMR treatment) without causing undue damage (e.g., avoiding undesired damage to vessels, papillary muscles, and/or tissue structures within the left ventricle 116 of a heart).

In the embodiment illustrated in FIGS. 23A-23C, the device/catheter 700 includes a positioning tube 704. Positioning tube 704 can be formed and configured as a generally long, thin tube having a shape suitable for being directed into an incision site and navigated around a portion of a heart or other organ to a desired location, e.g., around the exterior of a left ventricle 116 to the posterior side of the left ventricle 116 of a heart 108. The positioning tube 704 may be comprised of an elongate portion 708 and a curved portion 712 that may be connected together (or connectable together). For example, elongate portion 708 and a curved portion 712 may be connected or be connectable by way of a proximal bend 716. In one embodiment, the positioning tube 704 may be comprised of a single-piece, integral component that may be suitably manipulated/shaped/molded/etc. to form the curved portion 704 and the proximal bend 716. In one embodiment, the positioning tube 704 may be comprised of several separate tube segments that may be individually molded, manipulated, or fabricated and then adhered, bonded, glued, or otherwise assembled to form the shape of the positioning tube 704 illustrated in FIGS. 23A-23B.

The curved portion 712 may comprise a radius of curvature suitable for extending around the left side of the human heart 108 or for extending around another organ or portion of a body. An elbow portion 720 and a guide portion 724 may be included at a distal end/region of the positioning tube 704. The elbow 720 may be disposed at a distal end of the curved portion 712. The guide portion 724 may be disposed at a distal end of the elbow 720 or an end opposite the curved portion 712. The elbow 720 and/or the guide 724 may be adhered, bonded, glued, or otherwise affixed to the distal end of the curved portion 712. Though, in one embodiment, an elbow portion the same as or similar to elbow 720 and/or a guide portion the same as or similar to guide portion 724 could be made/formed integral with other portions as part of a single-piece positioning tube or device/catheter. In one embodiment, the elbow 720 imparts a 90-degree bend to the distal end of the curved portion 712, such that the guide 724 is oriented toward, and aligned with, a longitudinal axis 728 of the elongate portion 708, as shown for example in FIG. 23B.

Guide portion 724 may be formed in a variety of sizes and shapes. In one embodiment, the guide portion 714 may be columnar or generally columnar in shape. A front region of guide 724 (e.g., opposite the elbow 720 and/or facing toward the elongate portion 708) may be pressed or pulled against a portion of an organ or part of the body (e.g., a heart) and may cause a bending or bulging in the wall that may be visible with an echo probe or ultrasound probe or other imaging equipment. Doing this may help a user to identify and mark a desired puncture or treatment location on the organ or part of the body (e.g., on a wall of a heart). Guide portion 724 may include a concave or inwardly tapered front region (e.g., on the end opposite elbow portion 720). This front region may be curved into a concave or generally concave region or may be tapered inwardly to form a conical or generally conical region within the front end of the guide 724. This concave or inwardly tapered front region may help receive a puncturing device through the organ or part of the body, e.g., the concave or inwardly tapered front region may help guide and receive a needle or other puncture device passing through a wall of the heart. If the device/catheter 700 has only a single lumen (though some embodiments may have more) and no finger 706, applicator 732, or device connecting these are used (i.e., if these do not block the lumen of the device), then the lumen may be used to help deploy and/or use an anchor or other medical device to the puncture/treatment location. For example, a tension member of an anchor may be passed through the lumen and may be snared by the puncturing device or another device that passes through the puncture, then the puncturing device or snare may be withdrawn through the puncture bringing the tension member with it and leaving the anchor deployed outside the puncture.

The device/catheter 700 may also include a finger 706, which may be coupled with guide portion 724 and/or may reside partially or fully within guide portion 724. Finger 706 may be configured in a variety of shapes and sizes, e.g., columnar, conical, rounded, flat, curved, and many more. Finger 706 may be thick or thin and may be solid or hollow. In one embodiment, the finger 706 may be oriented toward, and aligned with, a longitudinal axis 728 of the elongate portion 708, as shown in FIG. 23B. The alignment of the finger 706 with the longitudinal axis 728 of the elongate portion 708 may help enable the surgeon to use/manipulate the proximal handle 702 such that the device/catheter 700 may be used to determine a location and orientation of the guide 724 and/or finger 706 (e.g., when located near an organ or, for example, near the posterior side of the human heart 108).

A front region of finger 706 (e.g., facing away from the elbow 720 and/or facing toward the elongate portion 708)

may be pressed or moved against a portion of an organ or part of the body (e.g., a heart) to identify and mark the desired puncture or treatment location on the organ or part of the body (e.g., on a wall of a heart). The finger 706 may be slidably coupled with the guide 724. The finger 706 may be configured and designed to be movable and/or may be configured and designed to be transitionable between two or more configurations. Transitioning between the configurations or moving the finger may help the user to identify the location of the finger 706 when viewing the organ or portion of the body (e.g., heart) with an echo probe or ultrasound probe or other imaging equipment, e.g., movement or transitioning of the finger may cause portions of an organ or heart to bend, bulge, or move in a way that can be seen with imaging equipment. If used to identify a desired puncture location on a heart, pressing the finger 706 into and/or moving the finger 706 along the side or wall of the heart may cause a slight bend or bulge in the wall of the heart that may be detectable/viewable by way of an epicardial echo probe or ultrasound probe or other imaging equipment. The finger 706 may thereby aid a surgeon in identifying a location on the wall that is suitable for being punctured (e.g., during FMR treatment) without causing damage to vessels, papillary muscles, and/or tissue structures within the left ventricle 116.

Finger 706 may be configured to retract entirely within the guide 724 or to have a portion of the finger 706 that remains outside the guide 724. In one embodiment, finger 706 may be a wire, a wire-like device, or may be another long, narrow device that can extend from the guide 724 or retract within the guide 724. In one embodiment, finger 706 may be columnar or generally columnar and may act similar to a column or button that pushes out from the guide 724 to contact and press against an organ or part of the body. In one embodiment the finger 706 may have a diameter similar to or slightly less than the guide 724. The finger 706 may slide within the guide 724 to extend out from or retract within the guide 724 and thereby transition between an extended configuration and a retracted configuration. In one embodiment, the finger 706 may include a portion with a larger diameter or width that remains outside the guide 724 (e.g., between the guide 724 and elongate portion 708) and a portion with a smaller diameter or width that slides within and partially outside the guide 724 to transition the finger 706 between an extended configuration and retracted configuration. A larger diameter region of a finger 706 may be conical or generally conical in shape (e.g., may have a region with a continuous transition from a larger diameter to a smaller diameter).

Finger 706 and/or guide 724 may include a concave or inwardly tapered front region (e.g., on the end facing away from elbow portion 720 and toward elongate portion 708). This front region may be curved into a concave or generally concave region or may be tapered inwardly to form a conical or generally conical region within the front end of the finger 706 or guide 724. This concave or inwardly tapered front region may help receive a puncturing device through the organ or part of the body, e.g., the concave or inwardly tapered front region may help guide and receive a needle or other puncture device passing through a wall of the heart.

The finger 706 may be moved and/or transitioned between configurations (e.g., extended and retracted) by way of a long, flexible catheter shaft, wire, tube, pusher, etc. that extends from the finger 706 to an applicator 732, which applicator 732 may be disposed near the proximal end of the catheter/device 700 or near handle 702. The catheter shaft, wire, tube, pusher, etc. may be routed from the finger 706, within a lumen of the curved portion 712, and to the applicator 732. An actuator tube 736 may act as the flexible catheter shaft, wire, tube, pusher, etc. that extends through the curved portion 712 to the finger 706 to cause the finger 706 to move or transition between configurations, or the actuator tube 736 maybe provide a connecting lumen through which the flexible catheter shaft, wire, tube, pusher, etc. passes from the applicator 732 to the curved portion 712. The actuator tube 736 may be slidable within or otherwise connected, adhered, bonded, glued, or affixed to the curved portion 712 to ensure that the finger 706 moves as directed by movement of the applicator 732 (e.g., a user should be able to move the applicator 732 to cause the finger to move or transition between configurations).

The device/catheter 700 may further include a spring, or other biasing component, that biases the finger 706 to a retracted configuration (e.g., biases the finger 706 toward or within the guide 724 and/or elbow 720). In one embodiment, the spring may be coupled between the applicator 732 and the actuator tube 736 and/or within the applicator 732, such that when a pressing force is applied to the applicator 732, the spring is compressed and the flexible catheter shaft, wire, tube, pusher, etc. moves distally and pushes the finger 706 to an extended configuration (e.g., such that the finger 706 can push against a wall of a heart, organ, or other part of the body). In one embodiment, the spring may bias the applicator 732 or a portion of the applicator 732 proximally away from the actuator tube 736, such that after the pressing force is no longer applied to the applicator 732 the spring automatically moves the flexible catheter shaft proximally and pulls the finger 706 toward and/or within the guide 724. It should be understood that the spring, or other biasing component, is not to be limited to being disposed between the applicator 732 and the actuator tube 736, but rather the spring, or other biasing component may be disposed in any location of the puncture location catheter 700 that is suitable for biasing the finger 706 toward the guide 724, as described herein. For example, in one embodiment, the spring or biasing component may be disposed within the guide 724.

In one embodiment, e.g., as shown in FIGS. 23A-23C, the long, thin positioning tube 704 may comprise at least one interior lumen that is dedicated to routing the flexible catheter shaft, wire, tube, pusher, etc. from the applicator 732 to the finger 706, as described above. In one embodiment, the positioning tube 704 may comprise more than one interior lumen, e.g., two, three, or four interior lumens, without limitation. In one exemplary embodiment, the positioning tube 704 may comprise at least (1) a first lumen that may be used to direct the flexible catheter shaft, wire, tube, pusher, etc. to the finger 706, as described herein, and (2) a second lumen that may be used to help deploy an anchor (e.g., the superior anchor 136) or other medical device during medical treatment. For example, during FMR treatment, the finger 706 through the first lumen may be used to help guide a needle catheter (e.g., a 4 or 5 French-sized needle catheter) or other puncturing device to puncture wall of the heart 108 (e.g., to puncture a wall of the left ventricle 116) in a desired puncture location, and the second lumen may be used to deploy a tension member (e.g., tension member 128) and an anchor (e.g., superior anchor 136) to the puncture site. For example, a tension member of an anchor may be passed through the second lumen and may be snared by the puncturing device or another device that passes through the puncture, then the puncturing device or snare may be withdrawn through the puncture bringing the tension member with it and leaving the anchor deployed outside the puncture. Similarly, if two lumens are not included within device/catheter 700, multiple separate single lumen devices could be used in a similar way, e.g., the lumen of the first device may help control a finger 706, and the lumen of a second device may aid in deployment and/or use of an anchor or other medical device.

In one embodiment, upon withdrawing the puncturing device/needle from the catheter, a snare may be inserted into the catheter and directed through the puncture in the organ (e.g., the puncture in a wall of the heart 108) to capture an end of the tension member 128 extended or pushed out of a lumen (e.g., a second lumen of device/catheter 700). The snare may then be used to draw the tension member 128 through the wall of the organ/heart and to pull the superior anchor 136 from the second lumen into contact with the exterior of the posterior wall of the heart 108. The tension member 128 extend across the left ventricle 116, through the wall of the septum 132 to an inferior anchor deployed at the septum, or through the wall of the septum 132 and across the right ventricle 120 to an inferior anchor outside the right ventricle. The inferior anchor may be mounted onto and/or connected to the end of the tension member 128 and may be positioned adjacent to the right ventricle 120 (e.g., external to the heart outside the right ventricle as shown in FIGS. 1-2) or may be positioned inside the right ventricle against the wall of the septum 132. The inferior anchor 140 may be cinched or otherwise locked/attached onto the tension member 128 to impart an advantageous shape change to the heart and/or annulus of the mitral valve 112, as well as to advantageously reposition the papillary muscles 144, as described herein.

Various methods of medical treatment, methods of treating dilation (e.g., left ventricle dilation) and/or mitral valve regurgitation, methods of implanting and/or securing a mitral valve splint, and other methods are possible and contemplated using one or more of the systems, apparatuses, devices, steps, etc. described above. Also, various parts of the body (including, but not limited to, the heart) may be treated using one or more of the systems, apparatuses, devices, steps, etc. described above. For example, the various puncturing instruments/devices described may be used in many different applications to puncture a wide variety of tissue/body parts in various types of medical treatments. Steps described above and below with respect to the various methods, systems, apparatuses, assemblies, devices, etc. herein may be used in various combinations.

Methods of medical treatment, methods of treating a heart condition, methods of implanting and securing a mitral valve splint, and/or other methods may include any of the steps disclosed herein. For example, methods of treating a heart condition (e.g., left ventricle dilation, mitral valve regurgitation, etc.) may include accessing the heart or one or more portions of the heart (e.g., accessing a right ventricle of the heart). Accessing the heart may be done by first making one or more than one incisions to the body (e.g., the skin) to form one or more than one access points. The access point(s) may be near the chest and/or heart of a patient or may be remote from a patient's chest or heart (e.g., in an arm or leg or neck). Methods may include inserting an instrument into the access point, moving the instrument to the heart, and entering a portion of the heart (e.g., entering the right ventricle). Entering the heart may be by way of an incision, puncture, hole, etc. in a portion of the heart, e.g., by an incision, puncture, hole, etc. in a wall of the right ventricle. Optionally, entering the heart may be done by first entering a blood vessel, then advancing/inserting a medical instrument (e.g., a catheter or other instrument/device/apparatus/assembly described herein) through the blood vessel and into a portion of the heart (e.g., the right ventricle).

Methods may include inserting/advancing a needle catheter (e.g., the same as or similar to needle catheter 504) into the right ventricle of the heart, then through the septum between the right ventricle and the left ventricle. A blunt tip introducer (e.g., the same as or similar to introducer 508) may be inside the needle catheter and a blunt distal end of the introducer needle may be positioned near the posterior/left wall of the heart (i.e., the wall between the left ventricle and the pericardium). Methods may include passing a guide wire through a guidewire lumen in the introducer (e.g., introducer 508). Imaging techniques can be used at various stages of treatment, including to guide the needle catheter to the correct puncture points and/or may be used to position a threaded introducer (e.g., the same as or similar to threaded introducer 520) in the proper location in the posterior/left wall of the heart. The imaging techniques can include introducing one or more contrast solutions through the introducer and using an imaging system to view the contrast solution in the heart. The imaging techniques can also include using an inserted echo or ultrasound probe to view portions of the treatment area (e.g., walls of the heart, puncture devices, an introducer, a finger/guide of a puncture location device, etc.). In one embodiment, a threaded introducer (e.g., the same as or similar to threaded introducer 520) may be advanced to the posterior/left wall of the left ventricle and may be rotated into the left wall of the heart such that the rotation of the threads pulls the threaded introducer into the wall in a controlled manner and anchors the threaded introducer in the left wall. In one embodiment, another conduit, introducer, catheter, needle, puncturing device, etc. could be used to create an incision/puncture through the wall of the organ or heart. A guidewire may be advanced through the introducer, threaded introducer, conduit, needle, and/or an incision/puncture in the wall of the heart (e.g., a posterior and/or left wall).

Methods may comprise advancing a distal end of the delivery catheter over the guidewire and through an introducer (e.g., the threaded introducer), conduit, and/or incision/puncture into the pericardium cavity or outside of the pericardium. The delivery catheter may be loaded with an anchor (e.g., the same as or similar to any of the anchors described above and/or shown in one or more of FIGS. 3A-11B). The anchor or a ring/wire of the anchor may be constructed of a shape memory material. The shape memory material ring/wire may be essentially collapsed, linear, and/or straightened in the delivery catheter, but may automatically become ring shaped (or assume a shape of one of the other anchors described above) when moved out of the lumen of the delivery catheter. The anchor may include a cover and/or a strip/strips of a material (e.g., PET, PTFE, etc.) that have a first end through which the shape memory material is threaded and a second end through which a tension member or pull cord (e.g., the same as or similar to the tension members described above) is threaded. When the anchor is deployed from the catheter and regains its ring shape, the tension member or pull cord may be pulled such that the inner area of the ring is filled with the material (e.g., PET, PTFE, etc.) such that the anchor resembles a disc shape and the cover material is straightened or tensioned to a flattened configuration (e.g., a substantially or roughly flattened configuration), and/or the tension member may pull the cover or a portion of the cover into a cone-like shape (e.g., as the tension member is pulled away from the anchor). In one embodiment, the anchor may be a manually expandable anchor, e.g., similar to the manually expandable anchors discussed above, and may be expanded or deployed as discussed above. Methods may also include deploying a second anchor on the right or front side of the heart or pericardium (e.g., outside the right ventricle) or may include deploying the second anchor inside the right ventricle against a portion of the septum or septal wall. Methods may also include cinching the first and second anchors toward each other so as to contract the size/shape of the heart (or a portion of the heart) and ensure that the leaflets of the mitral valve properly overlap with each other to prevent mitral valve regurgitation.

The methods disclosed herein may also comprise using an echo or ultrasound probe (e.g., a trans-vaginal ultrasound probe or an ultrasound probe designed for use in treatment of dilation, mitral valve incompetency, mitral valve regurgitation, and other similar conditions) to assist during treatment of conditions of the human heart. The echo/ultrasound probe may have a guide attached thereto, the guide may be configured for or be capable of guiding the delivery catheter to a desired location in the body or heart. The echo/ultrasound probe and guide may be part of an anchoring system or system for setting an anchor described herein. The methods and/or steps described elsewhere herein may be performed in conjunction with using the echo/ultrasound probe, e.g., to identify treatment sites/locations, to navigate the medical instruments/devices to a desired treatment site/location, and/or view the medical instruments/devices as they are used in a remote location in the body.

The methods may comprise loading a medical instrument (e.g., a trocar, trocar catheter, needle, needle catheter, catheter, one of the instruments/devices described herein, etc.) into a guide of the ultrasound probe. The guide may be fastened to an ultrasound probe comprising an elongate shaft extending from a proximal handle to a distal end. The ultrasound probe may be inserted into a patient by way of an incision. The distal end of the ultrasound probe may then be navigated to a location adjacent to an exterior surface of the heart and/or pericardium. A treatment site may be identified on an exterior surface of the heart and/or pericardium using an image(s) (e.g., a live/real-time image) obtained using an ultrasound transducer disposed within the distal end of the ultrasound probe. The medical instrument may be advanced within the guide to the treatment site, and the condition of the heart may be treated. The medical instrument may also be withdrawn from the treatment site. In one embodiment, the method involves using a trans-vaginal ultrasound probe for imaging in the heart. The trans-vaginal ultrasound probe can be used for navigation during the methods and/or steps described herein and to position the introducer correctly in the heart wall. The trans-vaginal ultrasound probe may be smaller than a typical epicardial echo probe. A guide may be included on the trans-vaginal ultrasound probe to connect a puncture needle or the needle catheter thereto to allow parallel insertion of the needle catheter with the ultrasound probe.

In one embodiment, a method for medical treatment (e.g., for treating dilation and mitral valve regurgitation) may comprise: inserting a catheter, a puncturing instrument (e.g., a trocar, trocar catheter, needle, needle catheter, curved needle, introducer, introducer assembly, a sharpened portion of an assembly, etc.) having a sharpened distal tip, guidewire, assembly, and/or other instrument into a right ventricle of a heart (e.g., a beating heart) of a patient. A guidewire may be inserted into the right ventricle before other instruments, and then other instruments may be passed over the guidewire into the right ventricle. Inserting the catheter, puncturing instrument, guidewire assembly, and/or other instrument into the right ventricle of the heart may be accomplished by passing the catheter, puncturing instrument, guidewire, assembly, and/or other instrument through an incision/puncture (e.g., made using a scalpel, introducer, introducer sheath, needle, other puncturing instrument) in a wall of the right ventricle (e.g., a right and/or anterior wall). Access to the wall of the heart may be accomplished via an incision/puncture in the chest near the heart (e.g., a small hole in the 4th inner costal, optionally, 5-7 mm in diameter).

Optionally, inserting the catheter, puncturing instrument, guidewire, assembly, and/or other instrument into the right ventricle of the heart may be accomplished by first passing the catheter, puncturing instrument, guidewire, assembly, and/or other instrument through an incision/puncture in a blood vessel at a point removed/apart from the heart and navigating the catheter, puncturing instrument, guidewire, assembly, and/or other instrument through the blood vessel and into the right ventricle. For example, this could be accomplished by passing the catheter, puncturing instrument, guidewire, assembly, and/or other instrument into a subclavian, innominate vein, superior vena cave (SVC), or inferior vena cava (IVC), e.g., in the region of the neck, clavicle, or upper chest, and navigating the along the vessel through the right atrium, through the tricuspid valve, and into the right ventricle. Incision/puncture locations at various points in the heart may be identified in advance or during operation with imaging equipment.

An inserted catheter may be a directional catheter that is inserted into the right ventricle as discussed above. The directional catheter may be able to transition between a straight or generally straightened configuration to navigate to the right ventricle, then may be transitioned to an angled, bent, or curved configuration to help guide and direct an instrument (e.g., a puncturing instrument) passing through the directional catheter at the septum. This allows the puncturing instrument to curve, bend, or angle toward the septum and puncture the septum as desired, even when inserted from a region remote from the heart.

An inserted assembly may be a septum-puncture assembly that is inserted into the right ventricle as discussed above. The septum-puncture assembly may include a catheter or portion similar to a directional catheter to direct/guide a puncturing instrument at the septum, or may include a permanently angled or curved portion to direct/guide the puncturing instrument at the septum. The septum-puncture assembly may also be or include a stabilization assembly to stabilize the assembly and/or a puncturing instrument in the right ventricle for puncturing the septum. The septum-puncture assembly or stabilization assembly may be the same as or similar to septum-puncture/stabilization assemblies described elsewhere herein (e.g., the assemblies shown in 12A-14C). This assembly may allow a puncturing instrument to curve, bend, or angle toward the septum and puncture the septum as desired, even when inserted from a region remote from the heart. The method may include puncturing a septum of the heart (e.g., the septum between the right ventricle and a left ventricle of the heart) with a puncturing instrument.

The method may include identifying a desired puncture location on a wall of the heart (e.g., on a wall of the left ventricle). A device/catheter (e.g., C-shaped device/catheter or a puncture-location device/catheter, which may be the same as or similar to other such devices/catheter described elsewhere herein and/or shown in FIGS. 23A-23C), may optionally be used to identify the desired puncture location. The device/catheter may be inserted through an incision on the chest of a patient and navigated around a portion of the heart (e.g., to a posterior wall of the left ventricle). Identification of the desired puncture location may be done by moving, pressing, pulling, etc. a portion of the device/catheter against a wall (e.g., an external wall) of the heart while viewing the wall of the heart with imaging equipment (e.g., an echo or ultrasound probe). The moving, pressing, pulling, etc. of the device/catheter may be done so as to cause the wall of the heart to bend or bulge in a manner that is visible on the imaging equipment. The catheter/device may include a movable finger to aid in moving or pressing against the wall of the heart. The method may involve transitioning the finger from a retracted configuration to an expanded configuration to press against the wall. The method may include moving the device/catheter and/or finger along the wall until a desired puncture location is reached. The method may include viewing the wall with imaging equipment and identifying a desired puncture location when the device/catheter and/or finger cause the desired puncture location to bend or bulge. The method may include identifying the desired puncture location as a location on the wall away from blood vessels and/or papillary muscles, e.g., when the bend/bulge appears on the wall in a location away from the blood vessels and/or papillary muscles.

The method may also include creating an incision or hole (e.g., puncturing and/or positioning an introducer) in the left and/or posterior wall of the left ventricle from inside the left ventricle to outside the left ventricle. If the device/catheter above is used to identify the desired puncture location, puncturing the wall may include directing a puncturing instrument and/or introducer at the desired puncture location and/or at a bulge/bend in the wall caused by the device/catheter above. The device/catheter may include a concave or inwardly tapered surface that can help guide and receive the puncturing instrument.

The method may also include deploying an anchor near a puncture location on the wall of the heart (e.g., at the puncture location on the left ventricle wall). If the treatment is remotely done (e.g., access to the heart is from a remote location and through a blood vessel, and incisions are not made to directly access the heart in the region of the incision), then deploying the anchor may involve advancing a delivery catheter through an access vessel, the right ventricle, the septum, and the hole/puncture in the wall of the left ventricle. The delivery catheter may have an anchor (e.g., any of the anchors described herein or shown in the figures) in a low profile configuration in a lumen of the catheter. The method may include deploying a first anchor from the lumen of the delivery catheter and outside the hole such that the first anchor transitions from the low profile configuration to an expanded configuration in a first location outside the heart. The method may also include pulling a tension member attached to the first anchor such that a portion of a cover of the first anchor is pulled toward the center of the expanded configuration (e.g., a circular configuration) to cause the cover to assume a flattened, disc-shape, cone-shape, or other shape/configuration. In one embodiment, the anchor may include a manually expandable ring that can be transitioned from a straightened, low profile configuration to an expanded, ring-like configuration by pulling an actuating wire, member, or cord that pulls the anchor into the expanded configuration. In one embodiment, the anchor may be expandable like a balloon by filling a balloon or cover (or portion thereof) with a filling material like beads, spheres, liquid, epoxy, etc.

If the treatment is not done remotely (e.g., it involves open heart surgery or minimally invasive surgery with local incisions on the chest to access the heart directly, i.e., without first passing through a blood vessel), then the first anchor can still be deployed from a delivery catheter that passes through the right ventricle (possibly accessed from outside the wall of the right ventricle or via an access vessel), the septum, and the hole/puncture in the wall of the left ventricle and then releases the anchor to transition from a low profile configuration to an expanded or deployed configuration similar to the description above with respect to remote access. The delivery catheter may be removed after deploying the anchor, thereby leaving the anchor and tension member or cord in place (e.g., the cord/tension member may remain in the pathway and have an end that extends outside the access site).

Optionally, the first anchor could also be deployed directly to the wall of the left ventricle from an incision in the chest. For example, the C-shaped device/catheter could include a lumen through which the tension member and anchor pass for deployment. Optionally, a second C-shaped device/catheter or other device/catheter could include a lumen through which the tension member and anchor pass for deployment. A snare may be passed from inside the heart to outside the heart via the hole/puncture in the wall of the left ventricle, and the snare could grab or ensnare the tension member. The snare could be withdrawn back into the left ventricle and through the septum (and optionally out of a hole in the wall of the right ventricle) while holding the tension member and bringing the tension member with it. The first anchor could be deployed against the wall of the left ventricle near the hole/puncture, and the tension member could be attached to a second anchor deployed at the septum or outside the right ventricle.

Methods may comprise deploying a second anchor in a second location, the second location being external to the heart outside the right ventricle or inside the right ventricle against a wall of the septum. The tension member may be attached to the first anchor and the second anchor and may be cinched/tensioned/pulled such that the first anchor and the second anchor are pulled toward each other and thereby alter the shape of the heart such that leaflets of the mitral valve overlap and better prevent mitral valve regurgitation. The tension member may then be secured relative to the first anchor and the second anchor such that the first anchor and the second anchor maintain the leaflets of the mitral valve such that they overlap. A clamp, auto-knotting device, crimping device, cord locker, or similar device maybe used to lock the tension member relative to an anchor (e.g., the second anchor). Any excess cord or tension member may be cut and removed, e.g., using a suture cutter catheter or other cutting device.

In the methods described herein, the puncturing instrument may be a flexible needle having slits along a length of the flexible needle, and the step of puncturing the septum may include using the flexible needle to penetrate and pass through the septum. The puncturing instrument may be a needle, and the step of puncturing the septum may include deploying a spade-shaped assembly in the right ventricle of the heart to stabilize the needle as the needle penetrates the septum. Optionally, the puncturing instrument may be an introducer assembly including a needle catheter having an introducer disposed in a lumen of the needle catheter, the introducer including an atraumatic distal end, and the step of puncturing the septum may include pushing the introducer assembly against the septum such that the atraumatic distal end of the introducer retracts into the needle catheter and a beveled edge of the needle catheter contacts and punctures the septum, and wherein after the needle catheter passes through the septum, the atraumatic distal end may extend from the needle catheter such that the introducer prevents the beveled edge from causing damage to surrounding tissue. The introducer may be locked in the extended position to prevent damage from the beveled edge. The method may also comprise passing a guidewire through a guidewire lumen in the introducer and into the left ventricle.

The puncturing instrument may be a trocar catheter including a cannula being generally elongate and having an interior lumen; a trocar disposed within the interior lumen and extending to a trocar distal tip comprising one or more surfaces (e.g., grinding plane surfaces) configured to allow the distal tip to puncture heart tissue; and the trocar catheter further comprising a proximal handle comprising controls configured to facilitate advancing the trocar distal tip beyond a distal end of the cannula during puncturing of heart tissue, the controls further configured to withdraw the trocar distal tip into the distal end of the cannula, and the step of puncturing the septum may include extending the trocar distal tip from the cannula, puncturing the septum, and withdrawing the trocar distal tip into the cannula to prevent further puncturing of heart tissue. The trocar may include a central lumen and one or more lateral ports disposed on the trocar distal tip and in fluid communication with the central lumen of the trocar, the central lumen and the one or more lateral ports being configured for contrast injection; and the step of puncturing the septum may include injecting contrast fluid into the heart via the central lumen and the one or more lateral ports, and imaging the trocar catheter and surrounding heart tissue during puncturing the septum. The step of creating a hole in the left and/or posterior wall of the left ventricle from inside the left ventricle to outside the left ventricle may include using a needle, needle catheter, or trocar to penetrate the left and/or posterior wall.

Methods may also comprise using a threaded introducer comprising an elongate member including a proximal head and a distal end; a central lumen extending from the proximal head to the distal end, the central lumen being configured for contrast injection; at least one lateral port disposed on the distal end in fluid communication with the central lumen; and threading disposed along a length of the threaded introducer; and the step of creating a hole in the posterior wall of the left ventricle from inside the left ventricle to outside the left ventricle may include rotating the threaded introducer against the posterior wall such that the threading rotatably engages with the posterior wall thereby advances the threaded introducer into the posterior wall in a controlled manner.

The first anchor may comprise a ring and a cover, the ring having atraumatic ends which meet at a break, the ring being in a straightened configuration in the lumen of a delivery catheter, and when deploying the first anchor from the lumen of the delivery catheter and outside the hole the ring may transition automatically to a ring-shaped configuration thereby causing the first anchor to transition from the low profile configuration to the expanded configuration.

Methods may further comprise suturing a portion of the heart with a suture and using a suture cutter catheter to cut a portion of the suture, wherein the suture cutter catheter comprises an inflatable balloon, a moving plate, and wherein inflation of the balloon causes the moving plate to press the suture into the blade to cut the suture. The suture cutter catheter may be used to cut suture and/or the tension member or excess thereof after cinching and locking the anchors together.

Methods of manufacture of the various systems, apparatuses, devices, etc. described herein may include creating the different components of the various systems, apparatuses, devices, etc., e.g., by mold, injection mold, 3D printing, extrusion, machining, grinding, milling, laser, and/or other methods. Methods of manufacture of the various systems, apparatuses, devices, etc. may also include assembling and/or attaching the components of the of the various systems, apparatuses, devices, etc. described herein in the arrangements/configurations described herein and/or shown in the figures. Attachments between components may be done by adhering, tying, bonding, fastening, friction fit, and/or otherwise securing the components together.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A self-expandable heart anchor comprising:
   a ring having a ring-shaped configuration and a straightened configuration, the ring in the straightened configuration being configured to be positioned inside a lumen of a catheter, and the ring being biased towards the ring-shaped configuration;
   a cover folded to form a passage at a periphery of the cover that receives the ring in the ring-shaped configuration, the cover configured to have a disc-shape with a central portion when the ring is in the ring-shaped configuration and being folded to form one or more loops at the central portion;
   a cord coupled to the one or more loops such that the cord when pulled cinches the one or more loops toward a center of the ring in the ring-shaped configuration.

2. The self-expandable heart anchor of claim 1, wherein a surface area of the cover is from 2 $cm^2$ to 6 $cm^2$ when the ring is in the ring-shaped configuration.

3. The self-expandable heart anchor of claim 1, wherein the cover is suitable to withstand forces due to tension of at least 17 Newtons when the ring is in the ring-shaped configuration.

4. The self-expandable heart anchor of claim 1, wherein the ring is made of a shape memory material, and the cover is made of a polymer material.

5. The self-expandable heart anchor of claim 1, wherein the ring has a rectangular cross-sectional shape.

6. The self-expandable heart anchor of claim 1, wherein the cover is configured to have a cone-shaped configuration when the one or more loops are pulled perpendicular to a plane of the ring in the ring-shaped configuration.

7. The self-expandable heart anchor of claim 1, wherein the cover includes triangular or wedge-shaped portions.

8. The self-expandable heart anchor of claim 1, wherein the cord is configured to cinch the one or more loops towards the center of the ring such that an inner area of the ring is filled with the cover.

9. The self-expandable heart anchor of claim 8, wherein the cord is coupled to the one or more loops at the center of the ring when the inner area of the ring is filled with the cover.

10. The self-expandable heart anchor of claim 1, wherein the ring includes a first portion that overlaps a second portion of the ring in a direction perpendicular to a plane of the ring in the ring-shaped configuration.

11. The self-expandable heart anchor of claim 10, wherein the first portion has the same diameter as the second portion.

12. The self-expandable heart anchor of claim 1, wherein the ring in the ring-shaped configuration includes a lower level and an upper level.

13. An anchoring system comprising:
a first heart anchor including:
a ring having a ring-shaped configuration and a straightened configuration, the ring in the straightened configuration being configured to be positioned inside a lumen of a catheter, and the ring being biased towards the ring-shaped configuration, and
a cover folded to form a passage at a periphery of the cover that receives the ring in the ring-shaped configuration, the cover configured to have a disc-shape with a central portion when the ring is in the ring-shaped configuration and being folded to form one or more loops at the central portion;
a second heart anchor; and
a cord configured to couple to the one or more loops of the cover and to the second heart anchor to thereby couple the first heart anchor to the second heart anchor, and the cord configured such that the cord when pulled from the cover cinches the one or more loops towards a center of the ring in the ring-shaped configuration.

14. The anchoring system of claim 13, wherein the cord is configured to be cinched to pull the first heart anchor towards the second heart anchor.

15. A method for treating heart dilation or heart valve regurgitation, the method comprising:
puncturing a septum of a heart between a right ventricle and a left ventricle of the heart with a puncturing instrument to form a hole in the septum;
deploying a first heart anchor to an outer wall of the heart outside the right ventricle or to a wall of the septum inside of the right ventricle, the first heart anchor including:
a ring having a ring-shaped configuration and a straightened configuration, the ring in the straightened configuration being configured to be positioned inside a lumen of a catheter, and the ring being biased towards the ring-shaped configuration, and
a cover folded to form a passage at a periphery of the cover that receives the ring in the ring-shaped configuration, the cover configured to have a disc-shape with a central portion when the ring is in the ring-shaped configuration and being folded to form one or more loops at the central portion for receiving a cord such that the cord when pulled cinches the one or more loops towards a center of the ring in the ring-shaped configuration;
deploying a second heart anchor to an outer wall of the heart outside of the left ventricle;
coupling the cord between the one or more loops of the cover and the second heart anchor, the cord extending through the hole in the septum; and
cinching the cord such that the first heart anchor and the second heart anchor are pulled towards each other.

16. The method of claim 15, further comprising cinching the one or more loops towards the center of the ring in the ring-shaped configuration.

17. A self-expandable heart anchor comprising:
a ring having a ring-shaped configuration and a straightened configuration, the ring in the straightened configuration being configured to be positioned inside a lumen of a catheter, and the ring being biased towards the ring-shaped configuration;
a cover folded to form a passage at a periphery of the cover that receives the ring in the ring-shaped configuration, the cover configured to have a disc-shape with a central portion when the ring is in the ring-shaped configuration and being folded to form one or more loops at the central portion, the cover configured to have a cone-shaped configuration when the one or more loops are pulled perpendicular to a plane of the ring in the ring-shaped configuration; and
a cord coupled to the one or more loops and configured to draw the one or more loops towards a center of the ring in the ring-shaped configuration.

18. The self-expandable heart anchor of claim 17, wherein the ring includes a first portion that overlaps a second portion of the ring in a direction perpendicular to the plane of the ring in the ring-shaped configuration.

19. An anchoring system comprising:
a first heart anchor including:
a ring having a ring-shaped configuration and a straightened configuration, the ring in the straightened configuration being configured to be positioned inside a lumen of a catheter, and the ring being biased towards the ring-shaped configuration, and
a cover folded to form a passage at a periphery of the cover that receives the ring in the ring-shaped configuration, the cover configured to have a disc-shape with a central portion when the ring is in the ring-shaped configuration and being folded to form one or more loops at the central portion, the cover configured to have a cone-shaped configuration when the one or more loops are pulled perpendicular to a plane of the ring in the ring-shaped configuration;
a second heart anchor; and
a cord configured to couple to the one or more loops of the cover and to the second heart anchor to thereby couple the first heart anchor to the second heart anchor.

20. The anchoring system of claim 19, wherein the cord is configured to be cinched to pull the first heart anchor towards the second heart anchor.

21. A method for treating heart dilation or heart valve regurgitation, the method comprising:
puncturing a septum of a heart between a right ventricle and a left ventricle of the heart with a puncturing instrument to form a hole in the septum;
deploying a first heart anchor to an outer wall of the heart outside the right ventricle or to a wall of the septum inside of the right ventricle, the first heart anchor including:
a ring having a ring-shaped configuration and a straightened configuration, the ring in the straightened configuration being configured to be positioned inside a lumen of a catheter, and the ring being biased towards the ring-shaped configuration, and
a cover folded to form a passage at a periphery of the cover that receives the ring in the ring-shaped configuration, the cover configured to have a disc-shape with a central portion when the ring is in the ring-shaped configuration and being folded to form one or more loops at the central portion for receiving a cord, the cover configured to have a cone-shaped configuration when the one or more loops are pulled perpendicular to a plane of the ring in the ring-shaped configuration;

deploying a second heart anchor to an outer wall of the heart outside of the left ventricle;

coupling the cord between the one or more loops of the cover and the second heart anchor, the cord extending through the hole in the septum; and cinching the cord such that the first heart anchor and the second heart anchor are pulled towards each other.

22. The method of claim 21, further comprising cinching the one or more loops towards a center of the ring in the ring-shaped configuration.

\* \* \* \* \*